(12) United States Patent
Koltin et al.

(10) Patent No.: US 6,465,198 B1
(45) Date of Patent: Oct. 15, 2002

(54) ESSENTIAL FUNGAL GENES AND THEIR USE

(75) Inventors: Yigal Koltin, Newton; Victoria Gavrias, Upton, both of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/911,882

(22) Filed: Jul. 23, 2001

Related U.S. Application Data

(62) Division of application No. 08/965,762, filed on Nov. 7, 1997, now Pat. No. 6,280,963.

(51) Int. Cl.[7] .......................... C07H 21/04; C12Q 1/68; C12N 15/63
(52) U.S. Cl. ................ 435/7.31; 435/254.3; 435/320.1; 536/23.1; 536/24.5
(58) Field of Search ............................... 435/7.1, 320.1, 435/254.3; 536/23.1, 24.5

(56) References Cited

FOREIGN PATENT DOCUMENTS

| WO | WO 95/06132 | 3/1995 |
|----|-------------|--------|
| WO | WO 95/10625 | 4/1995 |
| WO | WO 97/42210 | 11/1997 |

OTHER PUBLICATIONS

Berendsen, A glimpse of the holy grail, Science, vol. 2828, pp. 642–643, 1998.
Doshi et al.; "Two α–tubulin genes of *Aspergillus nidulans* encode divergent proteins"; *Mol. Gen. Genet.* vol. 225; pp. 129–141; 1991–XP002109954.
Du, database PIR2, Accession #S59791 Jan 13, 1996.
New England Biolabs Catalog, pp. 60–62, 1986/87.
Savitt et al., database PIR2, Accession #I50712, Sep. 13, 1996.
Topczewski et al.; "Cloning and characterization of the *Aspergillus nidulans cys B* gene encoding cysteine synthase"; *Current Genet.*, vol. 31, pp. 348–356; 1997— XP002109934.
Tuite; "Antifungal drug development: the identification of new targets"; *Trends in Biotechnology*, vol. 10, No. 7; pp. 219–220; Jul. 1, 1996– XP004035757.
Tuite; "Discovery and development of new systemic antifungals"; *Tibech*, vol. 14; pp. 219–220; Jul. 1996.
Yanai et al.; "Isolation and Characterization of Two Chitin Synthase Genes from *Aspergillus nidulans*" *Biosc. Biotech. Biochem.*, vol. 58; pp. 1828–1835; 1994—XP002109955.

*Primary Examiner*—Andrew Wang
(74) *Attorney, Agent, or Firm*—Fish & Richardson, P.C.

(57) ABSTRACT

Disclosed are essential Aspergillus polypeptides and genes (AN97, AN17, AN80, and AN85), as well as homologs thereof, which can be used to identify antifungal agents for treating fungal infections such as aspergillosis.

24 Claims, 46 Drawing Sheets

(SEQ ID NO:1)
1   AGCGCTGCCAGGGCAGCTGTGCCAAATGCGCCGACGCTTTGGCGAAACATCTGTCTCCTGAAACAGAAAAGACAAGACGAAGT    100
    TCGCGACGGTCCCGTGACACCGTTAGCGGCCTGCGAAACCGCTTTGTAGGACAGTTATAGTTACGACGAGACTTTGTCTTTCTGTCTGCTTCA
(SEQ ID NO:3)

101 TCCCCGATTGTATCTCGAATGAGGGACCGATTTCCGGCTGTAGTAAGAGGTCACGTGAAAGATGGCGTGCTAACTAGTATGCAAGGCATTTCCGGCTCA    200
    AGGGGCCTAACATAGAGCTTACTCCCCTGGCTAAAGGCCGCACTTCTCCAGTGCACTTCTACCGCACGATTGATCATACGTTCGTAAGCCGAGT

201 GGCAAAATACCCAGTCAACAATTTGTTGCTGAGGTGAAATACGAGACCCTTGATTGCGAGCAGTGTGATTAGGATAGCTGAGGCATTGTATTCAT    300
    CCGTTTTATGGGTCAGTTGTTAAACAACGACCTCCACCTTTATGCTCTGGGAACTAACGCTCGTCACACACTAATCCTATCCGACTCCGTAACATAAGTA

301 GTATCAGGAACCTGATCGTCTCAAAGCCGTTGCAGGCGTGCTGCAGGTCGGGCACAGTCCTGCCCTAACCCTATCTATCTACTGGTTTGGGGTGTTTGTTTATGCT    400
    CATAGTCCTTGACTAGCAGTTCGCAACGTCCAGCCCGACGTCCAGCCCGGATTGGGAATAGATAGAACCAAACCCCACAAACAAATACGA

401 CCGCCCCGTGACTCTCAGCAACGGTTATAACGAGTAGTGGCAGCAGCCAACGAACTTCTTTGCTGCCGACCTCACGCCAAACAAAGCCTTTACTGAAA    500
    GGCGGGGCACTGAGAGTCGTTGCCAATATTGCTCATCACCGTCGTTGAAGAAACGACGCGGTGGAGTGCGGTTTGTTTCGGAAATGACCTTT

501 CAGGCTGATCAGCAAATCAAGATATACTAGGATGAGTTGATATTATCACCGGCCGCAGATTACTGACCCGACACCCTTACTGCGTCATTACCCCTCGATC    600
    GTCCGACTAGTCGTTTAGTTGTTCTATATGATCCTACTACTCAACTATAATAGTGGCCGGCGTCTAATGACTGGGAATGACTGGGAGCTAG

FIG. 1A

```
601  AAGATGCCGAGTCGAGTGTTCCGCCCGTTCAACATCCACCGCCTTCGGCCAAGCCTTCTACACAGACTGCGCGCTGCTCAGCGACCCAT   700
     TTCTACGGCTCAGTCAGCTTCACAAGGCGGGCAAGCCGTTCCGGAGCGCGCGTTGTCTGACGTGTCGACCGCGACCAGTCGCTGGGTA
  1       M  P  S  R  V  S  A  R  S  T  S  T  A  S  R  K  G  S  T  Q  T  A  T  S  G  R  A  G  S  A  T  P  S    33
                                                                                             (SEQ ID NO:2)

701  CATTCGCCATCCCAGAGGAAACTGCATTACCCGAGGCTGTTCCAACCCTTGCGCCGATGTATGCGCCATTTTGCGGATCGTTCGACTGCCGG   800
     GTAAGCGGTAGGGTCTCCTTTGACGTAATGGGCTCCGACAAGTTGGGAACGCGGCTACATACGCGGTAAAAGCGCCTACGGTCGAAGCTGACGCC
 34       F  A  I  P  E  E  T  A  L  P  E  A  V  P  T  L  R  R  D  V  C  A  I  F  A  D  A  Q  R  S  T  A  G    66

801  TCATCGCAAACTGTCGTCCGACTAAGAAATCCAGGAGGTGTGCTGTATACCCCAGAAGAACTCAACAGTTCAACTGAAGAGCGATTG   900
     AGTAGCGTTTGACAGCAGCGGCTGATTCCTTTAGGTCCTCCACACGACACATATGGGGTCTTCTTGAGTTGTCAAGTTGACTTCTCGCTAAC
 67       H  R  K  L  V  V  R  L  R  K  I  Q  E  V  C  C  A  I  P  Q  K  N  S  K  K  D  S  S  T  E  E  R  L    99

901  ATTCCCGGCGAAGAGAACGGTACCAGAAAAGGAGTTCAACGTCGAAGTAGTCGTTGTGTTGGCCATCTGTCTATTAAGAAGACAGAGCCTGTTGGCG  1000
     TAAGGGCCGCTTCTCTTGCCATGGTCTTTTCCTCAAGTTGCAGCTTCAGCATTCAGCAACACACAACGGTAGAACAGATAATTCTCTGTCTCGGACAACGC
 100      I  P  G  E  E  T  V  P  E  K  E  F  N  V  E  V  S  R  C  V  L  R  I  L  S  I  K  K  T  E  P  V  G  D   133

1001 ATCGAATCCTGCGGTTTCTGCGGGAACTTCCTACTCATGCCTCGGAGATCTTCGGCTGGAAGAAGATGAAGACGATATGCAGAATTC   1100
     TAGCTTAGGACGCCAAAGAGACGCCCTTGAAGGATGAGTACGGAGCCTCTAGAAGCCGACCTTCTTCTACTTCTGCTATACGTCTTAAG
 134      R  I  L  R  F  L  G  N  F  L  T  H  A  S  E  K  D  A  E  I  F  G  S  E  E  D  D  M  Q  N  S         166
```

FIG. 1B

```
1101 GACGAAAGACCGACTGCCCACTGACCTGCTCTGTTGTCTGCAAAGACAAGGTTGTGCGCTTCCGTACCACGCAA     1200
     CGTGCTTTCTGGCTGACGGGTGAACTGGTGGTCAGAACAGAGGACAATCACGACGTTTCTGTTCCAACACGCATGGTGCGTT
167    H  E  R  P  T  A  H  L  T  T  S  L  V  S  L  L  V  P  L  L  S  A  K  D  K  V  V  R  F  R  T  T  Q    199

1201 ATTATCGCGCACATCGTCAATTCACTCGATACGGTAGACGAATTATACCACACTCTCCGCAAGGCCTTCTAAAACGGATTCGACAAGAACCTT     1300
     TAATAGCGCGTGTAGCAGTTAAGTGAGCTATGCCATCTGCTGCTTAATATGGTGTGAGAGGCCGTTCCGGAAGATTTTGCCTAAGCGTGTTCTTGGAA
200    I  I  A  H  I  V  N  S  L  D  T  V  D  D  E  L  Y  H  T  L  R  Q  G  L  L  K  R  I  R  D  K  E  P  S    233

1301 CGGTGCGGGTACAAGCAGTGATGGGTCTCGGCCGCTTGGCCGGAAATGAAGAGGACGATGACGAAAATGATATACCAGTGCCCTTGTGGAGAAGCTCGT     1400
     GCCACGCCCATGTTCGTCACTACCCAGAGCCGGCGAACCGGCCTTTACTTCTCCTGCTACTGCTTTTACTATATGGTCACGGGAACACCTCTTCGAGCA
234    V  R  V  Q  A  V  M  G  L  G  R  L  A  G  N  E  E  D  D  D  E  N  D  D  T  S  A  L  V  E  K  L  V    266

1401 GGACATAATGCAAAATGACACCGGCTGCAGAGGTTCGGAGGACATTACTCCTCACCTCCCATTGATTCCGTCTACCCTCCTCCTCGAACGGCGCC     1500
     CCTGTATTACGTTTTACTGTGCCGACGTCTCCAAGCCTCCTGTAATGAGGAGGTAACTAAGGCAGATGGAGGTATGGAGGAGCTTGCGCGG
267    D  I  M  Q  N  D  T  A  A  E  V  R  R  T  L  L  N  L  P  L  I  P  S  T  L  P  Y  L  L  E  R  A    299
```

```
1501 CGTGACCTGGATGCTCCCACACGAAGGGCATTATATTCTCGTCTACTTCCGACACTGGGAGATTCCGACATTTATCTCTCCATGAGAGAAAAGTTGC    1600
     GCACTGGAGCTACGAGGGTGCTTCCCGTAATATAAGACAGATGAAGGCTGTGACCCTCTAAAGCTGTAAATAGAGAGTACTCTCTTTCACG
300  R  D  L  D  A  P  T  R  R  A  L  Y  S  R  L  L  P  T  L  G  D  F  R  H  L  S  L  S  M  R  E  K  L  L    333

1601 TCAGATGGGGTCTTCTGATCGCGACAAAGTGTGAGGAAGGCCACTGACTGAAAGTGTTCTATGACCGCTGATTGAGATATGCTGCGAACGACAATGAC    1700
     AGTCTACCCCAGAAGCACTAGCGCTGTTTCACACTCCTCCGGTGACTGACTTTCAACAGATACTGGCGACTAACTCTATAGCGACCGTTGTTACTG
334  R  W  G  L  R  D  R  D  K  S  V  R  K  A  T  G  K  L  F  Y  D  R  W  I  E  I  S  L  A  R  T  M  T    366

1701 CCTGAGAATTCGGGCAGCGCTCGAACAGAGAATTCCCGCTTTACTGGAGTGTTGTTGGAGCGTATCGATGGTGAACTCAGGCATGAATCCGGCATAGCG    1800
     GGACTCTTAAGCCCGTCGCGAGCTTGTCTCTTAAGGGCGAAATGACCTCACAACCTGCATAGTCTACCACTGAGTCGTACCTTAGGCCGTATCGC
367  L  R  I  R  A  A  L  G  T  R  I  P  A  L  L  E  L  L  E  R  I  D  V  V  N  S  G  M  E  S  G  I  A    399

1801 CACGAAGCTATGCGCAGTTTCTGGAAGGTCGACCAGACTATCGAGAGGCGTACTATTGACGAAGCCTTCTGGGAGTCAATGACAGCAGAATCCGCTT    1900
     GTGCTTCGATACGCGTCAAAGACCCTTCCAGACGGTCTGATAGCTCTCCGCCATGATAAGCTGCTTCGGAAGACCCTCAGTTACTGTCGTCTAGGCGAA
400  H  E  A  M  R  S  F  W  E  G  R  P  D  Y  R  E  A  V  L  F  D  E  A  F  W  E  S  M  T  A  E  S  A  F    433

1901 TCCTCCTTGCTTCATTCAATGACTTTTGCCGGGTTGAAAACGAAGTAAATATGACAGCCTGCCGATGAGAAGATCCAGTCGTTACAGCCCTGCAAT    2000
     AGGAGGAACGGAGTAAGTACTGAAACGGCCCAACTTTGCTTCCATTTATACTGTCGGACGGCTACTCTTCTAGGTCAGCAATGTCGGAGCGTTA
434  L  L  R  S  F  N  D  F  C  R  V  E  N  E  G  K  Y  D  S  L  A  D  E  K  I  P  V  V  T  A  L  A  M    466
```

```
2001  GTATCTTCATAAGTACATGACCGAGCTTCTCAGCCGCAAGAAGCTCACAAAGAGATCTACTGAGCGTAAACGACGACGATACCGTGAAATCGAATTTATC    2100
      CATAGAAGTATTCATGTACTGGCTCGAAGACGTCGGCGTTCTTCGAGTGTTTCTCTACGATGACTGACTTGCTGCTGCTATGGCAGCTTAGCTTAAATAG

467    Y  L  H  K  Y  M  T  E  L  L  Q  R  K  K  L  T  K  D  A  T  D  V  N  D  D  D  T  V  E  I  E  F  I     499

2101  GTCGAGCAACTGCTTCACATCGCGATGACACTAGACTACAGCGACGAAGTTGGGCGGCGAAAGATGTTTCTCTACTCCGTGAGGCTCTCGCTGTCCCAG    2200
      CAGCTCGTTGACGAAGTGTAGCGCTACTGTGATCTGATGTCGCTGCTTCAACCCGCCGCTTTCTACAAAGAGATGAGGCACTCCGAGAGCGACAGGGTC

500    V  E  Q  L  L  H  I  A  M  T  L  D  Y  S  D  E  V  G  R  R  K  M  F  S  L  L  R  E  A  L  A  V  P  E    533

2201  AGCTCCCTCAGAATCGACCAAGCTCGCGGTTGAGACACTCGTGACTCTGAGCGCCAACTCTGTGACTCTGCTTCGCTTAAGACGTCACAACAAGACCT    2300
      TCGAGGGAGTCTTAGCTGGTTCGAGCGCCAACTCTGTGAGACGCTGCGGTTGAGACACTGAGACGAAGCGAATTCGAGTGTTGTTCTGA

534    L  P  Q  E  S  T  K  L  A  V  E  T  L  R  C  V  C  G  P  D  A  A  A  E  S  E  F  C  S  V  V  L  E     566

2301  AGCCATTGCTGAAGTTCATGACACAATCAGCACCGAGGATAGTTTCGTTTCTGCAAAGTCTGAGATTAGGCGATGATGCCAGCAGCCGCCAACGATCCGAA    2400
      TCGGTAACGACTTCAAGTACTGTGTTAGTCGTGGCTCCTATGCAAAGCGTTTCAGACGTTCAGACTGTAATGCTACTACGGTCGTCGGCGGTTGCTAGGCTT

```
2401  ACGCCGATGAGTGAAGATGACAAGCCATTCAACAAGGAGGCAAAGGCTAAGGTCCTCAAGGAAATCGTTATTAATATGAAGTGTCTGCACATTGCCC    2500
      TGCGGCTACTCACTTCTGGTTCGGTAAGTTGTTCCTCCGTTTCCGATTCCAGGAGTTCCTTTAGCAATAATTATACTTCACAGACGTGTAACGGG

600   T  P  M  S  E  D  D  K  P  F  N  K  E  E  A  K  A  K  V  L  K  E  I  V  I  N  M  K  C  L  H  I  A  L    633

2501  TTTGCATGCTCCAGAATGTTGAAGGCAACCTGCAAGCAAATATGAATCTGGTGACCATGTTGAATAACTTGGTAGTACCTGCTGTTCGAGCCACGAAGC    2600
      AAACGTACGAGGTCTTACAACTTCCGTTGGACGTTCGTTTATACTTAGACCACTGGTACAACTTATTGAACCATCATGGACGACAAGCTCGGTGCTTCG

634   C  M  L  Q  N  V  E  G  N  L  Q  A  N  M  N  L  V  T  M  L  N  N  L  V  V  P  A  V  R  S  H  E  A    666

2601  GCCAATTCGAGAGGCGGGTCTCGAATGTCTCTTGGGCTGTCTGCTGCGACAAGCTAAGTTCCATCCTACTAAATACATCTTCTCTAACCTCTCT    2700
      CGGTTAAGCTCTCGCGCCAGAGCTTACAGAGAACCCGACAGACGACGAACGACCTGTTCATTCAAGTAGGAATGATTTATGTAGAAGAGATTGGAGAGA

667   P  I  R  E  R  G  L  E  C  L  G  L  C  C  L  L  D  K                                                 684

2701  GTTAGACTCTGCAGAAGAAAATATGACGCTGTTTATTCACTGTTACAGCAAGGCCACGAAAACCTACAGTCACTGTCAGTGCTATTCATATCCTTTGCGATAT    2800
      CAATCTGAGACGTCTTCTTTTATACTGCGACAAATAAGTGACAATGTCGTTCCGGTGCTTTTGGATGTCAGTCACAGATAAGTATAGAAACGCTATA

685   T  L  A  E  E  N  M  T  L  F  I  H  C  Y  S  K  G  H  E  N  L  Q  V  T  A  I  H  I  L  C  D  M    716
      (SEQ ID NO:29)

2801  GTTAATTAGCCATCCTTCGCTGGTGCTCCCGGCCGTTACCCAGGCCGATAAGGAGGACAGTTGCGCCACCGGCGTTCCAGAAGCCACTGCTTAAGTCTTTTCC    2900
      CAATTAATCGGTAGGAAGCGACCACCGAGGGCAATGGGTCCGCTATTCCTCGTCAACGCGGTGGCCGCAAGTCTTCGGTGACGAATTCCAGAAAGG

```
3401  CAATGTTTGTGTGGCATTATCCACTTGCAACTGATTAAGGACATATACTGAAACGAGTGCTCGGGATCAGTGAAGGCAGCAATCGCTGCTCTAAACAACAACGA  3500
      GTTACAAACACCGTAATAGGTGAACGTTGACTAATTCCTGTATGACCTTGCTCACGAGCCTAGTCACTTCCGTCGTTAGCGACGAGATTGTGTTGCT
917   N  V  C  G  I  I  H  L  Q  L  I  K  D  I  L  E  R  V  L  G  I  S  E  G  S  N  R  C  S  K  Q  Q  R    949

3501  AAACTCCTGTTTCACTCATGAGCAAGCTCTATATTGCGCCAACGGCACTTCGCGCTCAGCCTGTCCAGGCCCCGAAGACGACTCGTTCCGTTCCA     3600
      TTTGAGGACAAAGTGAGTACTCGTTCGAGATATAACGCGGTTGCCGTGAAAGCGGCAGTCGGAGTCGAGGTCCGGGGCTTCTGAGCAAGGCAAGGT
950   K  L  L  F  S  L  M  S  K  L  Y  I  A  P  P  T  A  L  S  R  S  A  S  Q  A  P  E  D  D  S  F  R  S  S    983

3601  GCGTGCGAAGCTCCCATGGCGAACTCAATCCCGAAACCTGCCCTCGCGCAGAAGTCAAGGAGTACTGACCAGACCATCGAAGAAGGTGTGGCGGC    3700
      CGCACGCTTCGAGGGTACCGCTTGAGTTAGGGCTTTGGACGGGAGCGCGTCTTCAGTTCCTCGATGAACTGGTCTGGTAGCTCTTCCACACCGCCG
984   V  R  S  S  H  G  E  L  N  P  E  N  L  A  L  A  Q  E  V  K  E  L  L  D  Q  T  I  E  E  G  V  A  A   1016

3701  TGATGCTGCTAGCCGAAATGCCCTCGTCAAGGTGAAGAACGTGGTCTCAAGCTACTGGCGGCTCCATGCGACCTTCTAGCGACGGCCGCGAGAGC    3800
      ACTACGACGATCGGCTTTACGGGAGCAGTTCCACTTCTTGCACCAGAGTTCGATGACCGCCGAGGGTACGCTGGAAGATCGCTGCCGGCGCTCTCG
1017  D  A  A  S  R  N  A  L  V  K  V  K  N  V  V  L  K  L  L  A  A  P  M  R  P  S  S  A  R  G  R  E  S   1049

3801  AGTGTGAAAGTGACATTGGCAGTGTCGATCTTCCAGAAGTGTTCCGGCGTTGGGCGCCGGGCCTTGGCTTTGGGGCCGGTGTATCCGTGAGCCAGTA  3900
      TCACAGCTTTCACTGTAACCGTCACAGCTAGAAGGTCTTCACAAGCCGCAACCCGCGGCCGGGAACCGAAACCCGGCCCACATAGGCACCTCGGGTCAT
1050  S  V  E  S  D  I  G  S  V  R  S  S  R  P  S  V  R  P  S  V  E  P  G  F  G  R  R  G  V  S  V  E  P  S  I   1083
```

FIG. 1H

```
3901  TCATGGAGGAGGATGAGAATGAGGATAGCCGGGCGACTCTGGACAGTAGAATGACTGTTATCAAAGAGGAGGATGCCGACGCTATGGAGGAATGATTTTC  4000
      AGTACCTCCTCCTACTCTTACTCCTATCGGCCCGCTGAGACCTGTCATCTTACTGACAATAGTTTCTCCTCCTACGGCTGCGATACCTCCTACTAAAG

1084                  M  E  E  D  E  N  E  D  S  R  A  T  L  D  S  R  M  T  V  I  K  E  E  D  A  D  A  M  E  E  *        1113

4001  GGTCTCAAGATCTTTGCTGTCTGGTTCGGCGTGTGGGGAGTTTCCCGGCAGGGCTAATGGTCATATTTATGGTTGCGATGTAATTATTCGATTCT        4100
      CCAGAGTTCTAGAAACGACAGACCAAGCCGCACCCTCGGATTACCCAGTATAAATACCAATCCAACGCTACATTAATAAGCTAAGA

4101  TGGTTATGCTTGAACATGCTCTATATGTTACAAATAATTCACTCCAAACGTTCATGTATGAGTATGATCTGTTTTATATTGGCCTTACCAGGATAGCTC        4200
      ACCAATACGAACTTGTACGAGATATACAATGTTTATTAAGTGAGGTTTGCAAGTACATACTCATACAAAATATAACCGGAATGTCCTATGCGAG

4201  AGTTCTTGGGCGAAGTTATCCCAGACTGACAGCTGCCTCCAGGCCAGAATTGGCTAGTCTTAGTCTTAGTAGCATCGAGTTAGTAGCATCGAGTTATCAACAG        4300
      TCAAGAACCGCTTCAATAGGTCTGACTGTCGACGAGGTCCGGTCTTAACGATCAGAATCAGAATCATCGTAGACTCATGATCATCGGTGTC

4301  TGATCAGTGTGGAAGGGCCATCCGATCTGTTTGATCTTACCAGAACGTGTTACAACAATTCAACCACCATATATGTATCTACGTCAATGTCAATGA        4400
      ACTAGTCACACCTTCCCGGTAGGCTAGACAAACTAGAATGTCTTGACAATGTCGTTAAGTTGGGTGTATATATACCATAGATGCAGTTACACTTACT
```

FIG. 11

```
4401  ATCTGCTTGGGCAGCCTTATGACTCTGGTGACGCGGACTCGGGCTTGATTCAATGCGGGACTCGGGCTTGAGACTCCTAGCATCCGATGTGAGGCT  4500
      TAGACGAACCCGTCGGAATACTACTGAGACCTGAGACCACTGCGCTGACCTGCGAGCCGCCCGTTCTGCCGTACGCCCGTTCTGGCGTACGGCGTACCCTTCTGAGGATCGTAGCCTACACTCCGA

4501  TCCGTGTTTAATTTCTTCCTCCAAATCGTCTGCCTGCCTGCGCTCCTGCTTGAAATACTCCGGAGTACCAAAGTAAAGATAAATGGTTGACTCTGAGAGACTG  4600
      AGGCAAAATTAAAGAAGGAGGTTTAGCAGACGACGGAGCCGACGAAACTTTATGAGGCCTCCATGGTTCATTTCTATTTACCAACTGAGACTCTCTGAC

4601  CTTTTGACCTCCTGGACCAAGTCGTCTGCCTAGCCAGAAGGGGACGAGTGTTCAATGGGCTTTGTGAGGCTACTAAGGCCGACGATACACCGGAGATGCAAAGAA  4700
      GAAACTGGAGACCTGGTTCAGCACGACGTCGGTTCTCCCCTCACAAGTACCCGAACACTCCGATGATTCCGGGTGCTATGTGGCCTACGTTCTT

4701  GTCCGATACGGTCGTCATATCTCGAGCACCTTTATTACTGGCCGCTTTGCAGTTATATGAAGGCGGTTAATGATTGGCTGCGTGTTCGAATCGATGAATAA  4800
      CAGGCTATGCCAGCAGGTATAGAGCTCGTGGAAATATGACCCGGAAATCAATATGTCAATATTACCTCCGAAATTACTAACGCACAAGCCTTAGGCTACTTATT

4801  TATCTCGATTAGTTGGACTAAACGGGGATGGATGAAGACTCGTCTGTATCTTGGTCTCAAACTGTAATAAGCGTCTCGGCAACACCGTACGGTTGACAAT  4900
      ATAGAGTAATACAGCTGATTTGCCCCTACTCCTACCGACGAGTTTGACATTATTCCGAGAGCCGTGTGCATGCCAACTGTTA

4901  CCTGGGCAGATGGCAGCACCTGTAGAATCCAAGAAGACCAGCTGACTCATTGAGACAGTTGAATTCCTTAACTATAATGACAGACTAATAATACAAAA  5000
      GGACCCGTCTACCGTCGTGGACATCTTAGGTTCTTCGCGTCGACCTGAGTAACTCTGTCAACTTAAGGAATTGATATTACTGTCTGATTATTATGTTTT
```

FIG. 1J

```
5001  GTGCGGTGGTCAACTTCTTCCCAATCCCCTGTTCTTTCTAATAATCGACGCTCCACCAAAGTCCAGCTTCTGGCGAC  5100
      CACGCCACCAGTTGAAGAAGGGTTAGGGGAGTTTTCAGTCTGGGCTGGGACAAGAAAGATTATTAGACTGCGAGGTGTTTCAGGTCGAAGACCCGCTG

5101  TTTCTTTTCTTCCCATCCTTTCCTTCTCTCGCTTCTCTCCTCCCCTCTCTCCTCTTCCTTGCTGTATGTTTTTGTCTGATTCACGACTT  5200
      AAGAAAAGAAGGGGTAGGAAAGGAAAAGGAAGAGGAGAGAAGGAAGAAGAAAGCGAAGTACAAAAACAACAACTAAGTGCTGAA

5201  TCTTTTTCCTTCGTCGTGGATCCGTCTTCGCCCCACTTGCAGAGGCACGATTTTCTCCCTTTCCCCTCTACTCCCCCCTCC  5300
      AGAAAAGGAAGACCAGCACTCGTGCCGTAGCTGCTAAACGTCTCCGTGCTAAAAGAGGAGAGGAAGGCATGAGGGGGAGG

5301  CCCCTGCTCTGCGCCTTTGGCATCCGGAGCCGTCGTCGAGACCGTGCTGGCCTCAGCTGTCCACGCCCAAGCTGACCGCTACATCGTCGT  5400
      GGGGACGAGACGCGAAACCGTAGGCGTCGACTTGAGGCCTGGGCACTCGCTACCGGAGCACAGTCGAGGTCGAGGTTCGACGTTGACCTGGGCCGATGTAGCAGCA

5401  TCATGTGCAACTACCTGCGATGAGCTACGCCTCTACGTCTACCAAGGACTCTGAGAGTGATGATCGAGTGGGGTGGATCTTGTTGGATACCAAACCTGCG  5500
      AGTACACCGTTGATGAGTCGTACTGCGACGCTCGACGCAGATCGAGTCAGTGGTTCCTGAGACGTCTCACTAGCTCAACCCACCACTATGGTTTTGACGC

5501  AGAGTCGCAGTGATTCTCTCCCTGCACCACTATTCCACCCCCTCTTTTGTCTTGATTCTGCCGCCGCCCTACCGGATTCTGCCGACGACATT  5596
      TCTCAGCGTCACTAAGAGAGGGAACGTGGTGTGATAAGGTGGGGGAGAAAACACAGAACTAAGAGCCCTAAGCGGCCGATGGCCCTGCTGTAA
```

FIG. 1K (SEQ ID NO:4)
1    CAAAGTCTTGATCACAGGGGCACAAGCGCACCATGCTTACGGACGGCATCGAAGGGGTCAAGGAGAAGTCTTTGTCGTCGTGACCGTG    100
     GTTTCAGAACTAGTGTCCCCGTGTCGGCGTTCGCGTTAACTCGGTGGTTACGAATGCCTGCGTAGCTTCCCCAGTTCCTCTTTCAGAACACGAGCACTGGCCAC
(SEQ ID NO:6)

101  CCAACAGTACAGTGAAACCCTGCGCTCTGTCCTATCTCATGCGGTCCGTCGTTAGTGGTTTATGTTCTAACTGTTACCCCTGTGGGTTTTCACCGTTT    200
                                        M  F  L  T  V  T  P  C  G  F  S  P  F
                                                            (SEQ ID NO:5)

201  AGCGGACTAGGATACTCAACGTGTTGCCGTCTTGCAGATGAATTCCTGGCGTCTCATGGAACGACCATCGTTCATTGACAATCATCTTCACTACCCGA    300
      S  G  L  G  Y  S  T  C  C  R  L  A  D  E  F  L  A  S  H  R  N  D  H  R  S  L  T  I  I  F  T  T  R  S

301  GCACAAGAAAGGGAAGCGACACTCCGCTGTGCCTTCGTTCCACCTCGGTGCTTCCGGCCACCGCTTCGAGTGACCTTCGTTCCTGA    400
      T  R  K  G  S  D  T  L  R  N  L  Q  N  H  L  R  T  S  T  F  G  A  S  A  T  A  R  V  T  F  V  V  P  E

401  AAATGTCGACCTCTGCAACCTCTCTGTCCGCGCTATCCGTGCTGAACAAGACCTTCCCAAAACTGACGGCGATTGTGCTTAATGCGGGATA    500
      N  V  D  L  C  N  L  L  S  V  R  A  L  S  R  R  L  N  K  T  F  P  K  L  D  A  I  V  L  N  A  G  I      113

FIG. 2A

```
501  GGGGGTTGGTCTGCCTCAATTGGCCTCTGGCCGTATGGAGGCGTTTGCACGGACGACGTGGCCAAAGTACAAATTGCGCCTGTAG   600
     CCCCAACCAGACCGGAGTTAACCGGGAGACCGGCATACCTGCAAACGTGGCTGCACCGGTTCATGTTTAACGCGGACATC
114  G  G  W  S  G  L  N  W  P  L  A  V  W  S  V  C  T  D  I  I  H  A  T  T  W  P  K  Y  K  I  A  P  V  G   147

601  GTCTCATAACGGACAACCAGAGACAATTACTGTGACCGACAAGGAGCCCCGCCTCTGTGGCCAACGTCTTCTGCGCCAACGTGTTCGGCCACTACATGCTCGCGCA   700
     CAGAGTATTGCCTGTTGGTCTGTTAATGACACTGGCTGTTCCTCGGGGCGGAGACACCGGTTGCAGAAGACGGGTGATGTACGAGCGCGT
148  L  I  T  D  N  Q  T  I  T  V  T  D  K  E  P  R  L  G  T  V  F  C  A  N  V  F  G  H  Y  M  L  A  H   180

701  TAATGTCATGCCTCTCCTGCACCGATCCCCAACGGACCCGAAGCCGTGATATGGCTCTCAGCACTGAAGCACTGACTTCTTCGATGTT   800
     ATTACAGTACGGAGAGGACGGTGGCTAGGGCCTGGGGGTTGCCTGGCACTATACCGAGAGTCGTGACTCGTAGTTGAAGAAGCTACAA
181  N  V  M  P  L  L  H  R  S  G  S  P  N  G  P  G  R  V  I  W  L  S  S  T  E  A  T  I  N  F  F  D  V   213

801  GATGATTTTCAGGCGCTCCGGTCCAAAGCTCCCTACGAGTCATCAAAAGCGCTAACAGACCTCCTACCCTCACCTAGACCTTCCAGTACTGCTCCCT   900
     CTACTAAAAGTCCGCGAGGCCAGGTTTCGAGGGATGCTCAGTAGTTGTCTGGAGGATAGGAGTGGAGTCTGAAGGTCATGACGAGGGA
214  D  D  F  Q  A  L  R  S  K  A  P  Y  E  S  S  K  A  L  T  D  L  L  S  L  T  S  D  L  P  S  T  A  P  W   247
```

FIG. 2B

```
 901  GGGTGAAAAGCTTCTATTCCACCGACTTCGAAACCGATTCCAAGCCCAGCTGGAACCGCCTCGAACCTGAGAGAGTGGG   1000
      CCCACTTTTCGAAGATAAGGTGGCTGAAGCTTTGGCTAAGGTTCGGCTGAAGCTTGGACTGGTGCCGAGCTTGTCATGAGAGAGTGGG
 248                V  K  S  F  Y  S  T  D  F  E  T  D  S  K  P  S  T  G  P  E  T  A  S  T  I  P  N  V  Y  L  S  H  P    280

1001  CGGAATCTGCGCTAGCGGCGATTATACCCCTTCCTACAATCCTCATCTACGCGAATGTGCCGGCATTTTGGCTAGCCCGCATCCTCCCCTTGGCAT   1100
      GCCTTAGACGCGATCGCCTAATATGGGAAGGATGTTAGGAGTAGATGCGTTACCAGGCGTAAAACCGATCGGGCGTAGAGCCGAGGGGAACCGTA
 281   G  I  C  A  T  A  I  I  P  L  P  T  I  L  I  Y  A  M  V  A  A  F  W  L  A  R  I  L  G  S  P  W  H    313

1101  ACCTTATCCACCTACCTAGGCGCTTGCAGCCCTGTCTGGCTTGCTCTCCACACAATCAGAACTCGACGCCGCCGAACCACCGTACCGGAAACACGGCG   1200
      TGGAATAGGTGGATGGATCCGCGAACGTCGGGACAGACCGAACGAGAGGTGTTAGTCTTGAGCTGCGGCGGCTTCCTGGCATGGCCTTTGTGCCGC
 314    T  L  S  T  Y  L  G  A  C  S  P  V  W  L  A  L  S  T  Q  S  E  L  D  A  A  E  A  P  Y  R  K  H  G  G   347

1201  GCGGCAGGGTGAAATGGGGGTCTTCGGGCGTCTCGATTAGTGTAGCCTCCGAGGTTGACGATGGGCTATGGGGGTGTTCCTGGGGC   1300
      CGCCGTCCCACTTTACCCCCAGAGAAGCCGCAGAGCATAATCACATCGGAGCAGCATAGAAGCCTCCAACTGCTACCCGATGCCACAAGACCCCG
 348  G  R  V  K  W  G  S  S  A  S  R  L  G  V  A  S  V  V  S  S  E  V  D  G  W  G  Y  G  G  V  P  G  A    380

1301  CGGCTGTCTGGCGGAGGATAGGGTCTGAAGGCGCAAGCGTGGTGCAGTGGATCTTACGGCGTGAGGGGAAGGAGGGATTCCAGGAACTGGGGGCTATATG   1400
      GCCGACAACACCGCCTCCTATCCCAGACTTCCGCGTTCGCACCAGGTCACCTAGAATGCCGACTCCCCTTCCCTAAGGTCCTTGACCCCGATATAC
 381   G  C  C  G  G  G    *                                                                                386
```

FIG. 2C

```
1401 TTGGAGGCAGATGGAGGAGCTGAGGATCCTGTGGATAACTTACTTGATGAAGAGAAGGGGACTGGTGTGACGGCGTAGGTGGCTTGTCTGGGAGTG
     AACCTCCGTCTACCTCCTCGACTCCTAGGACACCCTATTGAATGAACTACTCTCTCTTCCCCTGACCACACTGCCGCATCCACCGAACAGAGACCCTCAC   1500

1501 AGATCTCTTACATTCGGCCTTCGTCCCTAAATCTTTCTCCCCTTCTCTTTATTATACGATGTCGGCGGTTTTATGTTCAATACAGCACATCTACGG
     TCTAGAGAATGTAAAGCCGGAAGCAGGATTTTAGGAAAAGAGGAAGGAAATATGCTACAGCCCGCCAAAATACAAGTTATGTCGTGTAGATGCC         1600

1601 TACAAAGACAACATATAGCTAATAATATAATATCATAGATAATAGTAATAATCAAGCACAAAGCTCGATTCGCAAGATCTCAATATCTTTATTCCAGTTTT
     ATGTTTCTGTTATATCGATTATATTATTAGTATCTATTATCATTATTAGTTCGTGTTTTCGAGCTAAGACGTTCTAGAAGTTATAGAAATAAGGTCAAAA   1700

1701 CACTGCTCTGTCTTCCATATTTACATTCCACGTCCACGTGCATCCTTTAAAACAGT  1758
     GTGACGAGAACAGAGAAGTATAAATGTAAGGTGCAGGTGCACGTAGGAAATTTTGTCA
```

FIG. 2D (SEQ ID NO:7)
1   GAATTCCTGTGATGGAGCAGAGAACCTCGGAGTATGCTCCGATGTCAGTACATTAAATTTTGTAGCGATCCACGTGATTTCTATTTGCGTCCCGAATAGGT
    CTTAAGGACACTACCTCGTCTTGGAGCCTCATACGAGGCTACAGTCATGTAATTTAAACATCGCTAGGTGCACTAAAGATAAAGCAGGCGTTATCCA
(SEQ ID NO:9)

101 CTTCTGATACGGCTGAAGAAATATAGTACGGTGGTCCAGTGCCTATAGACGGAAAGTATTTCGTACGGTTGGCTCCCAAGGCAATAGTGTCAACCTCGCAT
    GAAGACTATGCCGACTTCTTATATCATGCACCAGTCACGGATATCTGCCTTTCATAAAGCATGCCAACCGAGGGTTCCGTTATCCAGTTGGAGGGTA

201 ACGGAGAATAACGGTACGGTCCTGAAGGAATGAGGGGATGTATTCCTCCTTCTCCGAGGGCCAGAAGGGGAACAGGCCCCGGACTGATCGGCGAAAATTTC
    TGCCTCTTATTGCCATGCCAGGACTTCCTACTCCCCTACATAAGGAAGAGGCTCCCGGTCTTCCCGGTGACTAGGCCGCTTTTAAAG

M   R   G   C   I   L   L   L   R   G   P   E   G   E   Q   A   R   T   D   P   A   K   I   S
                                                                                              (SEQ ID NO:8)

301 CCCCTCTGAGTCTTCGCTTCCCCCCACACGGCTGACTAACCCTTCCATTCTTGCCCGCATCCAGCCAGCCCTTTGTGGCCGCCCTTGGTTCGG
    GGGAGAGCTCAGAAGCGAAGGGGGGTGTGCCGACTGATTGGGAAGGTAAGAACGGGCGTAGTCGGTCGGAAACAGGCGGGGGACCAAGCCC

25   P   L   D                              (SEQ ID NO:30)  L   L   S   P   P   L   V   R   A    36

FIG. 3A

```
401  CTACTGTCAATCTTCCCTCTTCTTCATCTCTTGCTCTGACTGAAATATTCAGTCTTCTGATTTACAGTTACTACGGCAGACACGCTGCACAT   500
     GATGACAGTTAGAAGGGAAGAAGATAGAAGTACGGCGAGAGCTGACTTTATAGTCAGAAGACTAAATGTCAATGCGGGTCTGTGACGTGTA
 37   T  V  I  F  P  S  S  S  C  R  S  R  L  K  Y  S  V  S  C  S  D  L  Q  L  L  R  A  D  T  L  H  I    69

501  CTCCGGCGATCATGACCGAATCCACTCAAGAACAGGCAACGATGGCCAGCGAATGCCCCGCCGGCGACCCCCGTTGAGGATTACGTCTCCCTGAA   600
     GAGGCCGCTAGTACTGGCTTAGGTGAGTTCTTGTCCCGTTGCTACCGGTCGCTTACGGCCGGGGGCAACTCTAATGCAGAAGGGACTT
 70   S  A  I  M  T  E  S  T  Q  E  Q  G  N  D  G  Q  R  M  P  P  A  P  A  T  P  V  E  D  Y  V  F  P  E   102

601  TATCGCCTGAAGCGTGTGATGGATGACCCGGAAAAGACGCCGCTATTGCTTATAGCTTGCGGTTCATTCTCACCTATTACGTTCCTGCACCTGCGCATGT   700
     ATAGCGGACTTCGCACACTACTGGGCCTTTTCTGCGGCGATAACGAATATCGAACGCCAAGTAAGAGTGATAATGCAAGACGTGGACGCGTACA
103   Y  R  L  K  R  V  M  D  D  P  E  K  T  P  L  L  L  I  A  C  G  S  F  S  P  I  T  F  L  H  L  R  M  F   136

701  TCGAAATGGCCGCCGATTACGTCAAACTGAGCACAGATTTCGAAATAATTGGAGGTTATCTTTCGCCCGTCTCGGACGCCTACCGCAAGGCAGGTCTTGC   800
     AGCTTTACCGGCGGCTAATGCAGTTTGACTCGTGTCTAAAGCTTTATTAACCTCCAATAGAAAGCGGGCAGAGCCTGCGGATGGCGTTCCGTCCAGAACG
137   E  M  A  A  D  Y  V  K  L  S  T  D  F  E  I  I  G  G  Y  L  S  P  V  S  D  A  Y  R  R  K  A  G  L  A   169

801  GAGTGCCAATCACAGGTAGTTACTTTAACACACTTCTTCCATAGTTACTATCCAGGACTGATCTGGCGGCTTTAGAATTGCAATGCCAACGAGCCGTG   900
     CTCACGGTTAGTGTCCATCAATGAAATTGTGTGAAGAAGTATCAATGATAGGTCCTGACTAGACCGCCGAAATCTTAACGTTACACGGTTGCTCGGCAC
170   S  A  N  H  R         (SEQ ID NO:31)  I  A  M  C  Q  R  A  V   182
```

FIG. 3B

```
 901  GACCAAACGTCAGACTGATGATGTGATACATGGGAGCCGATGCACAAGGAGTACCAGCCAACTGCCATCGTACTGCTGATCATTTGACTACGAGATCA   1000
      CTGGTTTGCAGTCTGACTACTACCACCTATGTACCCTCGGTTCCTCATGGTCGGTTGACGGTAGCATGACCTAGTAAAACTGATGCTCAGT
 183  D  Q  T  S  D  W  M  M  V  D  T  W  E  P  M  H  K  E  Y  Q  P  T  A  I  V  L  D  H  F  D  Y  E  I  N   216

1001  ACACTGTCCGCAAAGTATCGATACCGGAAAAGGCACTCGAAAGCGAGTGCAAGTCGTCTTATTGGCCGGGCAGATTGGTCCATACCATGTCTACGCC   1100
      TGTGACAGGCGTTTCATAGCTATGGCCTTTTCCGTGAGCTTCGCTCACGTTCAGCAGAATAACCGGCCCGTCTAAACAGGTAGTACAGATGCGG
 217  T  V  R  K  G  I  D  T  G  K  G  T  R  K  R  V  Q  V  V  L  L  A  G  A  D  L  V  H  T  M  S  T  P   249

1101  CGGAGTATGAGGTGAGAAGGATCTCGATCATATTCTTGGACAGTACGGGTATGTTATGTTGTATCTATCCTAAACTTCGGCAAGCTAACTGGTCTAGA   1200
      GCCTCATACTCCACTCTTCCTAGAGCTAGTATAAGAACCTGTCATGCCCATACAATACAACATAGATAGGATTTGAAGCGGGTTCGATTGACCAGATCT
 250  G  V  W  S  E  K  D  L  D  H  I  L  G  Q  Y  G                    (SEQ ID NO:32)  T   266

1201  CTTTCATCGTCGAGCGGAAGCGGACAGATATTGACGAGGCCATTGCAGCGCCATGGAGCCCGTAACGTCGGTACCTTTTCTATAGTACAATAAGTTGTTGAATAAGTTTT   1300
      GAAAGTAGCAGCTCGCCTTCGCCTGTCTATAACTGCTCCGGTACGTCGCGGTACCTCGGGCATTGCAGCCATGGAAAAGATATCATGTTATTCAACAACTTATTCAAA
 267  F  I  V  E  R  S  G  T  D  I  D  E  A  L  A  A  L  Q  P  W  K  K  N  I  H  V  I  Q  Q  L  I  Q  N   299

1301  TGACGTTAGCAGCACTAAGATTCGCTTATTCCTCAGGCGAGATATGAGCGTACGCTACTTGATCCCTGACCCGGTGATTGAGTACATCTATGAGAATAAC   1400
      ACTGCAATCGTCGTGATTCTAAGCGAATAAGGAGTCGCTCTATACTGCATGACTAGGACTGGGCCACTAACTCATGTAGATACTCTTATTG
 300  D  V  S  S  T  K  I  R  L  F  L  R  R  D  M  S  V  R  Y  L  I  P  D  P  V  I  E  Y  I  Y  E  N  N   332
```

FIG. 3C

1401 CTCTACTGACGACGGTACGACACAACCGACGGCCGACAAGGGCAAGACACGAGAGGAGCCCGCGCCCTTCAAATTAGCATTGCTCAAAAGCCAGATAA 1500
      GAGATGTACCTGCTGCCATGCTGTGTTGGCTGCCGGCTTGCCCGTCGTTCGTGCTCTCCTCCGGCCGCGAAGTTAATCGTAACGAGTTTTCGGTCTATT
 333  L  Y  M  D  D  G  T  T  Q  P  T  A  D  K  G  K  T  R  E  E  P  A  P  S  N  *                    357

1501 GGCCACGGCGACGACGTCATGACGACCATTGCTGTTTCACGAAGATATCAAACCGCGGCGAATGCAATCTCTGCGCTGATCTGAGCAAGCACTGATTC 1600
     CCGGTGCCGCTGCTGCAGTACTGCTGGTAACGACCAAAGTGCTTCTATAGTTTGGCGCCGCTTACGTTAGAGACGTTAGACTCGTTCGTGACTAAG

1601 CGGTAAGCCGCAAGTTGGGGGAGGATTTAATGAGCCCAACCTATGGTTTGTTCCGTCAAGTCACTGCGATTAACGACACGCCCTATGACTGTCATAT 1700
     GCCATTCGGCGTTCAACCCCCTCCTAAATTACTCGGGTTGGCATACCCGACTCAGTTCAGTTCAGTTCAGCCAGTTAATTGCTGTGCGAATACTGACAGTATA

1701 CGACAGGTCCCTCTCCAGAGCCGGCTCGGGCCGGATGTGTTGTCACTACGACCCGAAGAAGATAAGTTGGGGAGTTGGAGTTGTAGATTCACGTCGCCGCTTAAG 1792
     GCTGTGCCAGGGAGAGTCTCGGCCGGCCCGGATGTGTTGTCACTACGACCCGAAGAAGATAAGTTGTAGATTCACGTCGCCGCTTAAG

FIG. 3D (SEQ ID NO:10)

1   TTGCCTTCTTAGACTTGATATCTGAAGGAATATAACGGAAGAGATCATCTGGTTTGATGGTACTGTATTAGGCGGAGCACGTGATTATTTCCTCCGATA   100
    AACGGAAGAATCTGAACTATAGACTTCCTTATATTGCCTTCTCCTAGTAGACCAAACTACCATGACATAATGCCCCTCTGTGCACTAATAAAGGAGGCTAT
    (SEQ ID NO:12)

101 GGCCAGTGGCGTATGTCATATAAGGAAGAGACTGAGCCTGAGGGGAAAACACCTCCCGCCCGAGTTCCATCTTATCACTTTCACGCTCGATCTCTCCAAG   200
    CCGGTCACCGCATACAGTATTCCTTCTGACTCGGACGCCGAGCCGACCTCCCCTTTGTGAGGAGGGCGGGCTCAAGGTAGAATAGTGAAAGTGCGAGCTAGAGAGGTTC

201 TTTCTGGCTTCATTGACTGAGTCGCCTTGCCTAGTGGTAGATTAGATCTAGTGCAAATCACTTGCCTACATTCTGAACCTGTTGTTCAGCC   300
    AAGACCGAAGTAACTGACTCAGCAGCGGAACGGAACGCGATCACCATCTAAATCTAGATATCAGCGTTTAGTGAACGGATGTAAGAGCTTGGACAACAAGTCGG

301 TTGCGGGTTCCCCTACTACTTATCTCTTACCTTCTGAAAACACTTCCTCCTGCGGCCGAGACTAGTATCTATCGCCCTGTCGCCCACTTTC   400
    AACGCCAAGGGGAGGAGTGATGAATAGAAGATGGAAGATGGAAGATAGCGGAGACGCCGCTCTGATCATAGATAGCGGACAGCGGGTGAAAG

401 ACCACCGTGTTCACTAGGAGAATAGTGAAAGACTCAAGTCGTCTACCAAAATGTGGTCATGGTTCCGGTGGTGCGGCGGCCGCCGCAGAAGCGCAAGGAAGC   500
    TGGTGGCACAAAGTGATCCTCTTATCACTTTCTGAGTTCAGCAGATGTTTTACACCAGTACCAAGGCCACCGGCGTCTTCGGTTCTTCG

M W S W F R W C G R A E A Q G S   16
    (SEQ ID NO:11)

FIG. 4A

```
501  GCCGAAACGCAATCCTCCCAGCTTCGAAGCCACCTTGACATGCTACAGAAGCGAGAAAGCACCTAGAAAACCAAATGAACGAACAAGAGGCCATCGCTA
     CGGCTTTGCGTTAGGAGGGTCGAAGCTTCGGTGGAACTGTACGATGTCTTCGCTCTTTTCGTGATCTTTTGGTTACTTGCTTGTCTCCGGTAGGAT
17    A  E  N  A  I  L  Q  L  R  S  H  L  D  M  L  Q  K  R  E  K  H  L  E  N  Q  M  N  E  Q  E  A  I  A  K

601  AAAGAACGTGACCACGAATAAGAACGGTGTGTATATTATTGGACCTTTATACAAGTTCCCATGCTGATTTGACCACCCGCAGCCGCCAAGCCGGCG
     TTTCTTGCACTGGTGCTTATTCTTGCCACACATATAATAACCTGGAAATATGTTCAAGGGTACGACTAAACTGGTGGGCGTCGGCGGTTCGGCGCG
51    K  N  V  T  T  N  K  N  A                    (SEQ ID NO:33)  A  K  A  A  L

701  TCCGACGGAAAAAGGTGCACGAGAAGAACTTAGAACAGGCTCAGATTGTACAGCTTGAGCAGCAGATATACTCTATTGAAGCCGCAATATATTAA
     AGGCTGCCTTTTTCCACGTGCTCTTCTTGAATCTTGTCGAGTCTAACATGTCGAACTCGTCGTCTATATGAGATAACTTCGGCGGTTATAATT
65    R  R  K  K  V  H  E  K  N  L  E  Q  T  Q  A  Q  I  V  Q  L  E  Q  Q  I  Y  S  I  E  A  A  N  I  N

801  CCACGAGACCCTGGCCGCCATGAAGGCCGGTGCAGCTATGGAGAAGATTCACAACGGCATGACCGTCGAACAGTCGACGACGAGACAATGTACGTCCCT
     GGTGCTCTGGGACCGGCGGTACTTCCGGCCACGTCGATACCTCTTAAGTGTTGCCGTACTGGCAGCTTGTCAGCTGCTCTGTTACATGCAGGGA
98    H  E  T  L  A  A  M  K  A  A  G  A  A  M  E  K  I  H  N  G  M  T  V  E  Q  V  D  E  T  M

901  TACTGTACCGCTGGTGACATACCGGAATTGGCATGCTAACAGACTCAGGAGGACAAACTGCGGGAACAACAAGCCATCAACGACGAAATGCGATTGCCATC
     ATGACATGGCGACCACTGTATGGCCTTAACCGTACGATTGTCTGAGTCCTCCTGTTTGACGCCCTGTTGTTCGGTAGTTGCTTTAGGCGTAACGGTAG
128   D  K  L  R  E  Q  Q  A  I  N  D  E  I  A  I  A  I (SEQ ID NO:34)
```

FIG. 4B

```
1001  ACAAACCCGGGGTTCGGCGAGGTGACGAGCAGGAGAAGATCTGGAGGCGGAACTCGAGGCGCATGACGAGCAGGAGGCTATGACGAGCAGCCTCTCCACACAG   1100
      TGTTTGGGCGCCCAAGCCGCTCGTCCACCTGCTCTAGACCTCCGCCTTGAGCTCCGCTTGAGCTCCCGATACCTGCTCGTCCTCCGATACCTGCTCGTCCTCCGATACCTGCTCCGCTACGAGGTGTC

145   T  N  P  G  F  G  E  Q  V  D  E  E  D  L  E  A  E  L  E  G  M  E  Q  E  A  M  D  E  R  M  L  H  T  G     178

1101  GCACAGTACCAGTTGCAGATCAGTCGCCAGCGAATGCAGCTCCGCCAGCGAATGCAGAACGTAAGGCTCTCCCTTTCCCACCTCAAAAGCGAACTCCGACTGA   1200
      CGTGTCATGGTCAACGTCTAGTCGAGTTCGCCGATGACCGGAGCGGCTCGCTTGCATTCCGAGAGGGAAAGGGTGGAGTTTCGCTTGAGGCTGACT

179   T  V  P  V  A  D  Q  L  N  R  L  P  A  P  A  N  A  E  P                                                  197

1201  CAGCCTTCCAGCCGCCAAAGCGAAACAGAAGCAGAAGAAGACGAGGAAGCCGAGTTGGAGAAGTTACGCGCGAAATGGCCGAAATGTGAGAGTGGTCC   1300
      GTCGGAAGGTCGGCGGTTTCGCTTTGCTTCGTCTTCGTCTCGCTCTTCGGCTCAACCTCTTCAATGCGCGCCTTTACGGCTACACTCTCCACCAGG

198   A  K  A  K  Q  K  A  E  E  E  D  E  E  A  E  L  E  K  L  R  A  E  M  A  M  *                              222
(SEQ ID NO:35)

1301  TGGTGCTTTGGTCTCTTGTCTAACTTTAATCTTTTTCTCCCCCTACACATATGATGAACAGGGAATCGTTATCATGACGACTACGATTAGCCAAG   1400
      ACCACGAAACCAGAGAAACCAGATTGAAATTAGAAAAAGAGGGGATGTGTATACTACTTGTCCCTTAAGCAATAGTACTGCGTGATGCTAATCGGTTC

1401  CACTGTGTCTCTTTTTCCGTCGGCTCGTTGCGATTCCTCTCTCCGCGGCCGTAATTACTTATCTAGTGTACCAACTACCCCGCTGAGGTTCTCTTGAGG   1500
      GTGACACAAGAAAAAGGCAGCCGAGCAACCGAGCAATTAATGAATAGAATCAACATGTTGATGGGGCGCTCCGAAGACAACTCC
```

FIG. 4C

1501 CGAGAGCGAAGCCCAGAGACGTGTCGCCCCTTGCCCTGATTACTGGCCACTCCCGTTCTGTCTTCAGCGTGTATCCCACTCTG 1600
     GCTCTCGCTTTCGGGTCTGCACAGCGGGAACGGGACTAATGACCGGTGAGGCAGGCTCGTGCGATGAGGCAAGACAGGTGCGACACATAGGGTGAGAC

1601 TAATAATCTACCAAGTGAATACTTTTCTGGATGATTTGAAGGGCCTATGTTTCTACGCCATCATGTCATTAGATATGTTTGTGGATCATGTTTCCCCA 1700
     ATTATTAGATGGTTCACTTATGAAAAGACCTACTAAACTTCCCGGATACAAGGATGCGGTAGTACAGTATACAAAACACCTAGTACAAGGGT

1701 GCGCAATTGATGCCCATTTGCAGTTCACACTCGTGTCATATGAACCTCAGATATGAAAGCCGCTTCTCAACCAGCAAACGTCACTGAGGATTAAAT 1800
     CGGGTTAACTAACTACGGGTAAACGTCAAGTGTGAGCACAGTATACTTGGAGTCTTATACTTCCGGAAGAGTTGGGTCGTTTTGCAGTGACTCCTAATTTA

1801 TGAGTAATTGAGTAAAACTAAATTAGTAGTAGATAACTCCCGTTTCCCACCAGACCTAACACGTCAAACAGATAATCAACAAGGAAAAGAAGAAA 1899
     ACTCATTAACTCATTTTGATTTAATCAATCGATCTATTGAGGGCAAAGGGTGGTCTGGATTGTGGCAGGTTCTGGAATTGTCTATTAGTTGTTCCTTTCTTT

```
22401  CGATCCGTCAGTCGAAGTAGGAGGCTGCAATGCTGAATTTGATCAATGATATATACTAGACCCGTATATCTTGGAGAGGGCTACAGATGTAAACATC    22500
       GCTAGGCAGTCGACTTCATGCTCCCGACGTTACGACTTAAACTAGTTACTATATTATGATCTCCGATCTCCACATTGTAG
233    D  P  S  A  E  V  R  R  A  A  H  L  N  L  I  N  D  N  N  T  R  P  Y  I  L  E  R  A  R  D  V  N  I    265

22501  GTTAATAGAAGGCTCGTGATTCGAGAATTTGAAATCAATGAAGAAGTGTTTCATGATATTCAGCCGCATATTTTTGATTGATTCAGTGG          22600
       CAATTATCTTCCGAGCACTAAGCTCTTAAACTTAGTTACTTACACAAAGTACTACTAAACTAGTTAACTACTCACCC
266    V  N  R  R  L  V  Y  S  R  I  L  K  S  M  G  R  K  C  F  D  D  I  E  P  H  I  F  D  Q  L  I  E  N  G    299

22601  GTTTAGAAGATAGGAATTATCAGTGTGAAATGCGTGTAAGAGACTCATTGCTCATGATTGGTTAAATGCTCTGGATGGCGATTTGATAGAATTACTAGA    22700
       CAAATCTTCTATCCTTAATAGTCACTCTTCTGAGTACGACAATTACGAGACCTACCGCTAAACATCTTAATGATCT
300    L  E  D  R  E  L  S  V  R  N  A  C  K  R  L  I  A  H  D  W  L  N  A  L  D  G  D  L  I  E  L  L  E    332

22701  AAAATTGGATGTCTCAAGATCCTCAGTGTGTTAAGGCTATAGAAGCACTTTTTCAATCAGGCCAGATATATTATCTAAAATCAAATTTCCTGAAAGT    22800
       TTTTAACCTACAGAGTTCTAGGAGTCACACAATTCCGATATCTTCGTGAAAAAGTTAGTTCCGGTCTATATAGATTTAGT-TAAAGGACTTTCA
333    K  L  D  V  S  R  S  S  V  C  V  K  A  I  E  A  L  F  Q  S  R  P  D  I  L  S  K  I  K  F  P  E  S    365
```

```
23701  AAGGTAATGCATCATTATAAGTATATATTGCGTACAACTCATTGTAGATACATGGAACACTGTGGTACGGAACGAGAGGCAAAGTTGACT  23800
       TTCCATTACGTAGTAATTCATATATAAGCGAATGTTGAGTAACATCTATAAAAAGGCATGTACCCTGTGACACCATCTGCCTCTTCCGTTCAACTGA
666    K G N A S L K Y I A L Q V I V D I F S V H G N T V V D G E G K V D S                          699

23801  CAATCTCGTTGCACAAAATATTTTACAAGGTTTTAAAGAATAACGGTTTACGGAATGTCAGGTGATAGCAGCGGAGGGTTATGCAACTATTTTTGGC  23900
       GTTAGAGCAACGTGTTTTATAAAATGTTCCAAATATTCTTATTGCCAAATGCCTTACAGTCCACTATCGTCGCCTCCCAAATACGTTGATAAAACCG
700    I S L H K I F Y K V L K N N G L P E C Q V I A A E G L C F L F L A                            732

23901  AGACGTGTTCACTGATGATGATTTGTTTGAAACGTTGGTTTTGTCATATTTTTCGCCGATAAATTCCTCAACGAAGCGCTGGTACAGGCATTGCCTTC  24000
       TCTGCACAAGTGACTACTACTAAACAATTTGCAACCAAAACAGTATAAAAAGCGGCTATTTAAGGAGTTGCTTCGCGACCATGTCCGTAACGGAAG
733    D V F T D D D L F E T L V L S Y F S P I N S S N E A L V Q A F A F                            765

24001  TGCATTCCAGTCTATTGTTTTCACATCCTGCTCATCAACAACGTAGTCTAGGACGGCTGCGACACTACTCTTAGACTATGTGTTCTTTGGGACGATT  24100
       ACGTAAGGTCAGATAACAAAAGTGTAGGACGAGTAGTTGTTGCATCAGATCCTGCCGACGCTGTGATGAGAATTCTGATACACAAGAAACCTGCTAA
766    C I P V Y C F S H P A H Q Q R H S R T A A D I L L R L C V L M D D L                          799

24101  TACAGACTCTGTAATACCTGAAGTCGAAGCTAGCCGTGAAGCTGAAGTCGACTTGATCACGTAACTTAGT  24200
       ATGTCTGAGACATTATGGACTCATCTGGGCACTTCGATCAGATTTCGGATTGCGTTCAACGATAAAACCTGACTAAGTGCATTGAATCA
800    Q S S V I P E V D R E A M L K P N I F Q Q L L E H T D P R N L V                              832
```

FIG. 5H (SEQ ID NO:16)

1   TCTTTGGTGTCAATGGTGTATTATTCCGAGTTACTCCAGCTAGGTTCAGGAGTACCAAGAATGTACTTATTTATTATTATACACCGGACGAAGTCATAT
    AGAAACCACAGTTACCACATAATAAGGCTCAATGAGGTCCGATGAGTCCTTACATGGTTCTTACATGAAATAAATAAATATGTGGCCTCGTTCAGTATA (SEQ ID NO:18)

101 AATTACGCAAACGATTCGAAATTGTTAAAGCAGGATCAACGTATCTCATTTCTCTTTTGAAAGACGGGTAATAGAAAGTCTCTGAGTCGCACCCCACATG
    TTAATGCGTTTGCTAAGCTTTAACAATTTCGTCCTAGTTGCATAGAGTAAGAAAAACTTTCTGCCCATTATCTTTCAGAGACTCAGCGTGGGGTGTAC

201 GATATCGTACTATTCGTATATGGAATGTAAAATACTCGCAATACGATTTTATTTAGCTTCACAATCTCTCAACTTATCGTCTTGATCAATCTTTACGTT
    CTATAGCATGATAAGCATATACCTTACATTTTATGAGCGTTATGCTAAAATAAATCGAAGTGTTAGAAGTTTGAATAGCAGAACTAGTTAGAAATGCAA

301 TTACCAAATAATGCCCTGTTTCTGGCCATTTTTTGCTTATACCATCGCTTACCATACTCGCTGTCCATATGTGACGGGTCGTCTCCAAGAAAATAACAATG
    AATGGTTATTAGCGGACAAAGACCGGTAAAAACGAATATGGTAGATGTTATATAACGAATACACTGCCACAGCAGGTATACACTGGTCGTCCACATGGTATGTAC

401 TAAATTGACCCAGCGTGACGACAGTGACTGTAAGTTATATGTACAATCATCATCTACCTTAGTCACTGTTCCTCCACTGTTAAGTAGAGAAGAGAGAGA
    ATTAACTGGGTCGCACTGCTGTCATCTGACATTCAATATCATTTAGTATGATGAATCAGTGAAATCAGTGACAAGAGGTGACAATTCATCTCTCTCTCT

501 GTTTAAAGTGGAGAAGCAAGAAAAAGTGCACTTATTACGTAATGATCCACCACAAAGCACCGATTTTAAACCGCCACAGCACACCCGAATGAAGAACTACAAC
    CAAATTTCACCCTCCTTCCGTTCTTTTCACGTGAATAATACCTAGGGTGGTTTCGTGCCCTAAAATTGCCCGGTTCCGTTACTTGATGTG

M D P T K A P D F K P P Q P N E E L Q P    20
                                           (SEQ ID NO:17)

FIG. 6A

601 CACCGCCAGATCCAACACATACGATACCAAAATCTGGACCCATAGTTTTTAGCTGATTATAATTCTTCGATCGATGCTCCTTCAATCTGA 700
    GTGGCGGTCTAGTTGTGTATGCTATGGTTTAGACCTGGTATCAAGTATACAAAATCGACTAATATTAAGAAGCTAGCTACGAGGAAGTTAGAGCT
 21  P  P  D  P  T  H  T  I  P  K  S  G  P  I  V  P  Y  V  L  A  D  Y  N  S  S  I  D  A  P  P  N  L  D    53

701 CATTTACAAAACCCTGTCGTCAAGGAAAAAAAACGCCAACTCAAGCAACCATATTCCATTAAATACTAGTGACTTCCAGCCACTATCTCGG 800
    GTAAATGTTTTGGGACAGCAGTTCCTTTTTTTGCGGTTGAGTTCGTTGGCTTATGGTATAATTTATGATCATGAAGGTCGGTGATAGAGCC
 54  I  Y  K  T  L  S  S  R  K  K  N  A  N  S  S  N  R  M  D  H  I  P  L  N  T  S  D  F  Q  P  L  S  R    86

801 GATGTATCATCGGAGGAGGAAAGTGAAGGCAATGAATTGACGCTACTCTACAGGATGTTACGATGACTGGAATTTGGGGTACTGAAGAGCC 900
    CTACATAGTAGCCTCCTCCTTTCACTTCCGTTACTTAACTGCGATGAGATGTCCTACAATGCTACTGACCCTTAAACCCCATGACTTCTCGG
 87  D  V  S  S  E  E  E  S  E  G  Q  S  N  G  I  D  A  T  L  Q  D  V  T  M  T  G  N  L  G  V  L  K  S  Q  120

901 AAATTGCTGATTTGGAAGAAGTTCCTCACACAATTGTAAGACAAGCCAGAACTATTGAAGATTACGAATTTCCTGTACACAGATTGACGAAAAAGTTACA 1000
    TTTAACGACTAAACCTTCTTCAAGGAGTGTTTAACATTCTGTTCGGTCGATAACTTCTAATGCTTAAGGACATGTGTCTAACTGCTTTTCAATGT
121  I  A  D  L  E  E  V  P  H  T  I  V  R  Q  A  R  T  I  E  D  Y  E  F  P  V  H  R  L  T  K  K  L  Q  153

FIG. 6B

```
1001  AGATCCTGAAAACTGCCTCTGATCATGTGCTGTGATACATTTTCTCCATAACATACCTACATTTGAGAATGTTTAGATGATATC    1100
      TCTAGGACTTTTGACGGAGACTAGTAGCAACGACTAGTAAAGAGGTATTGTATGATGTAAACTCTTACAACTTTACCGAAATCTACTATAG
154   D  P  E  K  L  P  L  I  I  V  A  C  G  S  F  S  P  I  T  Y  L  H  L  R  M  F  E  M  A  L  D  D  I   186

1101  AATGAGCAAACGGTTTGAAGTGGTTGGTGGTTATATTTTCTCCAGTAAGTAATACTATGATAGTTTTCGCTCCCCAATCGGGGTCTCCCAATGGGGGT   1200
      TTACTCGTTTGCCAAACTTCACCAACCATCACCAATAAAAGAGGTCATTCACTATGATAGTTTCGCTCCCCAGCTTATCATCGTGTCCGCA
187   N  E  Q  T  R  F  E  V  V  G  G  Y  F  S  P  V  S  D  N  Y  Q  K  R  G  L  A  P  A  Y  H  R  V  R  M   220

1201  TGTGGAATTAGCATGCGAGCGGACATCATCTGGTTAATGGTTGATGCCTGGAATCTTACAATCAAGTTATACAAGGACAGCAAAGTCTTGGACCA   1300
      ACACGCTTAATCGTACGCTCGCCTGTAGTAGAACAATTACCAACTACGACCCTTAGAAATGTTAGTTCAATATGTTCCTCTGTTTCAGAACCTGT
221   C  E  L  A  C  E  R  T  S  S  W  L  M  V  D  A  W  E  S  L  Q  S  S  Y  T  R  T  A  K  V  L  D  H   253

1301  TTTCAATCATGAAATAAATCAAGAGAGGTGAATCATGACTGTAGATGGTGAAAAATGGGCGTAAAAATCATGTTATTGGCAGGCGGTGATCTTATC   1400
      AAAGTTAGTACTTTATTTATAGTTCTCTCCACTTAGACTGACATCTACCACTTTAGTACAATACCGCCACTACTAGAATAG
254   F  N  H  E  I  N  I  K  R  G  G  I  M  T  V  D  G  E  K  M  G  V  K  I  M  L  L  A  G  G  D  L  I   286

1401  GAATCCATGGGCGAGCCTCATGTGTGGCTGATTCAGACCTGCACCATATTTTGGTAATTATGATGTTTGATCGTGGAAAGGACTGGTTCTGATGTTA   1500
      CTTAGGTACCCGCTCGGAGTACACACCGACTAAGTCTGGACGTGGTATAAACCATTAATACTACAAACTAGCACCTTTCCTGACCAAGACTACAAT
287   E  S  M  G  E  P  H  V  W  A  D  S  D  L  H  H  I  L  G  N  Y  G  C  L  I  V  E  R  T  G  S  D  V  R   320
```

FIG. 6C

```
1501  GGTCCTTCTTGCTTCCCATGATATCATGTATGAACACAGAGAATATCCTTATTACAATGATATTTCCTCTACGAAAGTGCG   1600
      CCAGGAAGAACGAAAGGGTACTACTATAGTACATACTGTGTCTTCTTTATAGGAATACTTTGTTGATAAATGTACTAAGATGCTTTCAGC
 321    S  F  L  L  S  H  D  I  M  Y  E  H  R  R  N  I  L  I  K  Q  L  I  Y  N  D  I  S  S  T  K  V  R    353

1601  GCTTTTCATCAGACGCTGAATGTCAGTTCAAATATCTCTCCAACTCTGTCATCCGTTACATCCAAGAGTATAATCTATACATTAATCAAGTGAACCG   1700
      CGAAAAGTAGTCTGCACTTACAGTCAAGTTATATAGAAGAGGTTTGAGACAGTAGGCAATGTAGTTCTCATATTAGATATGTAATTAGTTTCACTTGGC
 354    L  F  I  R  R  G  M  S  V  Q  Y  L  L  P  N  S  V  I  R  Y  I  Q  E  Y  N  L  Y  I  N  Q  S  E  P    386

1701  GTCAAGCAGGTCTTGGATAGCAAAGAGTGAGTTTATTACAACTCTGATACTGCAGCAGTTCAAATTTACCACTTCCTCTTCAAGGTGCATAGAAAAAA   1800
      CAGTTCGTCCAGAACCTATCGTTTCTCACTCAAATAATGTTGAGACTATGACGTCGTCAAGTTAAATGTGAAAGGAAGTTCCACGTATCTTTTTT
 387    V  K  Q  V  L  D  S  K  E  *                                                                    395

1801  GTTCCTGAATGCACGATTTAAAATGTTTACAGCAGAGCAACAATCATGTGAACAATGTCAAACATTTATTTTAACACTTAATAATTATATATAACCACA   1900
      CAAGGACTTACGTGCTAAATTTTACAAATGTCGTCGTCGTTGTTACACTTGTTAGTACACTTGTTAAATAAATTGTGAATTATTAATTATATATTGGTGT

1901  CCAGCGGTAAGTTTCATAAGGAAAACCTTTCAGACAAACATTCCAGTGAATGTACGTAAATCAGCAAAATTAGCTTATAAATACAGAATCAGAATA   2000
      GGTCGCCATTCAAAGTATTCCTTTGGAAAGTCTGTTTGTAAGGTCACTTAGTCATTTGTCGTTTTAATCGAATGCATTTATGTCTTAGGCTTCT

2001  TACTTGATCTACTCGGCGTTACTATTAATGCGGGTAATGATCTATATATTGAATTTTGCACGTCTATAGTAACTTAAAAGTCTGTAATATTTGAAGTAACAA   2100
      ATGAACTAGAATGAGGCAATGATAATTACGCCCATTACTAATATAACTTAAAACGTGCAGATATCATTGAATTTTCAGAACATTATAAACTTCATTGTT

2101  TGCCGTATAATACTGCATATAGCCCTATCAATCGGAATATACCAAAACATCCTTT    2156
      ACGGCATATATTATGACGTATATCGGGATAGTTAGCCTTATATGGTTTTGTAGAAA
```

FIG. 6D (SEQ ID NO:19)
28401 GTTTGAATTGTGTTGTGTTAGAAATTGTGTGCTTTAATGTTATGTTATATGAAATCTTATTTAGATTTATTTAACGTTTTGCTGTGCTTATATAAA     28500
      CAAACTTAACACAACACAACAATCTTAAACACACGAATTACAACACGAAATTACTTTAGAATAATCTTAAATAATTGCAAAACGACACGAATATATTT (SEQ ID NO:21)
28501 CATTACATAATAAAGGAGTAGAGAGAAGTGGTAGAGAGAGTACAAATCTACCTGCCAGAACTCTCTCCTTATATATATATTTCCAGTGGTGTCTGATTA     28600
      GTAATGTATTATTTCCTCATCATCTCTTCACCATCATCTCTCTCATGTTTAGATGGAGACGGTCTTGAGAGAGGAATATATATAAGGTCACCACAGACCTAAT

28601 CCTACCTCAAGCCATACCATATCCATAAATCCATAAATTTCTACCCCAATCCAGCAGCTTCTATCACTATACTCGTATACCACCATA     28700
      GGATGGAGTTCGGTATGGTATAGGTATGGTATAGGTATATGGTATATGGTATATTTGCGGATGTTTAAAGATGGGGTTAGGTCGTCGAAGATAGTGATAGAGCATATGGTGTAT

28701 GGCACCACCACTGTTGTGTAAATTTACTCCTGAGGGGGGGGTGGCTCAACACGGTGTAGCCCTTCTTCCCGCACAATCGATGAAACCCACAATGCC     28800
      CCGTGGTGGTGACAAACACATTTAAATGAGGACTCCCCCCCCCACCGAGTTGTGCCACACGGTGTTAGGCTACTTTGGGGTGTTAGGGG

28801 TCCGTCTCTTCCACTGTGCACGGCGCTAGCTCAACATCTTCCCCGCACATTTACTGTGCAAAGAAGGTGCATAATCTAAAAAACATACGTATGAGAA     28900
      AGGCAGAGAAGGTGACACGTGCCCGCGATCGAGTTGTAGAAGGGGCGGGTGTAAATGACACCGTTCTCTTCCACGTATTAGATTTTTTGTATGCATACTCTT

28901 TGGAAAGGCAAGATAATATCGGACCCTAGTGAGTCACTTGCTTGTATTGCAACCAACTGCCGCCCCTCTTCCCGCTCTTGCACCAAAACGCTAAAT     29000
      ACCTTTCCCGTTCTATTATAGCCTGGCATCACTCAGTGAACGAAACCATAACGTTGGTTGAGGTGGAGAAGGGCGAAGCTGGTTTTGCGATTTA

FIG. 7A

```
29001  GCCCATTGTGATGGCTCATCCACCCTCAGACGACGAAGTAAGACCCGGGCACAAGAAATACGAGATCATAACAGTTCGAGTCCGTTTATTGTGTGCGTT  29100
       CGGGTAACACTACCGAGTAGGTGGAGTGCTGCTTCATTCTCGGGCCCCGGGCCCCGGTGTTCTCTAGTATTGTCAAGCTCAGCAAATAACACGCCAA

29101  TTGGTACGCTTTTTCGTGAGGTGTACTACCATTCATGAGAGTCGTTTTAGGAGCTGTCATGAAAGATATGTATCTTGTTGATGAACTGTAAAATTTGCA  29200
       AACCATGCGAAAAGCACTCCACATGATGGTAAGTACTCCTCGACAGTACTTCTATACATAGAACAACTACTGACATTTTTAAACGT

29201  GAAATTGCGCTATTCCGTTTATTCATTGTCGATTCGTGATTAGGGGTACAAATATACTAGAAGTTCTCCCCTGAGGATATAGGAATGCGCAA  29300
       CTTTAACGGCGATAAGGCAATAACAGCAATAACAGTAACAGTTTATATGATCTTCAAGAGGGAGCTCCTATATCCTTACGCGTT

29301  ATGGGCATTTGATGTGACACAAATTGGACAATATAACGATTCATTTTTAGATCGTGTTGTTCAACCGTGCCCAGTGGCCGAGTGGTTAAGGCGATGCCTGC  29400
       TACCCGTAAACTACACTGTGTTTTAAACCTGTTATATTGCTAAGTAAAAATCTAGCAACAAGTTGGCAGGGGTCACCGGCTCGCTACGGACG

29401  TATTTCCTCAGAAAGCAATTAGGCATTGGGTTTTTACCTGGCGCAGGTTCGAATCCTGTCTGTGACGCTTTTTTAATTTCTTACTCCATGACAAAGCG  29500
       ATAAGAGTCTTTTCGTTAATCCGTAACCCAAAATGGACGGGTCCAAGCTTAGGACAGACACTGCGAAAAAATTAAGAATGAGTACTGTTTTCGC
```

FIG. 7B

```
29501  GATAAAAATTCCCGCATTCGGCGTAAAAAATCCGTTTTTTTTTAGCACTCGCTGTTTTTGCCTCTGAAAAATGACGAAGACGGCTGG   29600
       CTATTTTTAAGGGCGTAAGCCGCATTTTTTAGGCGTAAAAAAAATCGTGAGCGACAAAAACGGAGATGGCCCACTTTTACTGCTACCC

29601  AATTGCGCTGCATCCGCTTACGCTAGGATAGAACACCTACAAGATTTACGAACTTTATGCTCGAAGATTCGTATCATATCTTTTAGTTTCCCCCA   29700
       TTAACGGACGTAGGCGAATGCGATCCTATCTGTGATGATGTTTCTAAATGCTGAAATAACGAGCTTCTAAGCGATAGTATAGAAAAATCAAAGGGGGT

29701  TTTCACAATGGGATACCGTTGTTTTTCTGTAGTACGCTTTCTCATAGTTAATAGAGTCAGTAATTCATTTCATTTTTGCAGAAAGGAATTCCTTCAC   29800
       AAAGTGTTACCCTATGGCAACAAAAAGACATTCATGCGAAAGTATCATGCAGTATCAATTATCTCAGTCATTAAGTAAAAAACGTCTTTCCTTAAGAAGTG

29801  CTAATTTAGAATTTCATCAACATTTATTGTATCTGCATGGTATAACAAATTAGAAAAATTTGGAAGGGAAAAAAAAACTGTTGCGTCAATTACTTATACC   29900
       GATTAAATCTTAAAGTAGTTGTAAATAACATAGACGTACCATATGTTTAATCTTGTTAATCTTTTAAACCTTCCCTTTTTTTTTTGACAACGCAGTAATGAATATGG

29901  AGGGATAGAAAAAAAAAGGAAACATGGAAATCGATTCCTTCGAGACGAGGAATTGATTCCTCCACCCGACCCGAA   30000
       TCCCTATCTTTTTTTTTTTTTCCTTGTACCTAGGGTGTTCTCGAAGGCGTAAGTTGGCGTAGACGTCTGTCCTTAACTAAGGAGGTGGGCTGGGCCTT

1      M  D  P  T  R  A  P  D  F  K  P  P  S  A  D  E  E  L  I  P  P  P  D  P  E   25
```

(SEQ ID NO:20)

FIG. 7C

```
30001  TCTAAAATCCCAAATCTATTATTCCAATTATTCCATACGTCTCTTAGCCGATGGAATCCTCTATAGATGCACCTTTTAATATTAAGAGGAAGAAAAAGCATC  30100
       AGATTTTAAGGGTTTAGATAATAAGGTTAATAGGTATGGCTACGCCTAAGGAGATATCTACGTGGAAAATTATATCTCCTTCTTTTCGTAG
  26     S  K  I  P  K  S  I  P  I  I  P  Y  V  L  A  D  A  N  S  S  I  D  A  P  F  N  I  K  R  K  K  H  P         59

30101  CTAAGCATCATCATCACCATCATCACAGTCGTAAAGAAGCAATGATAAAAACATCAGTATTCCATTGAACCAAGACGACTTTCAACCACTTTCCGC  30200
       GATTCGTAGTAGTAGTGGTAGTAGTGTCAGCATTTCTCCGTTACTATTTTTGTAGTCGTATAAGTAACTTGGTCTGCTGAAAGTTGGTGAAAGGCG
  60     K  H  H  H  H  H  H  S  R  K  E  G  N  D  K  K  H  Q  H  I  P  L  N  Q  D  D  F  Q  P  L  S  A           92

30201  AGAAGTGTCTTCCGAAGATGATGACGCGGATTTTAGATCGGTTCAGATTCAACCACAGAATCAGAAACTAGAGGTGTTCAGAAATAT  30300
       TCTTCACAGAAGGCTTCTACTACTGCGCCTAAAATCTAGCCAAGTCTAAGTTGGTGTCTTAGTCTTTGATCTCCACAGTCTTTATA
  93     E  V  S  S  E  D  D  D  A  D  F  R  S  K  E  R  Y  G  S  D  T  T  E  S  E  T  R  G  V  Q  K  Y          125

30301  CAGATTGCTGATTAGAAGAAGTTCCACATGGAATCGTTCGTCAAGCAAGATCGTTCTGAAGACTACGAATTCCCCTACACAGATTATCGAAAAATTAC  30400
       GTCTAACGACTAATCTTCTTCAAGGTGTACCTTAGCAAGCAGTTCGTTCTGGAACCTTCTGATGCTTAAGGGGATGTGTCTAATAGCTTTTTAATG
 126     Q  I  A  D  L  E  E  V  P  H  G  I  V  R  Q  A  R  T  L  E  D  Y  E  P  P  S  H  R  L  S  K  K  L  L     159

30401  TGGATCCAAATAAACTGCCGTTAGTAATAGTAGCATGTGGGTCTTTTCACCAATCACCTACTTGCATCTAAGAATGTTGAAATGCTTTAGATGCAAT  30500
       ACCTAGGTTTATTTGACGGCAATCATTATCATCGTACACCCAGAAAAAGTGGTTAGTGATGAACTAGAATCTTACAAACTTTACGAAATCACGTTA
 160     D  P  N  K  L  P  L  V  I  V  A  C  G  S  F  S  P  I  T  Y  L  H  L  R  M  F  E  M  A  L  D  A  I    192
```

FIG. 7D

```
30501  CTCTGAACAAACAAGGTTTGAAGTCATAGGTGGATATATTACTCCCGTGTTAGTGATAACTATCAAAGCAAGGCTTGGCCCCATCCTACCATAGAGTACGT    30600
       GAGACTTGTTTGTTCCAAACTTCAGTATCCACCTATATAATGAGGGACAATCACTATTGATAGTTTTCGTTCCGAACGGGTAGGATGGTATCTCATGCA
 193   S  E  Q  T  R  F  E  V  I  G  G  Y  Y  S  P  V  S  D  N  Y  Q  K  Q  G  L  A  P  S  Y  H  R  V  R     225

30601  ATGTGTGAATTGGCCTGCGAAAGAACCTCATCTTGTTGATGGTGATGCATTGGAGTCATTGCAACCTTCATACACAAGAACTGCCAAGTCTTGGATC        30700
       TACACACTTAACCGACGCTTTCTTGGAGTAGAACAACTACCACTACGTAACCTCAGTAACGTTGGAAGTATGTGTTCTTGACGGTTCCAGAACCTAG
 226   M  C  E  L  A  C  E  R  T  S  S  W  L  M  V  D  A  W  E  S  L  Q  P  S  Y  T  R  T  A  K  V  L  D  H  259

30701  ATTTCAATCACGAAATCAATATTAAGAGAGGTGGTGCTACTGTTACTGGAGAAAAATTGGTGTGCTGGCTGGTGACCTAAT                        30800
       TAAAGTTAGTGCTTTAGTTATAATTCTCTCCACCACGATGACAATGACCTCTTTTTAACCACACTTTTATTACAACGACCGACCACACTGGATTA
 260   F  N  H  E  I  N  I  K  R  G  G  V  A  T  V  T  G  E  K  I  G  V  K  I  M  L  L  A  G  G  D  L  I     292

30801  AGAGTCAATGGGTGAACCAACGTTTGGGCGAGCGCGATTTACATCACATTCTCGGTAATTACGGTTGTTGTTGATTGTCGAACGTACTGTTCTGATGTA    30900
       TCTCAGTTACCCACTTGGTTGCAAACCGTTCGGCGCGGGCCTAAATGTAAGACCCATTAATGCCAACAATAACAGCTTGCATGACCAAGACTACAT
 293   E  S  M  G  E  P  N  V  W  A  D  A  D  L  H  H  H  I  L  G  N  Y  G  C  L  I  V  E  R  T  G  S  D  V  325
```

FIG. 7E

```
30901  AGGTCTTTTTGTTATCCATGATATATGTATGAACATAGAAGGAATATTCTATCAAGCAACTCATCTATAATGATATTTCTTCCACGAAAGTTC  31000
       TCCAGAAAAAACATAGGTACTATATAACATACTTGTATCTTCCTATAAGATAGTTCGTTGAGTAGTATATTACTATAAGAAGGTGCTTTCAAG
326    R  S  F  L  L  S  H  D  I  M  Y  E  H  R  R  N  I  L  I  I  K  Q  L  I  Y  N  D  I  S  S  T  K  V  R     359

31001  GTCTATTATCAGACGGCGCCATGTCTGTACATATTTGTTACCTAATTCGGTCTCATCAGTAGTATATCCAAGAACATAGACTATATGTGACTATATGTG  31100
       CAGATAAATAGTCTGCGCGGTACAGACATGTTATAAACAATGATTAAGCCAGTAGTCCATATAGTTCTTGTATCGATACACCTGGTTTGGCTTGG
360    L  F  I  R  R  A  M  S  V  Q  Y  L  L  P  N  S  V  I  R  Y  I  Q  E  H  R  L  Y  V  D  Q  T  E  P     392

31101  TGTTAAGCAAGTTCTTGGAAACAAGAATGATTGCCGTCCGAATTGCTTCGTTCTTCTTCATCTTCTCTTACAATTTCCAATTTCCCTACAG  31200
       ACAATTCGTTCAAGAACCTTTGTTCTTACTAACGGCAGGCCTTAACGAAGCAAGAAAGTAGAAGAAAGTTAAAGGTTAAAGGGGATGTC
393    V  K  Q  V  L  G  N  K  E  *                                                                       401

31201  GAATTAATTGGAGGGTACAAGCGAGTAGAAATGTGACATAGTACTACCTATCTGTGTTAGTATAGTTTTTTTCTGTAGTATAATTCACTTTTACA  31300
       CTTAATTAACCTCCCATGTTCGCTCATCGCTCATCTTTACACTGTATACTGAATGATACTCAAAAAAAAGACATCATATTAGTGAAAATGT

31301  CTAATTTTTTCGCCTTTTTCTCTTAAGAGACTAATTTCTATAACCTTCAGCGGTTATACCAAATATAAAAATGAAGGAAACAAACAGTAAGAATAA  31400
       GATTAAAAAGCCGAAAAAGAGAATTTCTCGATTTAAGATATTGAAGTCGCCAATAATGTTTATATTTTTTACCTTCCTTTGTTTGTCATTCTTTATT

31401  GCGCAACAGCACGCGTTAGTTCACCATTGGAATTCCAACATTTCAAATTTAATCTAATGGCAAGAGATATCACATTTTGACCGTATTTTAGAAAGTGTG  31500
       CGCGTTGTCGTGCGCAATCAAGTGGTAACCTAAGGTTGTAAAGTTTTAAATTAGAATTACCGGTTCTATAGTGTAAAAACTGCATAAAAATCTTCAACAC
```

FIG. 7F

31501 GCGCTGTAAATAATGATGAGGCAGGAAAATTGTTATCTGCTTGAGACTTCAACCGTACCGACTTCAATTCATTATATAT
CGGCGACAATTTATTACTACTCCGTCCTCCTTTAACAATAGAACCGAACCTGAAGTTGGCATGCGTAACTCCCTGCCTTAGTGGCTGAGATTAAGTAATATATA 31600

31601 TCCACTGCTACCACCTGGAATGTTGAAAGTATGTTTCTCCTAGCAAAATTAAAACCCATCCGTGAATGAAGCGTTACTAACTATATAATAACTGGTAGCTTT
AGGTGACGATGGTGGACCTTACAACTTTCATACAAAGAGGATCGTTTTAATTTGGGTAGGCACTTACTTCGCAATGAATTATTGACCATCGAAA 31700

31701 GTCACTCGTACCAGGAGGAAAAGTGAAGATTAAACTGAATTTTAAA 31743
CAGTGAGGCATGGTCCTTTTCACTTCTAAATTTGACTTAAAATTT

FIG. 7G

(SEQ ID NO:22)

15901 TTCTACTACTCCACGTACAAAAAGAGCACGCTGCTTATTATACTCTGTTTGTGCCACAAGAATGATCAACATCAACATAATATCAATAGTATCTGCAA 16000
AAGATGATGAGGTGCATGTTTTCTCGTGCAGACGAAATAAATATGAAACACGGTGTCTTACTAGTGTGTATTTATAGTGTATCATAGACGTT (SEQ ID NO:24)

16001 CACATCTGCTCCACGGAACTAAACCCGTTGGGAGCAGTGCCCCGTTGAGCAACTGTCATTTGGGCAACTGTCATTTGATAAGCGTTTAACCTAATTGTCGGTGTAACAGCCAAGCAAGATT 16100
GTGTAGACGAGGTGCCTTGATTGGAGCAACTGTCTGTCAACAGCAACTGTCATTTGATAAGCGTTTAACCTAATTGTCGGTTTTTGTGGTTCGTTCTAA

16101 CACGAAACCGCGCCTGCCCGAAGGCCCATTTAACGCCGAAGGCCCATTTAACGCCGGAGGCAAGATCGGCGAGCAAACCACTCCCCAGGACCAGCACAT 16200
GTGCTTTGCCGGAGCAAACCTGGGGCTTCCGGGTAAATTGCCGAAGGCCCATTTAACGCCGGAGGCAAACCACTCCCCAGGACCAGCACAT

16201 CACTGCACGAGCAACAATAACTGAACATGCGACTAGAACATGCGAGATAGGCGAGGATACCTTCTGTGATCCTGCAGGGATCAACGCAGCTGAAG 16300
GTGACGTCGTCGTTATTGATCTGTACCGTTCCTATGGAGACACTAGGACGTCCTATGGAGACACTAGGACGTCGTGTAGTGTCCGACCTCCCGGACCTTC

16301 AAGATGGTTACCTCAGGACGACGAGGACACGTCACTCAGCAACGTCGAGCTGCCAGATGCACAGGTCAATGGGAAGAGTCGTCGCAACAGTTGAAACAAGCTGCT 16400
TTCTACCAATGGCTTTCCTGTGCAGTGAGTCGTTGCCAGTTACCCTTCTCAGGACGGTGTCAACTTGTTCGACGA

16401 CAACTGGGTCCTGCCCCTGCTGGGCAAGTATATAGTGTAGGAGAATGGCCAAGACTCTATGAGTAGGTTCATTGAACACTTTGTATAAGTGTTGTT 16500
GTTCACCCAGGACGACGGAGACAACCACCCGTTCATATATCCATCCTCCTCTTACCGGTTCTGAGATACCTCATTCAAGTAACTTGTGAAACATATTCACAACAA

FIG. 8A

```
16501  GTTTATGTATCCGCATATAGCAGTATAAACAGATAAATGGCACTTTTCGCACACCCGTTGTTTATCTCCGATAGTACGTGGGCCTTTATTTATGGTCGT  16600
       CAAATACATAGGCGTATATCAATATGTCTATTATTGTCTATTTACCGTGGGCAACAAATAGAGGCTATCATGCACCCGGAAATAAATACCAGCA

16601  TTAACGAAAGAACGGCATCTTGAATTGAGCAGTATTTAAAGATAGGACCAGCACCATCTGTGTCGAAAAAAGTAGCAAGAGAAAAG                16700
       AATTGCTTCTTGCCGTAGAACTAACTCGTCCGTCCTTGTCTGTCGTACTAGACACAGCTTTTTCATCGTTCTTTTC

16701  TAGGAGGATAGGATGAACAGGAAAGTAGCTATGTAACGGGTACTAATAGTAATCTTGGTCTGAACATTGTGTTCCGTCTGATTGAACTGAGGACACCA       16800
       ATCCTCCTATCCTACTTGTCCTTTCATGATAGCATTGCCCATGATTATCATTAGAACAAGGCAGACTAACTTGACTCCTGTGGT
           M  N  R  K  V  A  I  V  T  G  T  N  S  N  L  G  L  N  I  V  F  R  L  I  E  T  E  D  T  N  30
        1                                                                                  (SEQ ID NO:23)

16801  ATGTCAGATTGACCATTGTGGTGACTTCTAGAACGCTTCTGAGTGCAGGAGTGATTAACCAGATAAGATTTTACACAAATCAGGCCCGTGTAGA       16900
       TACAGTCTAACTGGTAACACCACTGAAGATCTTGCGAAGACTCACGTCCTCCACTAATTGGTCTAATTTCTAAAATGTTGTTTAGTCCGGCACATCT
           V  R  L  T  I  V  V  T  S  R  T  L  P  R  V  Q  E  V  I  N  Q  I  K  D  F  Y  N  K  G  R  V  E   63
       31
```

ESSENTIAL FUNGAL GENES AND THEIR USE

RELATED APPLICATION INFORMATION

This application is a divisional of application Ser. No. 08/965,762 filed Nov. 7, 1997, now U.S. Pat. No. 6,280,963, which is incorporated herein by reference in its entirety.

BACKGROUND OF THE INVENTION

The invention relates to essential fungal genes and their use in identifying antifungal agents.

Fungal infections (mycoses) may be cutaneous, subcutaneous, or systemic. Superficial mycoses include tinea capitis, tinea corporis, tinea pedis, perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis (phycomycosis), paracoccidioidomycosis, North American blastomycosis, histoplasmosis, coccidioidomycosis, and sporotrichosis. Fungal infections can also contribute to meningitis and pulmonary or respiratory tract diseases. Opportunistic fungal infections proliferate, especially in patients afflicted with AIDS or other diseases that compromise the immune system.

Examples of pathogenic fungi include dermatophytes (e.g., *Microsporum canis* and other M. spp.; and Trichophyton spp. such as *T. rubrum*, and *T. mentagrophytes*), yeasts (e.g., *Candida albicans, C. Tropicalis*, or other Candida species), *Torulopsis glabrata, Epidermophyton floccosum, Malassezia furfur* (*Pityropsporon orbiculare*, or *P. ovale*), *Cryptococcus neoformans, Aspergillus fumigatus*, and other Aspergillus sp., Zygomycetes (e.g., Rhizopus, Mucor), *Paracoccidioides brasiliensis, Blastomyces dermatitides, Histoplasma capsulatum, Coccidioides immitis*, and *Sporothrix schenckii.*

Various strains of the fungus Aspergillus sp. cause aspergillosis, a potentially life-threatening disease in humans and other mammals. The clinical manifestations of aspergillosis in humans are very similar to those observed in rodents and cows. For example, necrosis, angioinvasion, and hematogenous dissemination are common features of aspergillosis in rodent and bovine model systems and in humans. In humans, aspergillosis typically is caused by inhalation of conidia (i.e., asexual spores produced by the fungus). In cattle, pathogenic Aspergillus typically enter the animal through the forestomach and then disseminate through the blood of the animal. Putative virulence factors produced by pathogenic species of Aspergillus include hydroxymate siderophores (i.e., compounds that compete with human iron-binding proteins to acquire iron to support fungal growth), lipids having the ability to inhibit complement and phagocytosis, and proteinases that can degrade elastin and other substrates.

SUMMARY OF THE INVENTION

The invention is based on the discovery of four new genes in the fungus *Aspergillus nidulans* that are essential for survival. These genes are referred to herein as AN97, AN80, AN17, and AN85; for convenience, the polypeptides encoded by these genes are referred to herein as "AN polypeptides." The genes encoding the AN polypeptides are useful molecular tools for identifying similar genes in pathogenic microorganisms, such as pathogenic strains of Aspergillus (e.g. *Aspergillus fumigatus* and *Aspergillus flavus*). In addition, the AN polypeptides and the essential genes encoding them are useful targets for identifying compounds that are inhibitors of the pathogens in which the AN polypeptides are expressed. Such inhibitors inhibit fungal growth by being fungistatic (e.g., inhibiting reproduction or cell division) or by being fungicidal (i.e., by causing cell death).

The invention, therefore, features an isolated AN97 polypeptide having the amino acid sequence set forth as partial sequences in SEQ ID NOs 2 and 29, or conservative variations thereof. Nucleic acids encoding AN97 also are included within the invention. In particular, the invention includes an isolated nucleic acid of (a) SEQ ID NO:1, as depicted in FIG. 1, or degenerate variants thereof; (b) SEQ ID NO:1, or degenerate variants thereof, wherein T is replaced by U; (c) nucleic acids complementary to (a) and (b); and (d) fragments of (a), (b), and (c) that are at least 15 base pairs in length and that hybridize under stringent conditions to genomic DNA encoding the polypeptide as partial sequences in SEQ ID NOs 2 and 29.

The invention also features an isolated AN80 polypeptide having the amino acid sequence set forth in SEQ ID NO:5, or conservative variations thereof. Nucleic acids encoding AN80 also are included. In particular, the invention includes an isolated nucleic acid of: (a) SEQ ID NO:4, as depicted in FIG. 2, or degenerate variants thereof; (b) SEQ ID NO:4, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide of SEQ ID NO:5.

The invention also includes an isolated AN85 polypeptide having: the amino acid sequence set forth as partial sequences in SEQ ID NOs:8, 30, 31, and 32, or conservative variations thereof. Nucleic acids encoding AN85 also are included. In particular, the invention includes an isolated nucleic acid of: (a) SEQ ID NO:7, as depicted in FIG. 3, or degenerate variants thereof; (b) SEQ ID NO:7, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide set forth as partial sequences in SEQ ID NOs:8, 30, 31, and 32.

The invention also features an isolated AN17 polypeptide having the amino acid sequence set forth as partial sequences in SEQ ID NOs:11, 33, 34, and 35, or conservative variations thereof. Nucleic acids encoding AN17 also are included. In particular, the invention includes an isolated nucleic acid of: (a) SEQ ID NO:10, as depicted in FIG. 4, or degenerate variants thereof, (b) SEQ ID NO:10, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide set forth as partial sequences in SEQ ID NOs:11, 3.3, 34, and 35.

The invention also includes isolated nucleic acids that are at least 15 base pairs in length and which hybridize under stringent conditions to a nucleotide sequence selected from the group consisting of SEQ ID NO:1, SEQ ID NO:4, SEQ ID NO:7, and SEQ ID NO:10. In addition, the invention includes allelic variants (i.e., genes encoding isozymes) of the genes encoding AN97, AN17, AN80, and AN85. For example, the invention includes genes that encode an AN polypeptide but which gene includes point mutation, deletion, promoter variant, or splice site variant, provided that the resulting AN polypeptide functions as an AN polypeptide (e.g., as determined in a complementation assay, as described herein and elsewhere). Also included within the invention are isolated nucleic acid molecules containing the cDNA sequences contained with ATCC accession numbers 209473, 209472, 209484, and 209471, as well as polypeptides encoded by the cDNA sequences of these nucleic acid molecules.

Identification of the AN97, AN17, AN80, and AN85 genes and the determination that they are essential allows homologs of these genes to be found in other organisms (e.g., fungi, such as yeast like *S. cerevisiae*; mammalian cells, such as human or murine cells; or plant cells). Thus, the AN polypeptides used not only can be as a model for identifying similar essential genes in other Aspergillus strains, but also to identify homologous essential genes in other organisms, e.g., *S. cerevisiae*. Because such genes are homologs, they can be expected to be essential for survival without the need for extensive characterization of the homologous gene or polypeptide. Even though some such homologous genes may have previously been identified, the invention allows one to determine that such genes are essential for survival. Having identified such homologous genes as essential, these genes and the polypeptides encoded by these genes can be used to identify compounds that inhibit the growth of the host organism (e.g., compounds that are fungicidal or fungistatic against pathogenic strains of the organism).

As used herein, the term "yeast" refers to organisms of the order Saccharomycetales, which includes yeast such as Saccharomyces and Candida. As described-below, several homologs of the AN polypeptides have been identified in the yeast *S. cerevisiae* and are essential for survival. Given the identification of such genes as essential in *S. cerevisiae*, homologs of these essential yeast genes can also be found in pathogenic yeast strains (e.g., *Candida albicans*). The *S. cerevisiae* polypeptide and gene termed D9798.4 are homologs of the AN97 polypeptide and gene. The D9798.4 polypeptide and nucleic acid are depicted in FIG. 5, and are set forth in SEQ ID NOs:14 and 13, respectively (GenBank Accession No. U32517). As described herein, various methods of the invention can utilize the D9798.4 polypeptide or conservative variations thereof. Also useful are isolated nucleic acids of (a) SEQ ID NO:13, as depicted in FIG. 5, or degenerate variants thereof; (b) SEQ ID NO:13, or degenerate variants thereof, wherein T is replaced by U; (c) nucleic acids complementary to (a) and (b); and (d) fragments of (a), (b), and (c) that are at least 15 base pairs in length and which hybridize under stringent conditions to genomic DNA encoding the polypeptide of SEQ ID NO: 14.

Yeast homologs of the AN85 and AN80 polypeptides and genes also have been identified as being essential for survival, and these homologs can be used in the methods described herein. As described above for AN97, conservative variations, degenerate variants, complementary sequences, fragments, and nucleic acids in which T is replaced by U also can be used in various methods of the invention. Two homologs of AN85 have been identified. The amino acid and nucleic acid sequences of the AN85 homolog termed YGR010W are depicted in FIG. 6 (GenBank Accession No. Z72795); these sequences are set forth as SEQ ID NOs:17 and 16, respectively. The amino acid and nucleic acid sequences of the AN85 homolog termed L8543.16 are depicted in FIG. 7 (GenBank Accession No. U20618); these sequences are set forth as SEQ ID NOs:20 and 19, respectively. The AN80 polypeptide and gene have a homolog in yeast, termed L8004.2, the amino acid and nucleic acid sequences of which are depicted in FIG. 8 (GenBank Accession No. U53876). These sequences are set forth as SEQ ID NOs:23 and 22, respectively.

The term AN97 polypeptide or gene as used herein is intended to include the polypeptide and gene set forth in FIG. 1 herein, as well as homologs of the sequences set forth in FIG. 1. For example, encompassed by the term AN97 gene are degenerate variants of the nucleic acid sequence set forth in FIG. 1. (SEQ ID NO:1). Degenerate variants of a nucleic acid sequence exist because of the degeneracy of the amino acid code; thus, those sequences that vary from the sequence represented by SEQ ID NO:1, but which nonetheless encode an AN97 polypeptide are included within the invention. Likewise, because of the similarity in the structures of amino acids, conservative variations can be made in the amino acid sequence of the AN97 polypeptide while retaining the function of the polypeptide (e.g., as determined in a complementation assay, as described herein and elsewhere). AN97 polypeptides and genes identified in additional Aspergillus strains may be such conservative variations or degenerate variants of the particular AN97 polypeptide and nucleic acid set forth in FIG. 1 (SEQ ID NOs:2 and 29; and 1, respectively). The AN97 polypeptide and gene share at least 80%, e.g., 90%, sequence identity with SEQ ID NOs: 2 and 29; and 1, respectively. Regardless of the percent sequence identity between the AN97 sequence and the sequence represented by SEQ ID NOs:1 and 2, the AN97 genes and polypeptides encompassed by the invention are able to complement for the lack of AN97 function (e.g., in a temperature-sensitive mutant) in a standard complementation assay. AN97 genes that are identified and cloned from additional Aspergillus strains, and pathogenic strains in particular, can be used to produce AN97 polypeptides for use in the various methods described herein, e.g., for identifying antifungal agents. Likewise, the term AN80 encompasses homologues and conservative and degenerate variants of the sequences depicted in FIG. 2. Such homologues, conservative variations, and degenerate variants of AN17, AN85, and AN80 also are included within the invention. Excluded from the invention are the naturally-occurring homologs of AN polypeptides and nucleic acids found in *S. cerevisiae* (D9798.4, L8543.16, YGR010W, and L8004.2), although methods employing such polypeptides and nucleic acids are encompassed by the invention.

The AN97, AN17, AN80, and AN85 genes have been identified and shown to be essential for survival, these AN polypeptides and their yeast homologs (e.g., D9798.4, L8543.16, YGR010W, and L8004.2) can be used to identify antifungal agents. More specifically, these AN polypeptides and their yeast homologs can be used, separately or together, in assays to identify test compounds which bind these polypeptides. Such test compounds are expected to be antifungal agents, in contrast to compounds that do not bind AN97, AN17, AN80, AN85, D9798.4, L8543.16, YGR010W, and/or L8004.2. As described herein, any of a variety of art-known methods can be used to assay for binding of test compounds to the polypeptides. The invention includes, for example, a method for identifying an antifungal or anti-yeast agent where the method entails: (a) contacting an AN polypeptide, or homolog thereof, with a test compound; (b) detecting binding of the test compound to the AN polypeptide or homolog; and (c) determining whether a test compound that binds the AN polypeptide or homolog inhibits growth of fungi or yeast, relative to growth of fungi or yeast cultured in the absence of the test compound that binds the AN polypeptide or homolog, as an indication that the test compound is an antifungal or anti-yeast agent.

In various embodiments, the AN polypeptide is derived from a non-pathogenic or pathogenic Aspergillus strain, such as *Aspergillus nidulans, Aspergillus fumigatus, Aspergillus flavus*, and *Aspergillus niger*. Preferably, homologs thereof are derived from the yeast *Saccharomyces cerevisiae*. The test compound can be immobilized on a substrate, and binding of the test compound to the AN polypeptide or homolog can be detected as immobilization of the AN polypeptide or homolog on the immobilized test compound, e.g., in an immunoassay with an antibody that specifically binds AN97.

If desired, the test compound can be a test polypeptide (e.g., a polypeptide having a random or predetermined amino acid sequence; or a naturally-occurring or synthetic polypeptide). Alternatively, the test compound can be a nucleic acid, such as a DNA or RNA molecule. In addition, small organic molecules can be tested. The test compound can be a naturally-occurring compound or it can be synthetically produced, if desired. Synthetic libraries, chemical libraries, and the like can be screened to identify compounds that bind the AN polypeptides. More generally, binding of test compound to the AN polypeptide or homolog can be detected either in vitro or in vivo. Regardless of the source of the test compound, the AN polypeptides described herein can be used to identify compounds that are fungicidal or fungistatic to a variety of pathogenic or non-pathogenic strains.

In an exemplary method, binding of a test compound to an AN polypeptide can be detected in a conventional two-hybrid system for detecting protein/protein interactions (e.g., in yeast or mammalian cells). Generally, in such a method, (a) the AN polypeptide is provided as a fusion protein that includes the AN polypeptide fused to (i) a transcription activation domain of a transcription factor or (ii) a DNA-binding domain of a transcription factor; (b) the test polypeptide is provided as a fusion protein that includes the test polypeptide fused to (i) a transcription activation domain of a transcription factor or (ii) a DNA-binding domain of a transcription factor; and (c) binding of the test polypeptide to the AN polypeptide polypeptide is detected as reconstitution of a transcription factor. The yeast homologs can be used in similar methods. Reconstitution of the transcription factor can be detected, for example, by detecting transcription of a gene that is operably linked to a DNA sequence bound by the DNA-binding domain of the reconstituted transcription factor (See, for example, White, 1996, Proc. Natl. Acad. Sci. 93:10001–10003 and references cited therein and Vidal et al., 1996, Proc. Natl. Acad. Sci. 93:10315–10320).

In an alternative method, an isolated nucleic acid molecule encoding an AN polypeptides is used to identify a compound that decreases the expression of the AN polypeptide in vivo. Such compounds can be used as antifungal agents. To discover such compounds, cells that express an AN polypeptide are cultured, exposed to a test compound (or a mixture of test compounds), and the level of expression or activity is compared with the level of AN polypeptide expression or activity in cells that are otherwise identical but that have not been exposed to the test compound(s). Many standard quantitative assays of gene expression can be utilized in this aspect of the invention.

In order to identify compounds that modulate expression of an AN polypeptide (or homologous sequence), the test compound(s) can be added at varying concentrations to the culture medium of cells that express an AN polypeptide (or homolog), as described above. Such test compounds can include small molecules (typically, non-protein, non-polysaccharide chemical entities), polypeptides, and nucleic acids. The expression of the AN polypeptide is then measured, for example, by Northern blot PCR analysis or RNAse protection analyses using a nucleic acid molecule of the invention as a probe. The level of expression in the presence of the test molecule, compared with the level of expression in its absence, will indicate whether or not the test molecule alters the expression of the AN polypeptide. Because the AN polypeptides are essential for survival, test compounds that inhibit the expression and/or function of the AN polypeptide will inhibit growth of the cells or kill the cells.

Compounds that modulate the expression of the polypeptides of the invention can be identified by carrying out the assay described above and then measuring the levels of the AN polypeptides expressed in the cells, e.g., by performing a Western blot analysis using antibodies that bind an AN polypeptide.

The invention further features methods of identifying from a large group of mutants those strains that have conditional lethal mutations. In general, the gene and corresponding gene product are subsequently identified, although the strains themselves can be used in screening or diagnostic assays. The mechanism(s) of action for the identified genes and gene products provide a rational basis for the design of anti-fungal therapeutic agents. These antifungal agents reduce the action of the gene product in a wild type strain, and therefore are useful in treating a subject with that type, or a similarly susceptible type of infection by administering the agent to the subject in a pharmaceutically effective amount. Reduction in the action of the gene product includes competitive inhibition of the gene product for the active site of an enzyme or receptor; non-competitive inhibition; disrupting an intracellular cascade path which requires the gene product; binding to the gene product itself, before or after post-translational processing; and acting as a gene product mimetic, thereby down-regulating the activity. Therapeutic agents include monoclonal antibodies raised against the gene product.

Furthermore, the presence of the gene sequence in certain cells (e.g., a pathogenic fungus of the same genus or similar species), and the absence or divergence of the sequence in host cells can be determined, if desired. Therapeutic agents directed toward genes or gene: products that are not present in the host have several advantages, including fewer side effects, and lower overall dosage.

The invention includes pharmaceutical formulations that include a pharmaceutically acceptable excipient and an antifungal agent identified using the methods described herein. In particular, the invention includes pharmaceutical formulations that contain antifungal agents that inhibit the growth of, or kill, pathogenic Aspergillus strains. Such pharmaceutical formulations can be used for treating an Aspergillus infection in an organism. Such a method entails administering to the organism a therapeutically effective amount of the pharmaceutical formulation. In particular, such pharmaceutical formulations can be used to treat aspergillosis in mammals such as humans and domesticated mammals (e.g., cows and pigs). The efficacy of such antifungal agents in humans can be estimated in an animal model system well known to those of skill in the art (e.g., bovine and rodent (e.g., mouse) model systems). These formulations also can be used to treat fungal infections in plants, e.g., by topically applying the antifungal agent to the plant. Alternatively, where the antifungal agent is a polypeptide or an antisense RNA, a gene encoding the polypeptide or expressing the antisense RNA can be transfected into the plant, using conventional techniques, and the polypeptide or antisense RNA can be expressed in the plant.

Also included within the invention are polyclonal and monoclonal antibodies that specifically bind AN97, AN17, AN80, or AN85 polypeptide. Such antibodies can facilitate detection of AN polypeptides in various Aspergillus strains. These antibodies also are useful for detecting binding of a test compound to AN97, AN17, AN80, or AN85 polypeptides (e.g., using the assays described herein). In addition, monoclonal antibodies that bind AN97, AN17, AN80, or AN85 polypeptide are themselves adequate antifungal agents when administered to a mammal, as such monoclonal antibodies are expected to impede one or more functions of AN97, AN17, AN80, or AN85 polypeptide.

As used herein, "nucleic acids" encompass both RNA and DNA, including cDNA, genomic DNA, and synthetic (e.g., chemically synthesized) DNA. The nucleic acid may be double-stranded or single-stranded. Where single-stranded, the nucleic acid may be a sense strand or an antisense strand. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide sequence. The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

A nucleic acid sequence that is "substantially identical" to an AN97, AN17, AN80, or AN85 nucleotide sequence is at least 80% or 85% identical to the nucleotide sequence of the Aspergillus AN97, AN80, AN85, and AN17 nucleic acids of SEQ ID NO:1, NO:4, NO:7, and NO:10, respectively, as depicted in FIGS. 1, 2, 3, and 4, respectively. For purposes of comparison of nucleic acids, the length of the reference nucleic acid sequence will generally be at least 40 nucleotides, e.g., at least 60 nucleotides or more nucleotides. Sequence identity can be measured using sequence analysis software (e.g., Sequence Analysis Software Package of the Genetics Computer Group, University of Wisconsin Biotechnology Center, 1710 University Avenue, Madison, Wis. 53705).

The AN polypeptides of the invention include, but are not limited to, recombinant polypeptides and natural polypeptides. The invention also encompasses nucleic acid sequences that encode forms of AN97, AN17, AN80, or AN85 polypeptides in which naturally occurring amino acid sequences are altered or deleted. Preferred nucleic acids encode polypeptides that are soluble under normal physiological conditions. Also within the invention are nucleic acids encoding fusion proteins in which a portion of AN97, AN17, AN80, or AN85 is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells. The invention also includes isolated, for example, polypeptides (and the nucleic acids that encode these polypeptides) that include a first portion and a second portion; the first portion includes, e.g., an AN polypeptide, and the second portion includes an immunoglobulin constant (Fc) region or a detectable marker.

The fusion partner can be, for example, a polypeptide which facilitates secretion, e.g., a secretory sequence. Such a fused polypeptide is typically referred to as a preprotein. The secretory sequence can be cleaved by the host cell to form the mature protein. Also within the invention are nucleic acids that encode AN97, AN17, AN80, or AN85 fused to a polypeptide sequence to produce an inactive preprotein. Preproteins can be converted into the active form of the protein by removal of the inactivating sequence.

The invention also includes nucleic acids that hybridize, e.g., under stringent hybridization conditions (as defined herein) to all or a portion of the nucleotide sequence of SEQ ID NO:1, NO:4, NO:7, or NO:10, or their complements. The hybridizing portion of the hybridizing nucleic acids is typically at least 15 (e.g., 20, 30, or 50) nucleotides in length. The hybridizing portion of the hybridizing nucleic acid is at least 80%, e.g., at least 95%, or at least 98%, identical to the sequence of a portion or all of a nucleic acid encoding an AN97, AN17, AN80, or AN85 polypeptide. Hybridizing nucleic acids of the type described herein can be used as a cloning probe, a primer (e.g., a PCR primer), or a diagnostic probe. Nucleic acids that hybridize to the nucleotide sequences of SEQ ID NO:1, NO:4, NO:7, or NO:10 are considered "antisense oligonucleotides." Also included within the invention are ribozymes that inhibit the function of AN97, AN17, AN80, or AN85, as determined, for example, in a complementation assay.

In another embodiment, the invention features cells, e.g., transformed host cells, that contain a nucleic acid encompassed by the invention. A "transformed cell" is a cell into which (or into an ancestor of which) has been introduced, by means of recombinant DNA techniques, a nucleic acid encoding an AN polypeptide. Both prokaryotic and eukaryotic cells are included, e.g., bacteria, Aspergillus, yeast, and the like.

The invention also features genetic constructs (e.g., vectors and plasmids) that include a nucleic acid of the invention which is operably linked to a transcription and/or translation sequence to enable expression, e.g., expression vectors. By "operably linked" is meant that a selected nucleic acid, e.g., a DNA molecule encoding an AN polypeptide, is positioned adjacent to one or more sequence elements, e.g., a promoter, which directs transcription and/or translation of the sequence such that the sequence elements can control transcription and/or translation of the selected nucleic acid.

The invention also features purified or isolated AN97, AN17, AN80, and AN85 polypeptides. As used herein, both "protein" and "polypeptide" mean any chain of amino acids, regardless of length-or post-translational modification (e.g., glycosylation or phosphorylation). Thus, the terms "AN97 polypeptide" (or AN97), "AN17 polypeptide" (or AN17), "AN80 polypeptide" (or AN80), or "AN85 polypeptide" (or AN85) include full-length, naturally occurring AN97, AN17, AN80, or AN85 proteins, respectively, as well as recombinantly or synthetically produced polypeptides that correspond to a full-length, naturally occurring AN97, AN17, AN80, or AN85 protein, or to a portion of a naturally occurring or synthetic AN97, AN17, AN80, or AN85 polypeptide.

A "purified" or "isolated" compound is a composition that is at least 60% by weight the compound of interest, e.g., an AN97 polypeptide or antibody. Preferably the preparation is at least 75% (e.g., at least 90% or 99%) by weight the compound of interest. Purity can be measured by any appropriate standard method, e.g., column chromatography, polyacrylamide gel electrophoresis, or HPLC analysis.

Preferred AN97, AN17, AN80, AN85 polypeptides include a sequence substantially identical to all or a portion of a naturally occurring AN97, AN17, AN80, or AN85 polypeptide, e.g., including all or a portion of the sequences shown in FIGS. 1, 2, 3, and 4, respectively. Polypeptides "substantially identical" to the AN polypeptide sequences described herein have an amino acid sequence that is at least 80% or 85% (e.g., 90%, 95% or 99%) identical to the amino acid sequence of the AN97, AN80, AN85 or AN17 polypeptides of SEQ ID NOs:2 and 29; NO:5; NOs:8, 30, 31, and 32; and NOs:11, 33, 34, and 35, respectively. For purposes of comparison, the length of the reference AN polypeptide sequence will generally be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. It also might be a 100 amino acid long polypeptide which is 50% identical to the reference polypeptide over its entire length. Of course, other polypeptides also will meet the same criteria.

The invention also features purified or isolated antibodies that specifically bind to an AN polypeptide. By "specifically binds" is meant that an antibody recognizes and binds a particular antigen, e.g., an AN97, AN17 polypeptide, but does not substantially recognize and bind other molecules in a sample, e.g., a biological sample that naturally includes AN97, AN17, AN80, or AN85. In one embodiment the antibody is a monoclonal antibody.

In another aspect, the invention features a method for detecting an AN polypeptide in a sample. This method includes: obtaining a sample suspected of containing AN97, AN17, AN85, or AN80; contacting the sample with an antibody that specifically binds an AN97, AN17, AN85 or AN80 polypeptide under conditions that allow the formation of complexes of an antibody and AN97, AN17, AN85 or AN80; and detecting the complexes, if any, as an indication of the presence of AN97, AN17, AN85 or AN80 in the sample.

Also encompassed by the invention is a method of obtaining a gene related to (i.e., a functional homologue of) the AN97, AN17, AN85, or AN80 gene. Such a method entails obtaining a labeled probe that includes an isolated nucleic acid which encodes all or a portion of AN97, AN17, AN85, or AN80, or a homolog thereof (e.g., D9798.4, L8543.16, YGR010W, or L8004.2); screening a nucleic acid fragment library with the labeled probe under conditions that allow hybridization of the probe to nucleic acid fragments in the library, thereby forming nucleic acid duplexes; isolating labeled duplexes, if any; and preparing a full-length gene sequence from the nucleic acid fragments in any labeled duplex to obtain a gene related to the AN97, AN17, AN85, or AN80 gene.

The invention offers several advantages. By combining gene knockout assays, as described herein, with assays of conditional sensitivity, we have identified genes that are truly essential, i.e., genes whose absence is fungicidal to Aspergillus. In addition, the methods for identifying antifungal agents can be configured for high throughput screening of numerous candidate antifungal agents.

Other features and advantages of the invention will be apparent from the following detailed description, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

BRIEF DESCRIPTION OF THE DRAWINGS

Figure 1G:
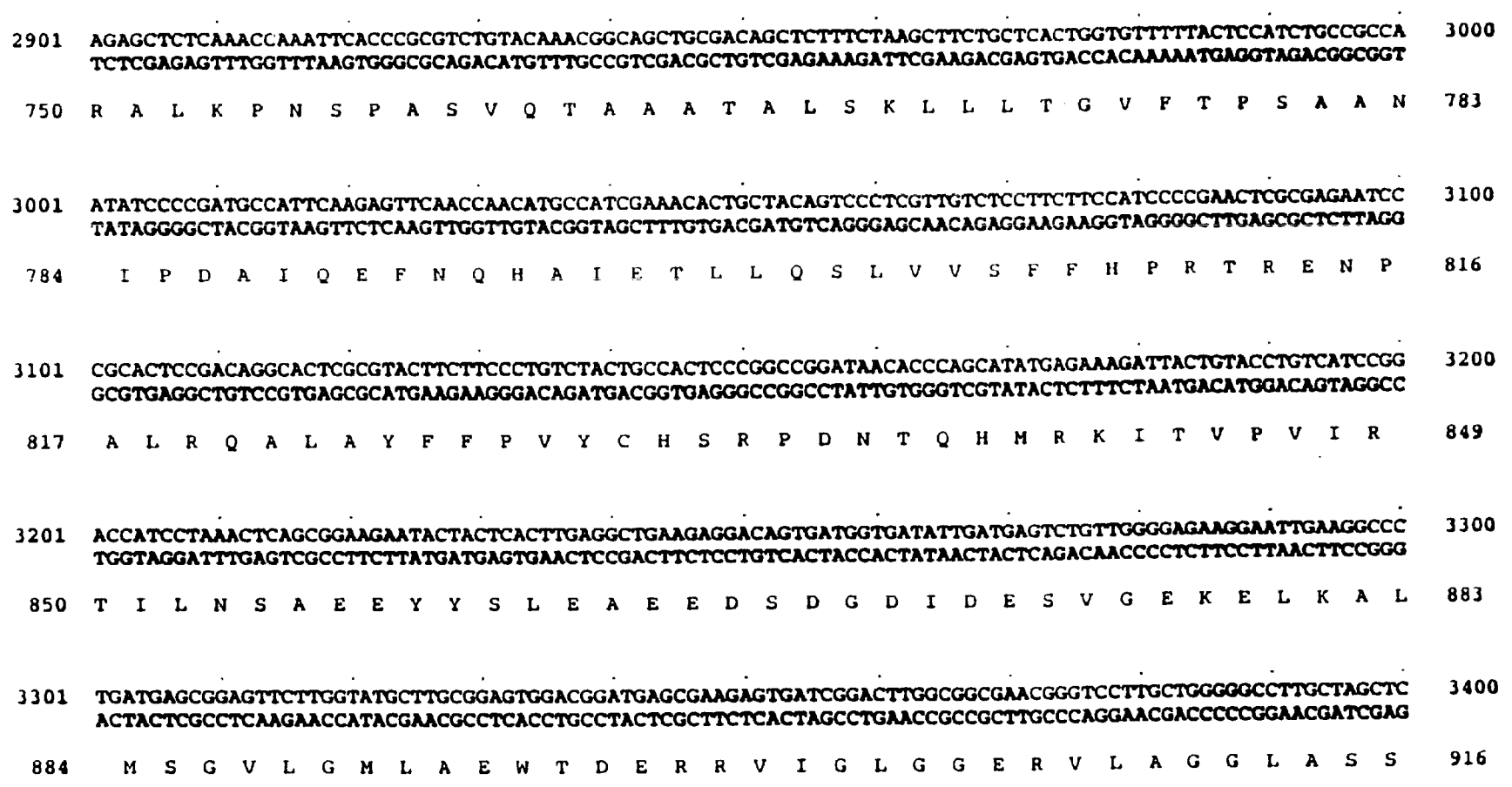

FIGS. 1A to 1K are a representation of the amino acid and nucleic acid sequences of the AN97 polypeptide and gene from an *Aspergillus nidulans* strain (SEQ ID NOs:2 and 29 and NO:1, respectively). The non-coding sequence is set forth as SEQ ID NO:3.

FIGS. 2A to 2D are a representation of the amino acid and nucleic acid sequences of the AN80 polypeptide and gene from an *Aspergillus niduland* strain (SEQ ID NOs:5 and 4, respectively). The non-coding sequence is set forth as SEQ ID NO:6.

FIGS. 3A to 3D are a representation of the amino acid and nucleic acid sequences of the AN85 polypeptide and gene from an *Aspergillus niduland* strain (SEQ ID NOs:8, 30, 31 and 32; and NO:7, respectively). The non-coding sequence is set forth as SEQ ID NO:9.

FIGS. 4A to 4D are a representation of the amino acid and nucleic acid sequences of the AN17 polypeptide and gene from an *Aspergillus niduland* strain (SEQ ID NOs:11, 33, 34, and 35; and NO:10, respectively). The non-coding sequence is set forth as SEQ ID NO:12.

Figure 5A:
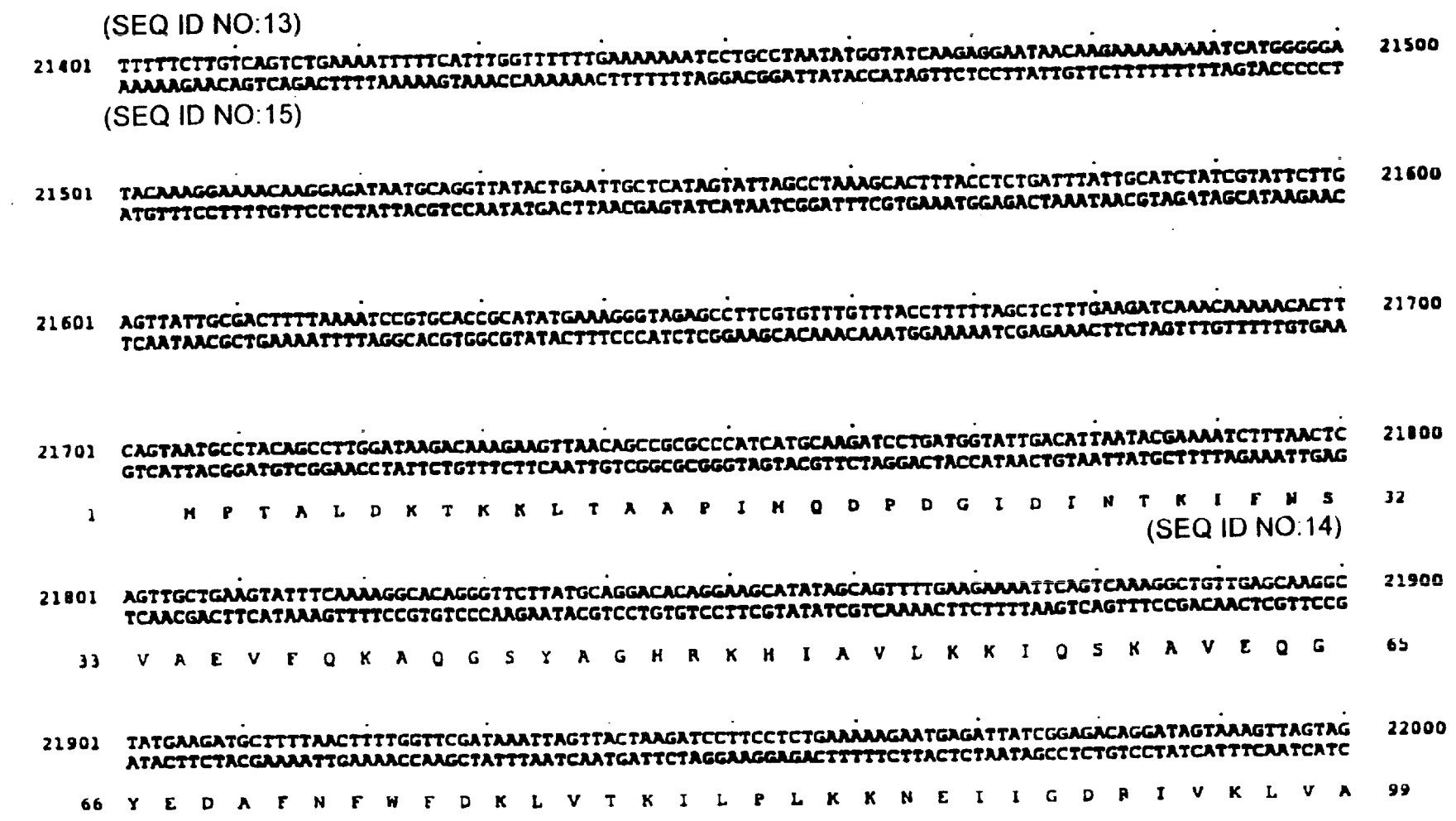
Figure 5B:
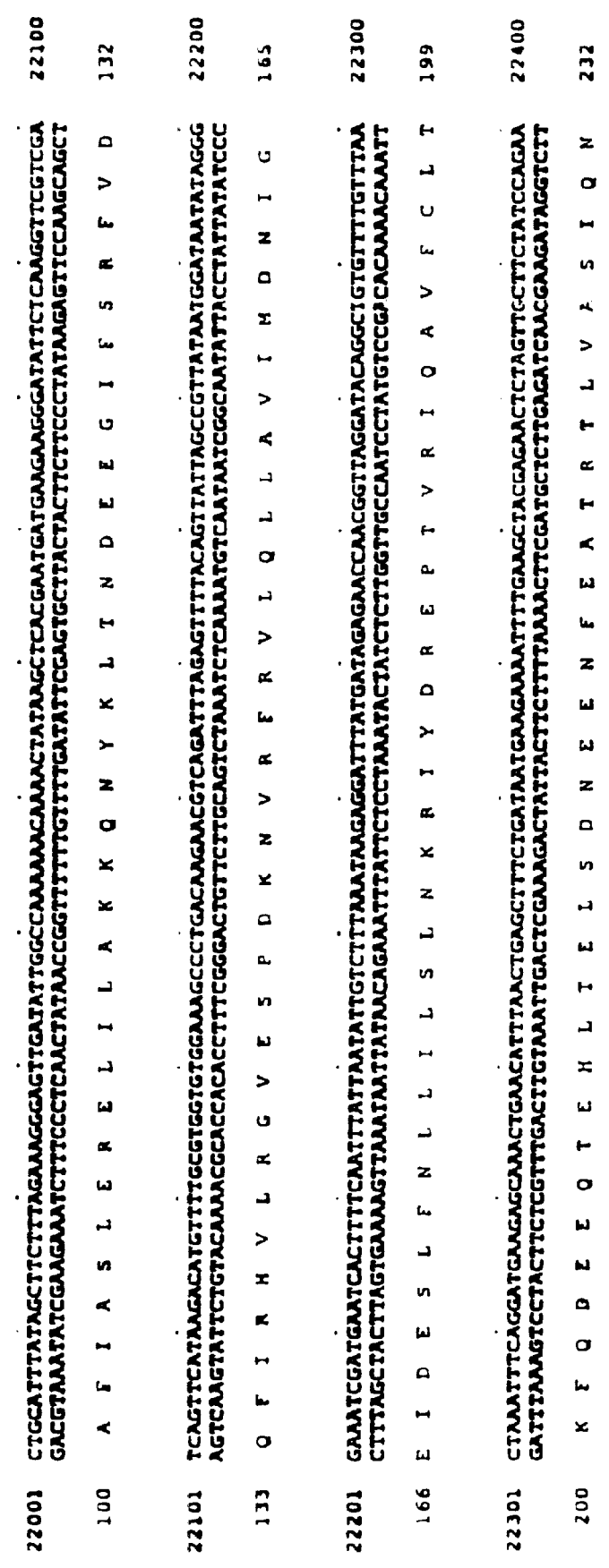
Figure 5D:
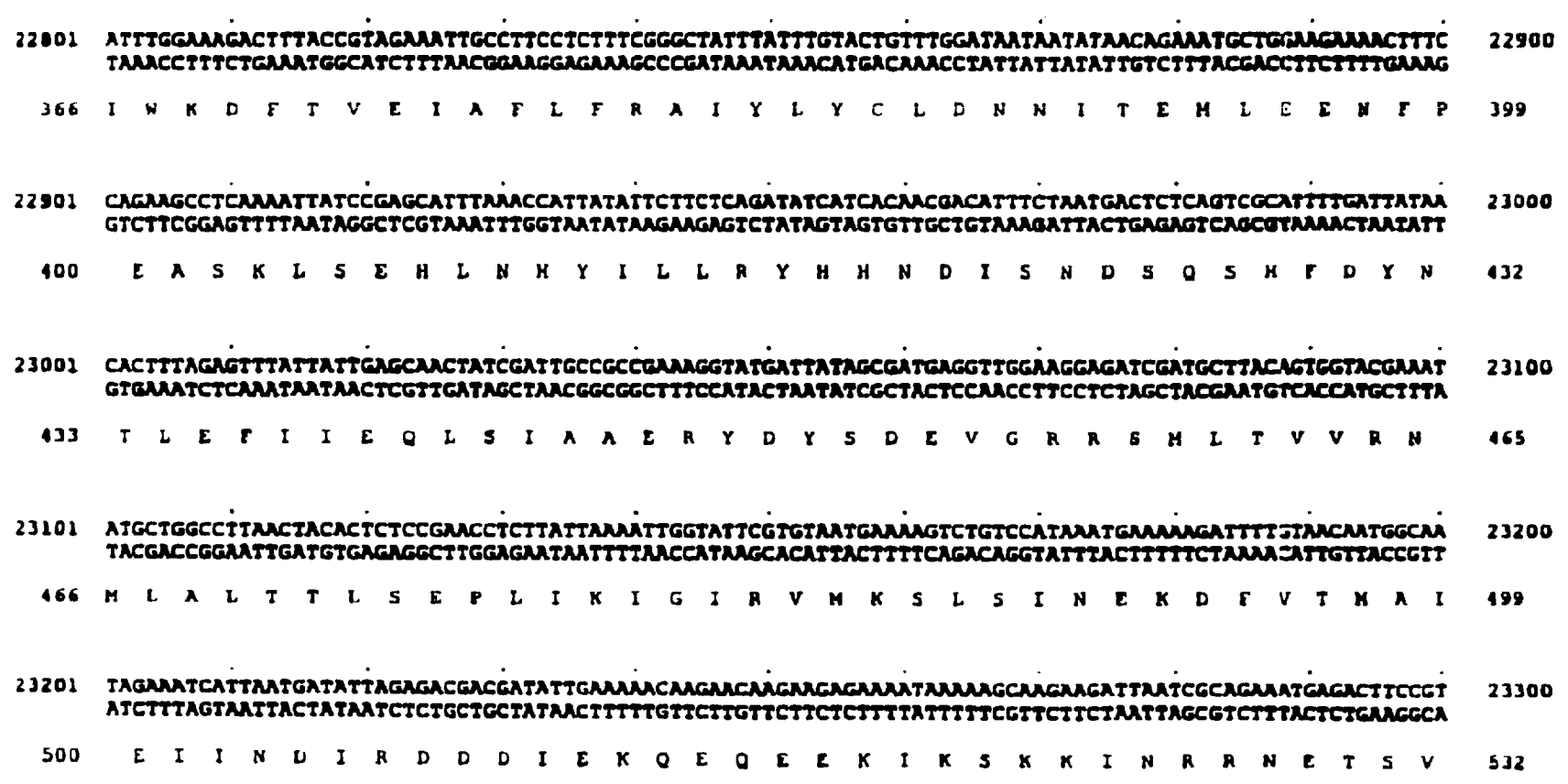
Figure 5E:
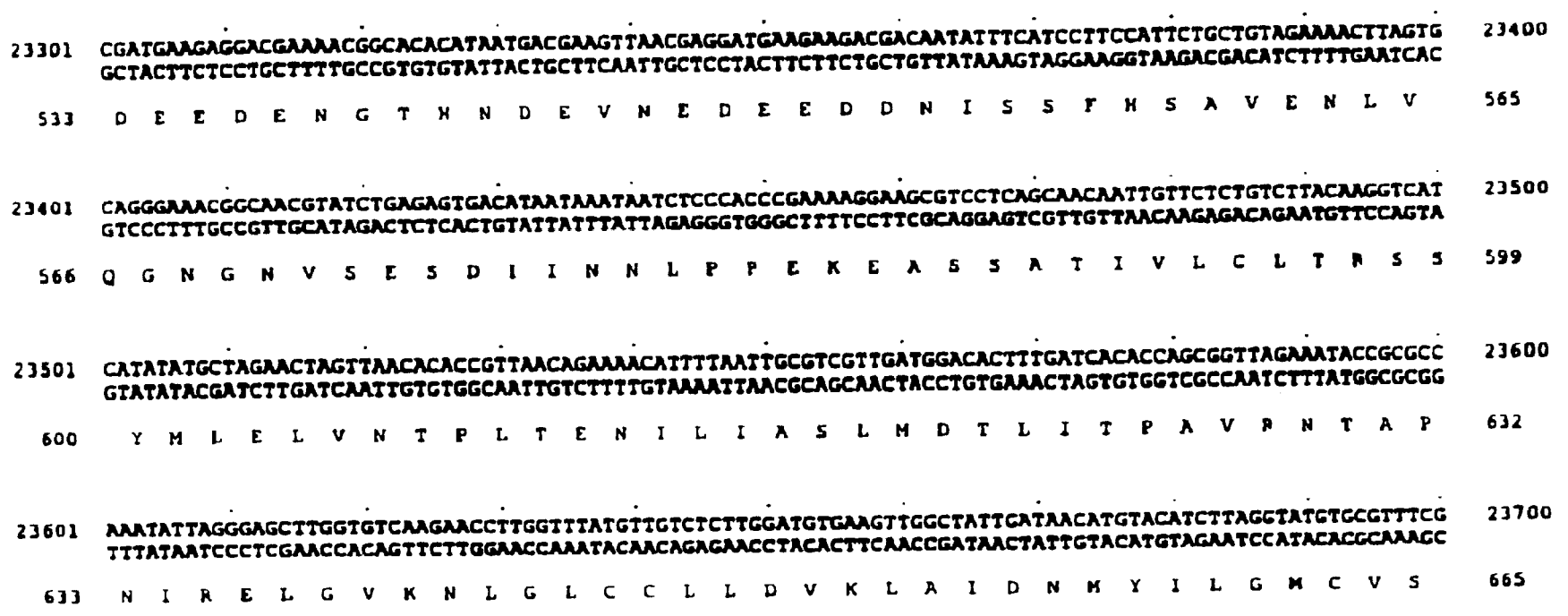
Figure 5G:
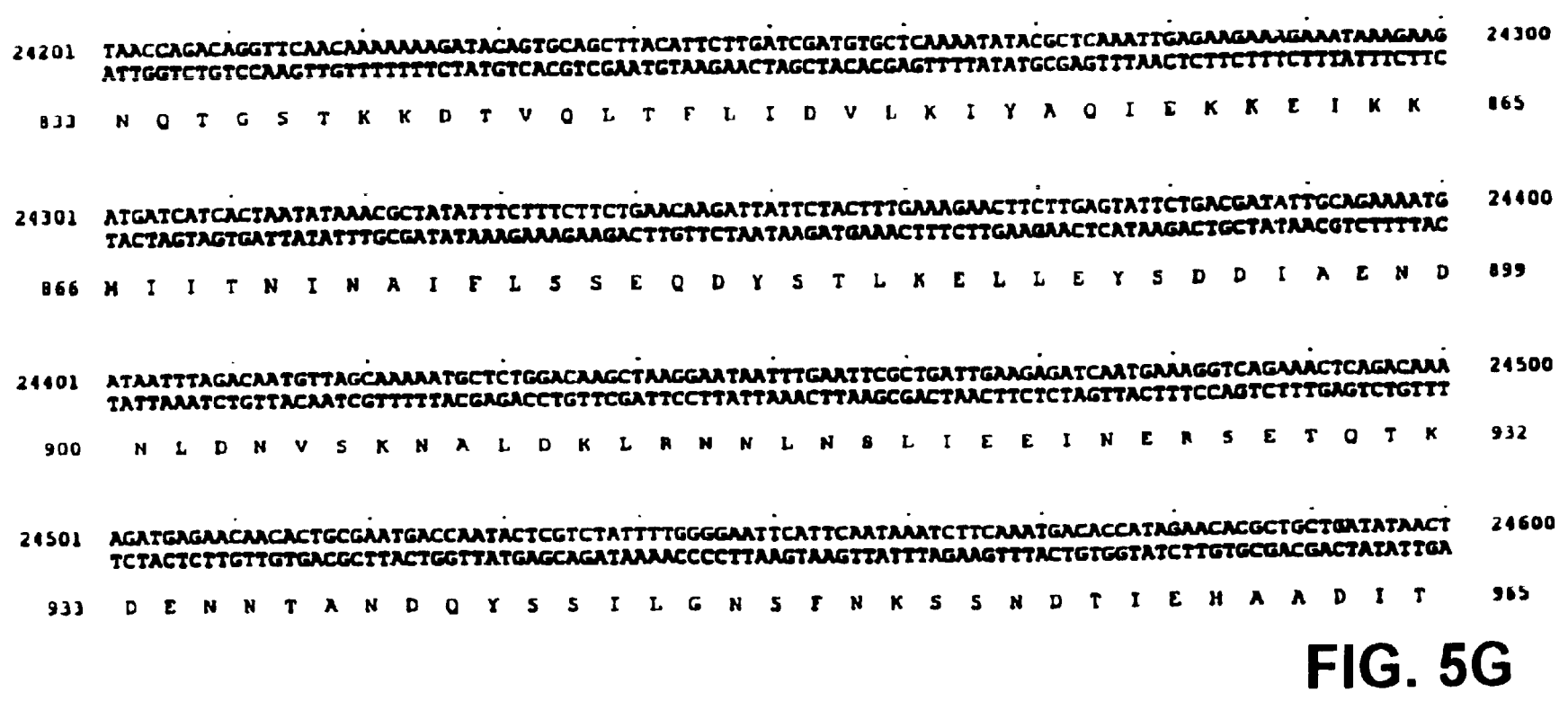
Figure 5H:
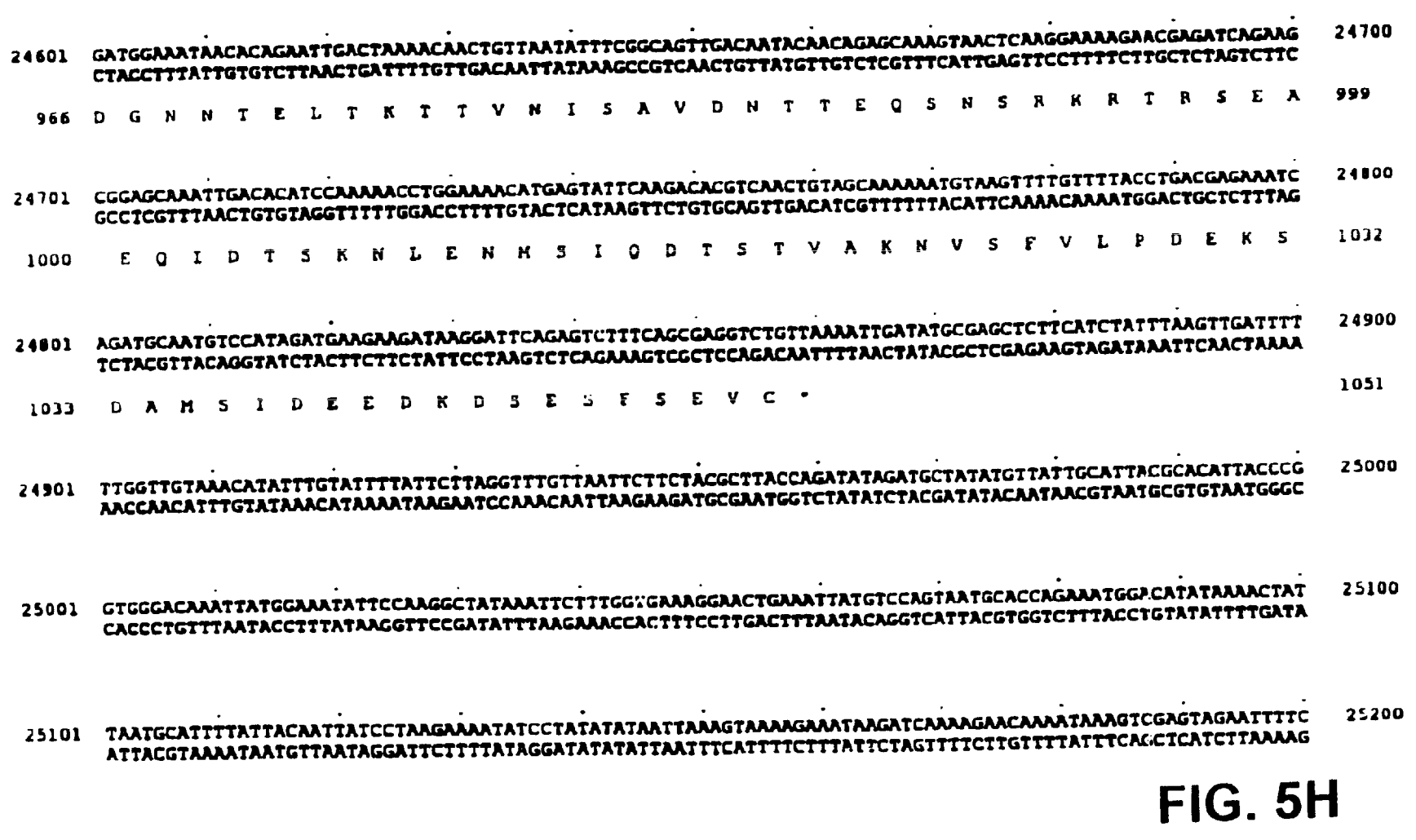

FIGS. 5A to 5H are a representation of the amino acid and nucleic acid sequences of the D9798.4 polypeptide and gene from *S. cerevisiae* (SEQ ID NOs:14 and 13, respectively). The non-coding sequence is set forth as SEQ ID NO:15.

FIGS. 6A to 6D are a representation of the amino acid and nucleic acid sequences of the YGR010W polypeptide and gene from *S. cerevisiae* (SEQ ID NOs:17 and 1:6, respectively). The non-coding sequence is set forth as SEQ ID NO:18.

FIGS. 7A to 7G are a representation of the amino acid and nucleic acid sequences of the L8543.16 polypeptide and gene from *S. cerevisiae* (SEQ ID NOs:20 and 19, respectively). The non-coding sequence is set forth as SEQ ID NO:21.

Figure 8C:
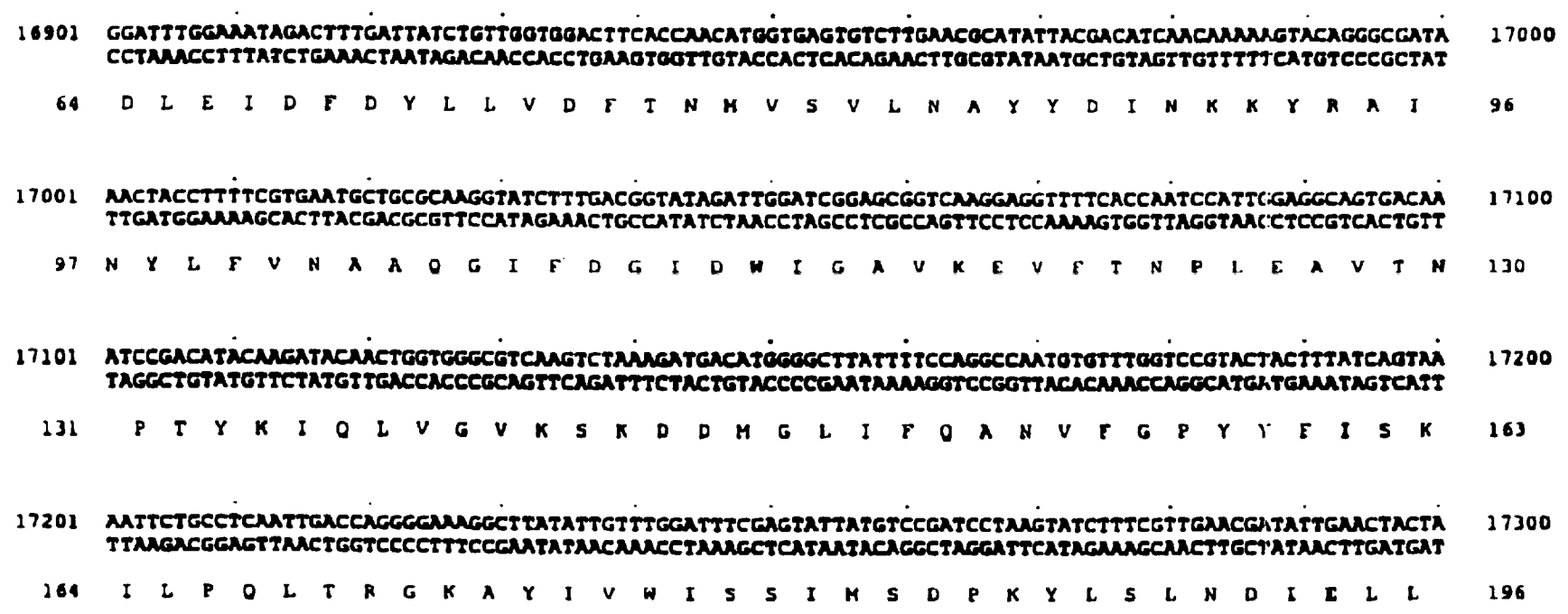
Figure 8D:
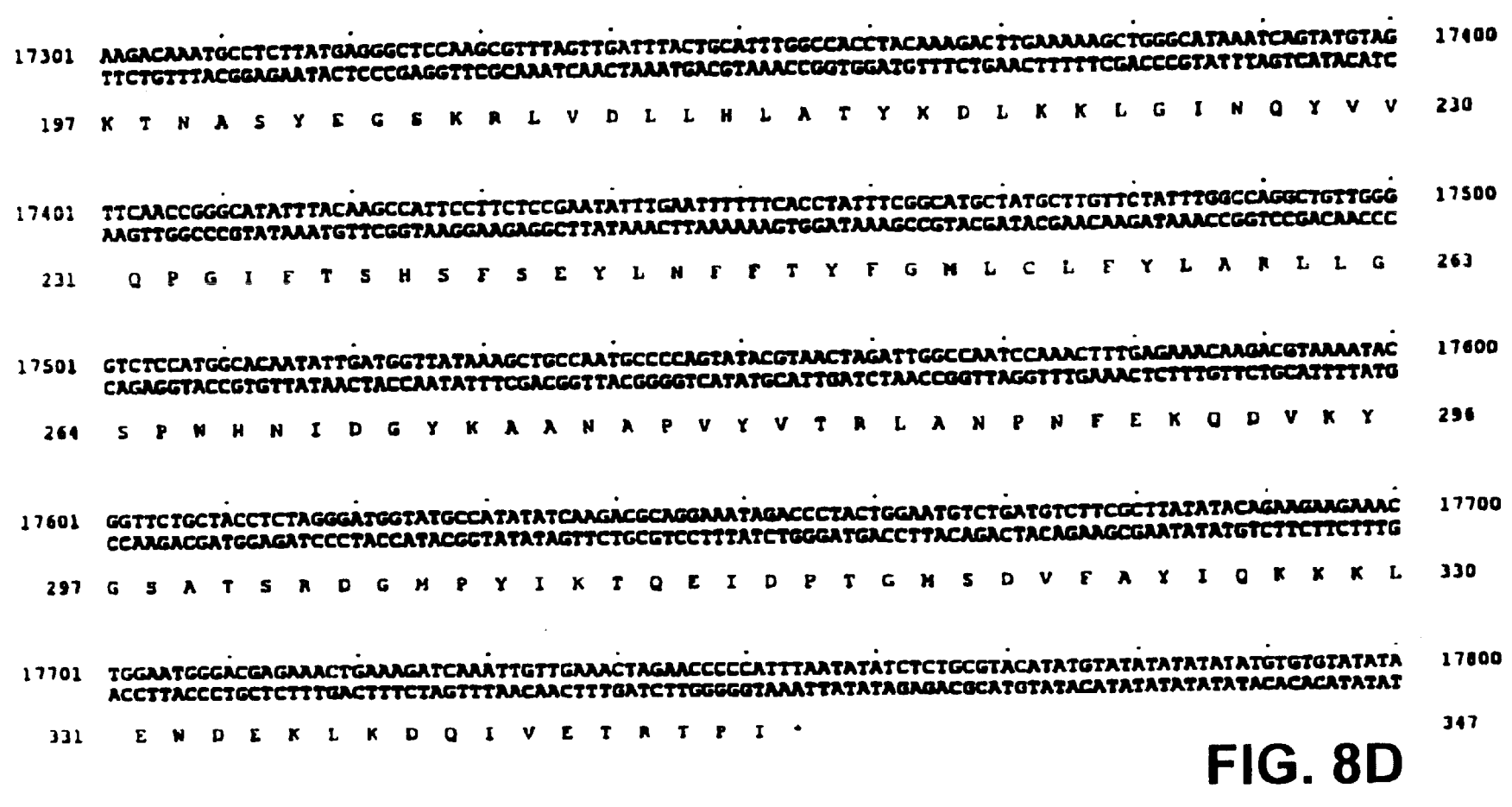

FIGS. 8A to 8D are a representation of the amino acid and nucleic acid sequences of the L8004.2 polypeptide and gene from *S. cerevisiae* (SEQ ID NOs:23 and 22, respectively). The non-coding sequence is set forth as SEQ ID NO:24.

DETAILED DESCRIPTION OF THE INVENTION

Identifying Essential Aspergillus Genes

As shown by the experiments described below, expression of each of the AN97, AN17, AN80, and AN85 polypeptides is essential for survival of Aspergillus nidulans. *Aspergillus nidulans* is available from the ATCC (#FGSC4). To identify genes for which inhibition of gene expression is fungicidal, various mutants of *Aspergillus nidulans* were assayed for conditional sensitivity. In general, mutagenesis of *Aspergillus nidulans* can be accomplished using any of various art-known methods. For example, exposure to ultraviolet light, x-rays, and/or chemical mutagens is acceptable. Examples of suitable chemical mutagens include ethylmethansulfonate (EMS), metyhlmethanesulfonate (MMS), methylnitrosoguanidine (NTG), 4-nitroquinoline-1-oxide (NQO), 2-aminopurine, 5-bromouracil, ICR 191 and other acridine derivatives, sodium bisulfite, ethidium bromide, nitrous acid, hydroxylamine, N-methyl-N'-nitroso-N-nitroguanidine, and alkylating agents (for further description of art-known mutagens and mutagenesis methods, see, e.g., Current Protocols in Molecular Biology, 1995 and Adelberg et al., *Biochem. Biophys. Res. Comm.* 18:788, 1965).

To identify conditional-sensitive mutants, mutagenized cells can be grown under (a) a first set of permissive conditions, then shifted to (b) restrictive conditions, and then to (c) a second set of permissive conditions. The cells of interest are those mutants that grow under the permissive conditions of (a), but fail to grow under the restrictive conditions of (b), and fail to recover under the permissive conditions of (c).

Ostensibly, any change in a growth parameter can serve as the "restrictive condition." For example, the restrictive conditions may be met by increasing or decreasing the temperature at which the cells are grown, thereby allowing the identification of temperature-sensitive mutants. For example, the optimal growth temperature for *A. nidulans* is 28° C., and a typical restrictive temperature is 42° C. In alternative methods, the change to a restrictive condition may entail changing one or more of the following parameters of the growth conditions: pH, type and/or concentration of carbon and nitrogen sources, trace minerals, vitamins, salts, conidia-forming materials (e.g., DMSO, glycerol, and deuterated water), humidity, and the like. In general, permissive growth conditions allow the strains to grow at a rate that is at least 75% of that of the wild-type growth rate of Aspergillus. The second set of permissive conditions (in (c)) can be the same as, or different from, the first permissive conditions. Typically, the cells are subjected to the second permissive conditions for at least 2 growth cycles (more typically, at least 5, 10, 15 or even 20 growth cycles). Generally, the cells are subjected to the restrictive conditions for 2 to 20 growth cycles (typically 2–10 growth cycles) and for 24 hours or less.

In practicing the invention, cell death (e.g., in (b)) can be detected using any of a number of conventional criteria. For example, cell death can be detected macroscopically by observing that a colony of cells has approximately the same size, or a reduced size, after a length of time that is normally sufficient for several growth cycles under the second permissive conditions. Detection of cell death also can be facilitated by the use of light microscopy and cell staining to reveal cytological deformations and/or morphologies commonly known to be indicative of cell death. The absence of DNA, RNA, or protein synthesis also can signify cell death.

Identification of Homologs of AN Polypertides

Having shown that the AN97, and AN80, and AN85 genes and polypeptides are essential for survival in Aspergillus, it can be expected that homologs of these polypeptides, when present in other organisms, for example pathogenic yeast, are essential for survival of those organisms as well. Using the sequences of the AN polypeptides identified in Aspergillus, homologs of these polypeptides were identified in the yeast *S. cerevisiae*. The coding sequences of AN97, AN80, and AN85 were used to search the GenBank database of nucleotide sequences to identify homologs of AN97, AN80, and AN85, respectively, which are essential genes in other organisms. Sequence comparisons were performed using the Basic Local Alignment Search Tool (BLAST) (Altschul et al., *J. Mol. Biol.*, 215:403–410 1990). The percent sequence identity shared by the AN polypeptides and their homologs were determined using the GAP program from the Genetics Computer Group (GCG) Wisconsin Sequence Analysis Package (Wisconsin Package Version 9.0, GCG; Madison, Wis.). The following parameters were used: gap creation penalty, 12 (protein) 50 (DNA); gap extension penalty, 4 (protein) 3 (DNA). The percent sequence identity shared by the AN polypeptides and their homologs are summarized in Table 1. Typically, the AN polypeptides and their homologs share at least 25% (e.g., at least 40%) sequence identity. Typically, the DNA sequences encoding AN polypeptides and their homologs share at least 35% (e.g., at least 45%) sequence identity.

TABLE 1

Sequence Identity Shared by AN Polypeptides and Their Homologues.

| AN Polypeptide | Homolog in Saccharomyces | % Identity of DNA Sequences (coding region) | % Identity of Polypeptide Sequences |
| --- | --- | --- | --- |
| AN80 | L8004.2 | 37.4 | 27.9 |
| AN85 | YGR010W | 50.2 | 41.0 |
| AN85 | L8543.16 | 49.2 | 43.7 |
| AN97 | D9798.4 | 38.7 | 25.8 |

To confirm that these yeast homologs of the AN polypeptides are essential for survival of yeast, the gene encoding each of the homologs was, separately, deleted from the *S. cerevisiae* genome. To this end, standard methods for making yeast "knock outs" were used, as described by Baudin et al., *Nucl. Acids. Res.* 21:3329–3330, 1993. Briefly, a portion of the yeast genome was amplified in a polymerase chain reaction (PCR) that employed two primers. The primers for L8004.2 were 5'AGGAAAGTAGCTATCGTAACGGG-TACTAATAGTAATCTTGGTCTCTTGGCCTCCTCTAG3' (SEQ ID NO:25) and 5'TACGCAGAGATATAT- TAAATGGGGGTTCTAGTTTCAA-
CAATTTCGTTCAGAATGACACG3' (SEQ ID NO:26).
The primers for D9798.4 were 5'TTAACAGCCGCGC-
CCATCATGCAAGATCCTGATGGTATTGA-
CATTCTCTTGGCCTCCTCTAG3' (SEQ ID NO:18) and
5'GCATATCAATTTTAACAGACCTCGCT-
GAAAGACTCTGAATCCTCGTTCAGAATGACACG3'
(SEQ ID NO:28). These primers hybridized to a portion of
the 5' and 3' sequences flanking the open reading frames of
the yeast homologs and include nucleotides that are homologous to the HIS3 selectable marker. Following PCR amplification, the resulting crude mix was directly used to transform yeast, following a standard protocol.

Identification of AN97, AN17, AN80, and AN85 Genes in Additional Aspergillus Strains Now that the AN97, AN80, AN17, and AN85 genes and their yeast homologs, L8004.2, YGR010W, L8543.16, and D9798.4, have been identified as essential for survival (as described below under "Examples"), these genes, or fragments thereof, can be used to detect homologous essential genes in other organisms. In particular, these genes can be used to analyze various pathogenic and non-pathogenic strains of Aspergillus (e.g., *Aspergillus fumigatus*, *Aspergillus flavus* and *Aspergillus niger*) and yeast (e.g., *Candida albicans*). In particular, fragments of a nucleic acid (DNA or RNA) encoding an AN polypeptide or yeast homolog (or sequences complementary thereto) can be used as probes in conventional nucleic acid hybridization assays of pathogenic organisms (e.g., pathogenic Aspergillus strains). For example, nucleic acid probes (which typically are 8–30, or usually 15–20, nucleotides in length) can be used to detect the AN97, AN17, AN80, AN85 genes or homologs thereof in art-known molecular biology methods, such as Southern blotting, Northern blotting, dot or slot blotting, PCR amplification methods, colony hybridization methods, and the like. Typically, an oligonucleotide probe based on the nucleic acid sequences described herein, or fragments thereof, is labeled and used to screen a genomic library or a cDNA library constructed from mRNA obtained from an Aspergillus or yeast strain of interest. A suitable method of labeling involves using polynucleotide kinase to add $^{32}$P-labeled ATP to the oligonucleotide used as the probe. This method is well known in the art, as are several other suitable methods (e.g., biotinylation and enzyme labeling).

Hybridization of the oligonucleotide probe to the cDNA library, or other nucleic acid sample, typically is performed under moderate to high stringency conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having ≧95% identity with the probe are sought, the final wash temperature is decreased by 5° C.). In practice, the change in $T_m$ can be between 0.5° and 1.5° C. per 1% mismatch.

As used herein, high stringency conditions include, for example, hybridizing at 68° C. in 5×SSC/5×Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In one approach, cDNA libraries constructed from pathogenic or non-pathogenic Aspergillus or yeast strains can be screened. For example, such strains can be screened for AN97, AN17, AN85, or AN80 expression by Northern blot analysis. Upon detection of AN97, AN17, AN85, or AN80 transcripts or transcripts of homologs thereof, cDNA libraries can be constructed from RNA isolated from the appropriate strain, utilizing standard techniques well known to those of skill in the art. Alternatively, a total genomic DNA library can be screened using an AN97, AN17, AN85, or AN80 probe (or a probe directed to a homolog thereof).

New gene sequences can be isolated, for example, by performing PCR using two degenerate oligonucleotide primer pools designed on the basis of nucleotide sequences within the AN97, AN17, AN85 or AN80 genes, or their homologs, as depicted herein. The template for the reaction can be cDNA obtained by reverse transcription of mRNA prepared from strains known or suspected to express an AN97, AN17, AN85, or AN80 allele or an allele of a homolog thereof. The PCR product can be subcloned and sequenced to ensure that the amplified sequences represent the sequences of a new AN97, AN17, AN85, or AN80 nucleic acid sequence, or a sequence of a homolog thereof.

The PCR fragment can then be used to isolate a full length cDNA clone by a variety of known methods. For example, the amplified fragment can be labeled and used to screen a bacteriophage cDNA library. Alternatively, the labeled fragment can be used to screen a genomic library.

PCR technology also can be used to isolate full length cDNA sequences. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Now that the AN97, AN17, AN85, and AN80 genes and their homologs have been cloned, synthesis of the AN polypeptides or their homologs (or an antigenic fragment thereof) for use as antigens, or for other purposes, can readily be accomplished using any of the various art-known techniques. For example, an AN polypeptide or homolog, or an antigenic fragments(), can be synthesized chemically in vitro, or enzymatically (e.g., by in vitro transcription and translation). Alternatively, the gene can be expressed in, and the polypeptide purified from, a cell (e.g., a cultured cell) by using any of the numerous, available gene expression systems. For example, the polypeptide antigen can be produced in a prokaryotic host (e.g., *E. coli* or *B. subtilis*) or in eukaryotic cells, such as yeast cells or insect cells (e.g., by using a baculovirus-based expression vector).

Proteins and polypeptides can also be produced in plant cells, if desired. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The optimal methods of transformation or transfection and the choice of expression vehicle will depend on the host system selected. Transformation and transfection methods are described, e.g., in Ausubel et al., supra; expression vehicles may be chosen from those provided, e.g., in *Cloning Vectors: A Laboratory Manual* (P. H. Pouwels et al., 1985, Supp. 1987). The host cells harboring the expression vehicle can be cultured in conventional nutrient media, adapted as needed for activation of a chosen gene, repression of a chosen gene, selection of transformants, or amplification of a chosen gene.

If desired, AN polypeptides or their homologs can be produced as fusion proteins. For example, the expression vector pUR278 (Ruther et al., *EMBO J.*, 2:1791, 1983) can be used to create lacZ fusion proteins. The art-known pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an exemplary insect cell expression system, a baculovirus such as *Autographa californica* nuclear polyhedrosis virus (AcNPV), which grows in *Spodoptera frugiperda* cells, can be used as a vector to express foreign genes. A coding sequence encoding an AN polypeptide or homolog can be cloned into a non-essential region (for example the polyhedrin gene) of the viral genome and placed under control of a promoter, e.g., the polyhedrin promoter or an exogenous promoter. Successful insertion of a gene encoding an AN polypeptide or homolog can result in inactivation of the polyhedrin gene and production of non-occluded recombinant virus (i.e., virus lacking the proteinaceous coat encoded by the polyhedrin gene). These recombinant viruses are then used to infect insect cells (e.g., *Spodoptera frugiperda* cells) in which the inserted gene is expressed (see, e.g., Smith et al., *J. Virol.*, 46:584, 1983; Smith, U.S. Pat. No. 4,215,051).

In mammalian host cells, a number of viral-based expression systems can be utilized. When an adenovirus is used as an expression vector, the nucleic acid sequence encoding the AN polypeptide or homolog can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region El or E3) will result in a recombinant virus that is viable and capable of expressing an AN97, AN17, AN85, or AN80 gene product in infected hosts (see, e.g., Logan, Proc. Natl. Acad. Sci. USA, 81:3655, 1984).

Specific initiation signals may be required for efficient translation of inserted nucleic acid sequences. These signals include the ATG initiation codon and adjacent sequences. In cases where an entire native gene (e.g., AN97) or cDNA, including its own initiation codon and adjacent sequences, is inserted into the appropriate expression vector, no additional translational control signals may be needed. In other cases, exogenous translational control signals, including, perhaps, the ATG initiation codon, should be provided. Furthermore, the initiation codon must be in phase with the reading frame of the desired coding sequence to ensure translation of the entire sequence. These exogenous translational control signals and initiation codons can be of a variety of origins, both natural and synthetic. The efficiency of expression may be enhanced by the inclusion of appropriate transcription enhancer elements, or transcription terminators (Bittner et al., Methods in Enzymol., 153:516, 1987).

The AN polypeptides and homologs can be expressed individually or as fusions with a heterologous polypeptide, such as a signal sequence or other polypeptide having a specific cleavage site at the N- and/or C-terminus of the protein or polypeptide. The heterologous signal sequence selected should be one that is recognized and processed, i.e., cleaved by a signal peptidase, by the host cell in which the fusion protein is expressed.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein. Various host cells have characteristic and specific mechanisms for post-translational processing and modification of proteins and gene products. Appropriate cell lines or host systems familiar to those of skill in the art of molecular biology can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, and choroid plexus cell lines.

If desired, the AN polypeptide or homolog thereof can be produced by a stably-transfected mammalian cell line. A number of vectors suitable for stable transection of mammalian cells are available to the public, see, e.g., Pouwels et al. (supra); methods for constructing such cell lines are also publicly known, e.g., in Ausubel et al. (supra). In one example, cDNA encoding the protein is cloned into an expression vector that includes the dihydrofolate reductase (DHFR) gene. Integration of the plasmid and, therefore, the AN polypeptide-encoding gene into the host cell chromosome is selected for by including 0.01–300 $\mu$M methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra).

A number of other selection systems can be used, including but not limited to the herpes simplex virus thymidine kinase, hypoxanthine-guanine phosphoribosyl-transferase, and adenine phosphoribosyltransferase genes can be employed in tk, hgprt, or aprt cells, respectively. In addition, gpt, which confers resistance to mycophenolic acid (Mulligan et al., *Proc. Natl. Acad. Sci. USA*, 78:2072, 1981); neo, which confers resistance to the aminoglycoside G-418 (Colberre-Garapin et al., *J. Mol. Biol.*, 150:1, 1981); and hygro, which confers resistance to hygromycin (Santerre et al., *Gene*, 30:147, 1981), can be used.

Alternatively, any fusion protein can be readily purified by utilizing an antibody or other molecule that specifically binds the fusion protein being expressed. For example, a system described in Janknecht et al., *Proc. Natl. Acad. Sci. USA*, 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$nitriloacetic acid-agarose columns, and histidine-tagged proteins are selectively eluted with imidazole-containing buffers.

Alternatively, an AN polypeptide or homolog, or a portion thereof, can be fused to an immunoglobulin Fc domain. Such a fusion protein can be readily purified using a protein A column, for example. Moreover, such fusion proteins permit the production of a chimeric form of an AN polypeptide or homolog having increased stability in vivo.

Once the recombinant AN polypeptide (or homolog) is expressed, it can be isolated (i.e., purified). Secreted forms of the polypeptides can be isolated from cell culture media, while non-secreted forms must be isolated from the host cells. Polypeptides can be isolated by affinity chromatography. For example, an anti-AN97 antibody (e.g., produced as described herein) can be attached to a column and used to isolate the protein. Lysis and fractionation of cells harboring the protein prior to affinity chromatography can be performed by standard methods (see, e.g., Ausubel et al., supra). Alternatively, a fusion protein can be constructed and used to isolate an AN polypeptide (e.g., an AN97-maltose binding fusion protein, an AN97-β-galactosidase fusion protein, or an AN97-trpE fusion protein; see, e.g., Ausubel et al., supra; New England Biolabs Catalog, Beverly, Mass.). The recombinant protein can, if desired, be further purified, e.g., by high performance liquid chromatography using standard techniques (see, e.g., Fisher, *Laboratory Techniques In Biochemistry And Molecular Biology*, eds., Work and Burdon, Elsevier, 1980).

Given the amino acid sequences described herein, polypeptides useful in practicing the invention, particularly fragments of AN97, AN17, AN85, AN80 from pathogenic Aspergillus strains, and fragments of D9798.4, L8004.2, L8543.16, and YGR010W from yeast, can be produced by standard chemical synthesis (e.g., by the methods described in Solid Phase Peptide Synthesis, 2nd ed., The Pierce Chemical Co., Rockford, Ill., 1984) and used as antigens, for example.

Antibodies

AN97, AN17, AN85, or AN80 polypeptides (or antigenic fragments or analogs of such polypeptide) can be used to raise antibodies useful in the invention, and such polypeptides can be produced by recombinant or peptide synthetic techniques (see, e.g., *Solid Phase Peptide Synthesis*, supra; Ausubel et al., supra). Likewise, antibodies can be raised against the yeast homologs. In general, the polypeptides can be coupled to a carrier protein, such as KLH, as described in Ausubel et al., supra, mixed with an adjuvant, and injected into a host mammal. Antibodies can be purified, for example, by affinity chromatography methods in which the polypeptide antigen is immobilized on a resin.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete), adjuvant mineral gels such as aluminum hydroxide, surfacelactive substances such as lysolecithin, pluronic polyols, polyanions, peptides, oil emulsions, keyhole limpet hemocyanin, dinitrophenol, BCG (bacille Calmette-Guerin) and *Corynebacterium parvum*. Polyclonal antibodies are heterogeneous populations of antibody molecules derived from the sera of the immunized animals.

Antibodies within the invention include monoclonal antibodies, polyclonal antibodies, humanized or chimeric antibodies, singlelchain antibodies, Fab fragments, $F(ab')_2$ fragments, and molecules produced using a Fab expression library.

Monoclonal antibodies (mAbs), which are homogeneous populations of antibodies to a particular antigen, can be prepared using the AN polypeptides or homologs thereof and standard hybridoma-technology (see, e.g., Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., In *Monoclonal Antibodies and T Cell Hybridomas*, Elsevier, N.Y., 1981; Ausubel et al., supra).

In particular, monoclonal antibodies can be obtained by any technique that provides for the production of antibody molecules by continuous cell lines in culture, such as those described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983); and the EBV-hybridoma technique (Cole et al., *Monoclonal Antibodies and Cancer Therapy*, Alan R. Liss, Inc., pp. 77–96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies are tested for specific recognition of an AN polypeptide or homolog thereof in an immunoassay, such as a Western blot or immunoprecipitation analysis using standard techniques, e.g., as described in Ausubel et al., supra. Antibodies that specifically bind to AN97, AN17, AN85, or AN80, or conservative variants and homologs thereof, are useful in the invention. For example, such antibodies can be used in an immunoassay to detect AN97 in pathogenic or non-pathogenic strains of Aspergillus (e.g., in Aspergillus extracts).

Preferably, antibodies of the invention are produced using fragments of the AN polypeptides that appear likely to be antigenic, by criteria such as high frequency of charged residues. In one specific example, such fragments are generated by stanllard techniques of PCR, and are then cloned into the PGEX expression vector (Ausubel et al., supra). Fusion proteins are expressed in *E. coli* and purified using a glutathione agarose affinity matrix as described in Ausubel, et al., supra.

If desired, several (e.g., two or three) fusions can be generated for each protein, and each fusion can be injected into at least two rabbits. Antisera can be raised by injections in a series, typically including at least three booster injections. Typically, the antisera is checked for its ability to impiunoprecipitate a recombinant AN polypeptide or homolog, or unrelated control proteins, such as glucocorticoid receptor, chloramphenicol acetyltransferase, or luciferase.

Techniques developed for the production of "chimeric antibodies" (Morr:Lson et al., *Proc. Natl. Acad. Sci.*, 81:6851, 1984; Neiberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; and U.S. Pat. Nos. 4,946,778 and 4,704,692) can be adapted to produce single chain antibodies against an AN polypeptide or homolog. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments canjinclude but are not limited to F(ab')$_2$ fragments, which can be produced by pepsin digestion of the antibody molecule, and Fab fragments, which can be generated by reducing the disulfide bridges of F(ab')$_2$ fragments. Alternatively, Fab expression libraries can be constructed (Huse et al., *Science*, 246:1275, 1989) to allow rapid and easy identification of monoclonal Fab fragments with the desired specificity.

Polyclonal and monoclonal antibodies that specifically bind AN polypeptides or homologs can be used, for example, to detect expression of an AN97, AN17, AN85, AN80 gene or homolog in another strain of Aspergillus. For example, AN97 polypeptide can be1 readily detected in conventional immunoassays of Aspergillus cells or extracts. Examples of suitable assays include, without limitation, Western blotting, ELISAs, ;radioimmune assays, and the like.

Assay for Antifungal Agents

The invention provides a method for identifying an antifungal agent(s). Although the inventors are not bound by any particular theory as to the biological mechanism involved, the new antifungal agents are thought to inhibit specifically the function of the AN polypeptides or expression of the AN97, AN17, AN85, or AN80 genes, or homologs thereof. Screening for antifungal agents can be rapidly accomplished by identifying those compounds (e.g., polypeptides, ribonucleic acids (including ribozymes), nucleic acids (including antisense nucleic acids), or small molecules) that specifically bind to an AN polypeptide. A homolog of an AN polypeptide (e.g., D9798.4, L8004.2, L8543.16, or YGR010W,) can be substituted for the AN polypeptide in the methods summarized herein. Specific binding of a test compound to an AN polypeptide can be detected, for example, in vitro by reversibly or irreversibly immobilizing the test compound(s) on a substrate, e.g., the surface of a well of a 96-well polystyrene microtitre plate. Methods for immobilizing polypeptides and other small molecules are well known in the art. For example, the microtitre plates can be coated with an AN polypeptide (or a combination of AN polypeptides and/or homologs) by adding the polypeptide(s) in a solution (typically, at a concentration of 0.05 to 1 mg/ml in a volume of 1–100 µl) to each well, and incubating the plates at room temperature to 37° C. for 0.1 to 36 hours. Polypeptides that are not bound to the plate can be removed by shaking the exce ss solution from the plate, and then washing the plate (once or repeatedly) with water or a buffer. Typically, the AN polypeptide or homolog is contained in water or a buffer. The plate is then washed with a buffer that lacks the bound polypeptide. To block the free protein-binding sites on the plates, the plates are blocked with a protein that is unrelated to the bound polypeptide. For example, 300 µl of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate.

Binding of theitest compound to the new AN polypeptides (or homologs thereof) can be detected by any of a variety of art-known methods. For example, an antibody that specifically binds an AN polypeptide can be used in an immunoassay. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds the Fc portion of an anti-AN97 antibody). In an alternative detection method, the AN polypeptide is labeled, and the label is detected (e.g., by labeling an AN polypeptide with a radioisotope, fluorophore, chromophore, or the like). In still another method, the AN polypeptide is produced as a fusion protein with a protein thatlcan be detected optically, e.g., green fluorescent proteini (which can be detected under UV light). In an alternative method, the AN polypeptide can be produced as a fusion protein with an enzyme having a detectable enzymatic activity, such as horse radish peroxidase, alkaline phosphatase, α-galactosidase, or glucose oxidase. Genes encoding all of these enzymes have been cloned and are readily available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and α-galactosidase) and non-enzymatic polypeptides (e.g., serum proteins, such as BSA and globulins, and milk proteins, such as caseins).

In various in ivivo methods for identifying polypeptides that bind AN polypeiptides, the conventional two-hybrid assays of protein/protein interactions can be used (see e.g., Chien et al., *Proc. Natl. Acad. Sci. USA*, 88:9578, 1991; Fields et al., U.S. Pat. No. 5,283,173; Fields and Song, *Nature*, 340:245, 1989; Le Douarin et al., *Nucleic Acids Research*, 23:1876, 1995; Vidal et al., *Proc. Natl. Acad. Sci. USA*, 93:10315–10320, 1996; and White, *Proc. Natl. Acad. Sci. USA*, 93:10001–10003, 1996). Kits for practicing various two-hybrid methods are commercially available (e.g., from Clontech; Palo Alto, Calif.).

Generally, the two-hybrid methods involve in vivo reconstitution of two separable domains of a transcription factor. The DNA binding domain (DB) of the transcription factor is required for recognition of a chosen promoter. The activation domain (AD) is required for contacting other components of the host cell's transcriptional machinery. The transcription factor is reconstituted through the use of hybrid proteins. One hybrid is composed of the AD and a first protein of interest. The second hybrid is composed of the DB and a second protein of interest. In cases where the first and second proteins of interest interact with each other, the AD and DB are brought into close physical proximity, thereby reconstituting the transcription factor. Association of the proteins can be measured by assaying the ability of the reconstituted transcription factor to activate transcription of a reporter gene.

Useful reporter genes are those that are operably linked to a promoter which is specifically recognized by the DB. Typically, the two-hybrid system employs the yeast *Saccharomyces cerevisiae* and reporter genes, the expression of which can be selected under appropriate conditions. Other eukaryotic cells, including mammalian and insect cells, can be used, if desired. The two-hybrid system provides a convenient method for cloning a gene encoding a polypeptide (i.e., a candidate antifungal agent) that binds a second, preselected polypeptide (e.g., AN97). Typically, though not necessarily, a cDNA library is constructed such that randomly generated sequences are fused to the AD, and the protein of interest (e.g., AN97 or AN80) is fused to the DB.

In such two-hybrid methods, two fusion proteins are produced. One fusion protein contains the AN polypeptide (or homolog thereof) fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the AN polypeptide to the test polypeptide (i.e., candidate antifungal agent) reconstitutes the transcription factor. Reconstitution of the transcription factor can be detected by detecting expression of a gene (i.e., a reporter gene) that is operably linked to a DNA sequence that is bound by the DNA binding domain of the transcription factor.

The methods described above can be used for high thoughput screening of numerous test compounds to identify candidate antifungal (or anti-yeast) agents. Having identified a test compound as a candidate antifungal agent, the candidate antifungal agent can be further tested for inhibition of fungal growth in vitro or in vivo (e.g., using an animal, e.g., rodent, model system) if desired. Using other, art-known variations of such methods, one can test the ability of a nucleic acid (e.g., DNA or RNA) used as the test compound to bind an AN polypeptide or homolog thereof.

In vitro, further testing can be accomplished by means known to those in the art such as an enzyme inhibition assay or a whole-cell fungal growth inhibition assay. For example, an agar dilution assay identifies a substance that inhibits fungal growth. Microtiter plates are prepared with serial dilutions of the test compound; adding to the preparation a given amount of growth substrate; and providing a preparation of Aspergillus spores. Inhibition of growth is determined, for example, by observing changes in optical densities of the fungal cultures.

Inhibition of fungal growth is demonstrated, for example, by comparing (in the presence and absence of a test compound) the rate of growth or the absolute growth of fungal sporulation or nuclei. Inhibition includes a reduction of one of the above measurements by at least 20% (e.g., at least 25%, 30%, 40%, 50%, 75%, 80%, or 90%).

Rodent (e.g., murine) and bovine animal models of aspergillosis are known to those of skill in the art, and such animal model systems are accepted for screening antifungal agents as an indication of their therapeutic efficacy in human patients (Rhodes et al., *J. Med. and Vet. Myco.*, 30:51–57, 1992). Indeed, the clinical manifestations of bovine aspergillosis show many pathological similarities to aspergillosis in humans and rodents. In a typical in vivo assay, an animal is infected with a pathogenic Aspergillus strain, e.g., by inhalation of Aspergillus spores (i.e., conidia), and conventional methods and criteria are used to diagnose the mammal as being afflicted with aspergillosis. The candidate antifungal agent then is administered to the mammal at a dosage of 1–100 mg/kg of body weight, and the mammal is monitored for signs of amelioration of disease. Alternatively, the test compound can be administered to the mammal prior to infecting the mammal with Aspergillus, and the ability of the treated mammal to resist infection is measured. Of course, the results obtained in the presence of the test compound are compared with results in control animals, which are not treated with the test compound. Administration of candidate antifungal agent to the mammal can be carried out as described below, for example.

Antisense Methods

Antisense approaches involve the design of oligonucleotides (either DNA or RNA) that are complementary to AN97, AN17, AN80, or AN85 mRNA. The antisense oligonucleotides bind to the AN97, AN17, AN80, or AN85 coding sequences and/or mRNA transcripts and inhibit transcription and/or translation. Absolute complementarity is not required. A sequence "complementary" to a portion of an RNA, as referred to herein, means a sequence having sufficient complementarity to be able to hybridize with the RNA and form a stable duplex; in the case of double-stranded antisense nucleic acids, a single strand of the duplex-DNA can be tested, or triplex formation can be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well (Wagner, *Nature*, 372:333, 1984). Thus, oligonucleotides complementary to either the 5'- or 3'- non-translated, non-coding regions of the AN97, AN17, AN80, or AN85 genes, or their yeast homologs D9798.4, L8543.16, YGR010W, of L8004.2, as represented by SEQ ID NOs:1, 4, 7, 10, 13, 16, 19, and 22 can be used in an antisense approach to inhibit translation of the endogenous sequences. Oligonucleotides complementary to the 5' untranslated region of the mRNA typically also include the complement of the AUG start codon.

Antisense oligonucleotides complementary to mRNA coding regions are less preferred inhibitors of translation, but can be used in accordance with the invention. Whether designed to hybridize to the 5'-, 3'-, or coding region of the mRNA, antisense nucleic acids should be at least six nucleotides in length (e.g., oligonucleotides ranging from 6 to about 50 nucleotides in length). In specific. aspects, the oligonucleotide is at least 10 nucleotides, at least 15 nucleotides, or at least 25 nucleotides.

Regardless of the choice of target sequence, in vitro studies typically are first performed to quantitate the ability of the antisense oligonucleotide to inhibit gene expression. Typically, these studies utilize controls that distinguish between antisense gene inhibition and nonspecific biological effects of oligonucleotides. Generally, these studies compare levels of the target RNA or protein with that of an internal control RNA or protein.

Additionally, it is envisioned that results obtained using the antisense oligonucleotide are compared with those obtained using a control oligonucleotide. Typically, the control oligonucleotide is of approximately the same length as the test oligonucleotide and that the nucleotide sequence of the oligonucleotide differs from the antisense sequence no more than is necessary to prevent specific hybridization to the target sequence.

The antisense oligqnucleotides can be DNA or RNA, or chimeric mixtures, or derivatives or modified versions thereof, and can be single-stranded or double-stranded. The oligonucleotides can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., Proc. Natl. Acad. Sci. USA, 86:6553, 1989; Lemaitre et al., Proc. Natl. Acad. Sci. USA, 84:648, 1987; PCT Publication No. WO 88/09810) or the blood-brain barrier (see, e.g., PCT Publication No. WO 89/10134), or hybridization-triggered cleavage agents (see, e.g., Krol et al., BioTechniques, 6:958, 1988), or intercalating agents (see, e.g., Zon, Pharm. Res., 5:539, 1988). To this end, the oligonucleotide can be conjugated to another molecule, e.g., a peptide, hybridization triggered cross-linking agent, transport agent, or hybridization-triggered cleavage agent.

The antisense oligonucleotide can include at least one modified base moiety selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethyl aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropyl) uracil, (acp3) w, and 2,6-diaminopurine.

The antisense oligonucleotide can also include at least one modified sugar moiety selected from the group including, but not limited to, arabinose, 2-fluoroarabinose, xylulose, and hexose.

In yet another embodiment, the antisense oligonucleotide includes at least one modified phosphate backbone, e.g., a phosphorothioate, a phosphorodithioate, a phosphoramidothioate, a phosphoramidate, a phosphorodiamidate, a methylphosphonate, an alkyl phosphotriester, and a formacetal, or an analog of any of these backbones.

In addition, the antisense oligonucleotide can be an α-anomeric oligonucleotide that forms specific double-stranded hybrids with complementary RNA in which, contrary to the usual β-units, the strands run parallel to each other (Gautier et al., Nucl. Acids. Res., 15:6625, 1987). The oligonucleotide can be a 2'-0-methylribonucleotide (Inoue et al., Nucl. Acids Res., 15:6131, 1987), or a chimeric RNA-DNA analog (Inoue et al., FEBS Lett., 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al., Nucl. Acids Res., 16:3209, 1988, and methylphosphonate oligonucleotides can be prepared by use of controlled pore glass polymer supports (Sarin et al., Proc. Natl. Acad. Sci. USA, 85:7448, 1988).

While antisense nucleotides complementary to the AN97, AN17, AN80, AN85, D9798.4, L8543.16, YGR010W, or L8004.2 coding region sequence could be used, those complementary to the transcribed untranslated region are preferred. Generally, such antisense oligonucleotides are 10–100 nucleotides in length (e.g., 15–50 nucleotides). Pathogenic microorganisms, such as Aspergillus, can spontaneously phagocytose oligonucleotides. Accordingly, these antisense oligonucleotides can be administered systemically or locally to a patient suffering from a pathogen infection in order to deliver the antisense oligonucleotides to the infectious organism in a method of treatment. For example, such antisense oligonucleotides can be used to inhibit expression of an AN polypeptide and thereby treat or inhibit fungal infections. A suitable approach uses a recombinant DNA construct in which the antisense oligonucleotide is placed under the control of a strong pol III or pol II promoter. The use of such a construct to transfect fungal cells in the patient will result in the transcription of sufficient amounts of single stranded nucleic acids that form complementary base pairs with the endogenous transcripts encoding AN polypeptides and thereby prevent translation of the mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Appropriate vectors can be constructed by recombinant DNA technology methods standard in the art. Vectors can be plasmid, viral, or others known in the art, used for replication and expression in fungal cells. Expression of the sequence encoding the antisense RNA can be by any promoter known in the art to act in fungi, e.g. Aspergillus, cells. Such promoters can be inducible or constitutive, such as an alcohol dehydrogenase promoter (e.g., alcA) and a nitrate reductase promoter (e.g., niiA). Any type of plasmid, cosmid, or viral vector can be used to prepare the recombinant DNA construct which can be administered systemically or directly to the infected tissue.

Ribozymes

Ribozyme molecules designed to catalytically cleave MRNA transcripts encoding AN polypeptides also can be used to prevent translation of mRNA and expression of the AN polypeptides (see, e.g., PCT Publication WO 90/11364; Saraver et al., Science, 247:1222, 1990). Various ribozymes that cleave mRNA at site-specific recognition sequences can be used to destroy mRNAs encoding the AN polypeptides (e.g., the use of hammerhead ribozymes). Hammerhead ribozymes cleave mRNAs at locations dictated by flanking regions that form complementary base pairs with the target mRNA. It is recommended that the target mRNA have the following sequence of two bases: 5'-UG-3'. The construction and production of hammerhead ribozymes is known in the art (Haseloff et al., Nature, 334:585, 1988). There are numerous examples of potential hammerhead ribozyme cleavage sites within the nucleotide sequence of cDNAs encoding AN polypeptides (FIGS. 1 to 3). Typically, the ribozyme is engineered so that the cleavage recognition site is located near the 5' end of the mRNA encoding the AN polypeptide in order to increase efficiency and minimize the intracellular accumulation of non-functional mRNA transcripts.

The ribozymes of the present invention also include RNA endoribonucleases (hereinafter "Cech-type ribozymes"), such as the one that occurs naturally in Tetrahymena Thermophila (known as the IVS or L-19 IVS RNA), and which has been extensively described by Cech and his collaborators (Zaug et al., Science, 224:574, 1984; Zaug et al., Science, 231:470, 1986; Zug et al., Nature, 324:429, 1986; PCT Application No. WO 88/04300; and Been et al., Cell, 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in AN polypeptides.

As in the antisense approach, the ribozymes can be composed of modified oligonucleotides (e.g., for improved stability, targeting, etc.), and should be delivered to cells that express the AN polypeptide. A typical method of delivery involves using a DNA construct "encoding" the ribozyme under the control of a strong constitutive promoter, e.g., a pol III or pol II promoter, so that transfected cells will produce sufficient quantities of the ribozyme to destroy endogenous mRNAs encoding AN polypeptides and inhibit translation thereof. Because ribozymes, unlike typical antisense molecules, are catalytic, a lower intracellular concentration is required for efficiency.

Pharmaceutical Formulations

Treatment includes administering a pharmaceutically effective amount of a composition containing an antifungal agent to a subject in need of such treatment, thereby inhibiting fungal growth in the subject. Such a composition typically contains from about 0.1 to 90% by weight (such as 1 to 20% or 1 to 10%) of an antifungal agent of the invention in a pharmaceutically acceptable carrier.

Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a pharmaceutical formulation containing the antifungal agent and a physiologically acceptable excipient is infused. Physiologically acceptable excipients may include, for example, 5% dextrose, 0.9% saline, Ringer's solution or other suitable excipients. Intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid, (e.g., ethyl oleate).

A topical semi-solid ointment formulation typically contains a concentration of the active ingredient from about 1 to 20%, e.g., 5 to 10% in a carrier such as a pharmaceutical cream base. Various formulations for topical use include drops, tinctures, lotions, creams, solutions, and ointments containing the active ingredient and various supports and vehicles.

The optimal percentage of the antifungal agent in each pharmaceutical formulation varies according to the formulation itself and the therapeutic effect desired in the specific pathologies and correlated therapeutic regimens. Appropriate dosages of the antifungal agents can readily be determined by those of ordinary skill in the art of medicine by monitoring the mammal for signs of disease amelioration or inhibition, and increasing or decreasing the dosage and/or frequency of treatment as desired. The optimal amount of the antifungal compound used for treatment of conditions caused by or contributed to by fungal infection may depend upon the manner of administration, the age and the body weight of the subject and the condition of the subject to be treated. Generally, the antifungal compound is administered at a dosage of 1 to 100 mg/kg of body weight, and typically at a dosage of 1 to 10 mg/kg of body weight.

EXAMPLE

In this example, the identification and cloning of AN97, AN17, AN85, and AN80 are described.

A library of approximately 1,000 *A. nidulans* mutants was obtained, which was prepared using 4-nitroquinoline as a mutagen, as described previously (Harris et al., *Genetics* 136:517–532 1994). To identify strains having a temperature-sensitive mutation in an essential gene, the collection of 1,000 strains was grown at the permissive temperature of 28° C. for 16 hours in minimal medium (MN; pH 6.5, 1% glucose, nitrate salts and trace elements as described in Kafer, *Adv. Genet*. 19:33–131, 1977). The trace element solution was stored at 4° in the dark; each liter contained 40 mg $Na_2B_4O_7$ (10 $H_2O$), 400 mg cupric sulfate (5 $H_2O$), 1 g ferric phosphate (4 $H_2O$), 600 mg manganese sulfate (4 $H_2O$), 800 mg disodium molybdate (2 $H_2O$), and 8 g zinc sulfate (7 $H_2O$). Salt solution was stored at 4° C. after adding 2 ml chloroform as a preservative; each liter contained 26 g potassium chloride, 26 g magnesium sulfate (7 $H_2O$) 76 g monobasic potassium phosphate and 50 mL trace element solution. Supplement solution was sterilized by autoclaving for 15 minutes and stored in a light-proof container due to the reactivity of riboflavin. Each liter contains 100 mg nicotinic acid, 250 mg riboflavin, 200 mg pantothenic acid, 50 mg pyridoxin, 1 mg biotin, and 20 mg p-aminobenzoic acid.

Condidia ($2 \times 10^6$/ml in sterile, distilled water) were mutagenized with NQO (4 µg/ml) for 30 minutes at 37° C. with constant shaking. Diluting the conidia with an equal volume of 5% sodium thiosulfate inactivated the NQO.

Mutagenized conidia were diluted and plated onto CM+TRITON X-100 plates (from Union Carbide Chemicals,) and incubated at 28° C. for 3 days. Colonies were replica plated and the replica plated plates were incubated at 28° C. and 42° C. Putative temperature-sensitive mutants were picked and retested, then stored as a colony plug in 15% glycerol at −70° C.

The cells were replica plated and shifted to 42° C. for 24 hours. Strains that grew poorly or not at all were selected, because they were most likely to represent strains having a mutation in an essential gene. After 1 round of subjecting the collection of cells to the temperature shift, approximately 100 strains (10% of the strains) were identified as having failed to recover once they were shifted to the second permissive temperature. These 100 strains were again grown at a first permissive temperature, followed by 24 hours at 42° C., and 24 or 48 hours at 28° C. (the second permissive temperature). After this second round of selection, 10 strains were identified as having failed to recover, and therefore as containing a temperature sensitive mutation in an essential gene.

Complementation analysis was used to identify the essential gene containing the mutation for each strain. Each of the 10 mutant strains was transformed, separately, with an Aspergillus genomic cosmid library containing an ArgB marker in a pCosAx vector (Adams et al., *FEMS Microbiol. Lett.*, 122:227–231 1994). The strains were grown for 3–4 days at 28° C., replica plated, and shifted to 42° C. for a maximum of 3 days. Strains that grew were collected, and the cosmid DNA was packaged by "selfing" the organism to force it to undergo meiosis. In this method, a colony is picked and grown on a separate plate (which typically is sealed to prevent contamination). The resulting spores then are picked and grown in liquid culture, prior to isolating the DNA. The cosmid was packaged using GIGAPACK III Gold packaging system (Stratagene; La Jolla, Calif.), which produced plasmids that were subsequently isolated, purified, and used to transform bacteria for amplification, isolation, purification, and sequencing.

In one of the resulting strains, the mutation was in a gene designated "AN97," indicating that in *A. nidulans* this gene is essential for survival. The amino acid sequence of the AN97 polypeptide and the AN97 gene of *A. nidulans* are provided in FIG. 1 as SEQ ID NOs:2 and 29; and NO:1, respectively.

In a second strain, the mutation was in a gene designated "AN80" indicating that this gene is essential for survival. The AN80 amino acid and nucleic acid sequences are shown in FIG. 2 as SEQ ID NOs:5 and 4, respectively.

In a third strain, the mutation was in a gene designated "AN85," indicating that this gene is essential for survival. The AN85 amino acid and nucleic acid sequences are shown in FIG. 3 as SEQ ID NOs:8, 30, 31, and 32; and NO:7, respectively.

In a fourth strain, the mutation was in a gene designated "AN17," indicating that this gene is essential for survival. The AN17 amino acid and nucleic acid sequences are shown in FIG. 4 as SEQ ID NOs:11, 33, 34, and 35; and NO:10, respectively.

Now that each of these genes is known to be essential for survival of Aspergillus; the AN polypeptides (AN97, AN17, AN80, and AN85) can be used to identify antifungal agents by using the assays described herein. Other art-known assays to detect interactions of test compounds with proteins, or to detect inhibition of fungal growth also can be used with the AN97, AN17, AN80, and AN85 genes and gene products and homologs thereof.

Other Embodiments

The invention also features fragments, variants, analogs, and derivatives of the AN polypeptides described above that retain one or more of the biological activities of the AN polypeptides, e.g., as determined in a complementation assay. Also included within the invention are naturally-occurring and non-naturally-occurring allelic variants. Compared with the naturally-occurring AN97, AN80, AN85, and AN17 nucleotide sequences depicted in FIGS. 1, 2, 3, and 4 respectively, the nucleic acid sequence encoding allelic variants may have a substitution, deletion, or addition of one or more nucleotides. The preferred allelic variants are functionally equivalent to an AN polypeptide, e.g., as determined in a complementation assay.

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid encoding an AN80 polypeptide comprising the amino acid sequence set forth as SEQ ID NO:5 as depicted in FIGS. 2A to 2D.

2. An isolated nucleic acid consisting essentially of a sequence selected from the group consisting of:

(a) SEQ ID NO:4, as depicted in FIGS. 2A to 2D, or degenerate variants thereof that encode the same amino acid sequence as SEQ ID NO:4, encodes;

(b) SEQ ID NO:4, as depicted in FIGS. 2A to 2D, or degenerate variants thereof that encode the same amino acid sequence as SEQ ID NO:4 encodes, wherein T is replaced by U;

(c) SEQ ID NO:6; and (d) SEQ ID NO:6, wherein T is replaced by U.

3. An isolated nucleic acid from Aspergillus consisting essentially of the nucleic acid sequence set forth as SEQ ID NO:4, and encoding an AN80 polypeptide.

4. An isolated nucleic acid molecule, said molecule comprising the cDNA sequence contained within American Type Culture Collection (ATCC) accession number 209484.

5. A vector comprising the nucleic acid of claim 1.

6. A vector comprising the nucleic acid of claim 2.

7. An expression vector comprising the nucleic acid of claim 1 operably linked to a nucleotide sequence regulatory element that controls expression of said nucleic acid.

8. An expression vector comprising the nucleic acid of claim 2, operably linked to a nucleotide sequence regulatory element that controls expression of said nucleic acid.

9. A genetically engineered host cell comprising the nucleic acid of claim 1.

10. A genetically engineered host cell comprising the nucleic acid of claim 2.

11. The host cell of claim 9, wherein the cell is a yeast or bacterium.

12. The host cell of claim 10, wherein the cell is a yeast or bacterium.

13. A genetically engineered host cell comprising the nucleic acid of claim 1 operably linked to a nucleotide sequence regulatory element that controls expression of the nucleic acid in the host cell.

14. The host cell of claim 13, wherein the cell is a yeast or bacterium.

15. A genetically engineered host cell comprising the nucleic acid of claim 2 operably linked to a nucleotide sequence regulatory element that controls expression of the nucleic acid in the host cell.

16. The host cell of claim 15 wherein the cell is a yeast or bacterium.

17. A method for identifying an antifungal agent, the method comprising:

(a) contacting a nucleic acid encoding an AN80 polypeptide with a test compound, wherein the AN80 polypeptide has the amino acid sequence set forth as SEQ ID NO:5;

(b) detecting binding of the test compound to the nucleic acid; and (c) determining whether a test compound that binds to the nucleic acid inhibits growth of fungi, relative to growth of fungi cultured in the absence of the test compound that binds to the nucleic acid, wherein inhibition of growth is an indication that the test compound is an antifungal agent.

18. The method of claim 17, wherein the test compound is selected from the group consisting of polypeptides, small molecules, ribonucleic acids, and deoxyribonucleic acids.

19. The method of claim 17, wherein the test compound is an antisense oligonucleotide.

20. The method of claim 17, wherein the test compound is a ribozyme.

21. A method for identifying an antifungal agent, the method comprising:

(a) contacting the nucleic acid of claim 2 with a test compound;

(b) detecting binding of the test compound to the nucleic acid; and (c) determining whether a test compound that binds to the nucleic acid inhibits growth of fungi, relative to growth of fungi cultured in the absence of the test compound that binds to the nucleic acid, wherein inhibition of growth indicates that the test compound is an antifungal agent.

22. The method of claim 21, wherein the test compound is selected from the group consisting of polypeptides, small molecules, ribonucleic acids, and deoxyribonucleic acids.

23. The method of claim 21, wherein the test compound is an antisense molecule.

24. The method of claim 21, wherein the test compound is a ribozyme.

* * * * *

SEQUENCE LISTING

```
<160> NUMBER OF SEQ ID NOS: 35

<210> SEQ ID NO 1
<211> LENGTH: 5596
<212> TYPE: DNA
<213> ORGANISM: Aspergillus nidulans
<220> FEATURE:
<221> NAME/KEY: CDS
<222> LOCATION: (604)...(2655)
<221> NAME/KEY: CDS
<222> LOCATION: (2706)...(3992)

<400> SEQUENCE: 1
agcgctgcgc agggcagctg tggcaaatcg ccggacgctt tggcgaaaca tcctgtcaat      60
atcaatgctg ctcctgaaac agaaaagac aagacgaagt tccccggatt gtatctcgaa     120
```

-continued

```
tgagggggacc gatttccggc gttagtaaga ggtcacgtga aagatggcgt gctaactagt    180
atgcaaggca tttcggctca ggcaaaatac ccagtcaaca atttgttgcc tggaggtgga    240
aatacgagac ccttgattgc gagcagtgtg tgattaggat agctgaggca ttgtattcat    300
gtatcaggaa cctgatcgtc aaagcgttgc aggctgctgg gctgggcacg tgctgcccta    360
acccttatct atctactggt ttggggtgtt tgtttatgct ccgccccgtg actctcagca    420
acggttataa cgagtagtgg cagcagccaa cgaacttctt tgctgccgac ctcacgccaa    480
acaaaagcct ttactggaaa caggctgatc agcaaatcaa gatatactag gatgagttga    540
tattatcacc ggccgcagat tactgacccg acacccttac tgcgtcatta ccctcgatc     600
```

```
aag atg ccg agt cga gtt tcc gcc cgt tca aca tcc acc gcc tcg cgc    648
    Met Pro Ser Arg Val Ser Ala Arg Ser Thr Ser Thr Ala Ser Arg
     1               5                  10                  15 aaa ggc tct aca cag act gcg aca agc ggt cgc gct ggc tca gcg acc    696
Lys Gly Ser Thr Gln Thr Ala Thr Ser Gly Arg Ala Gly Ser Ala Thr
             20                  25                  30 cca tca ttc gcc atc cca gag gaa act gca tta ccc gag gct gtt cca    744
Pro Ser Phe Ala Ile Pro Glu Glu Thr Ala Leu Pro Glu Ala Val Pro
         35                  40                  45 acc ctt cgc cgc gat gta tgc gcc att ttc gcg gat gcc cag cgt tcg    792
Thr Leu Arg Arg Asp Val Cys Ala Ile Phe Ala Asp Ala Gln Arg Ser
     50                  55                  60 act gcc ggt cat cgc aaa ctt gtc gtc cga cta agg aaa atc cag gag    840
Thr Ala Gly His Arg Lys Leu Val Val Arg Leu Arg Lys Ile Gln Glu
 65                  70                  75 gtg tgc tgt gct ata ccc cag aag aac tcc aaa aaa gac agt tca act    888
Val Cys Cys Ala Ile Pro Gln Lys Asn Ser Lys Lys Asp Ser Ser Thr
 80                  85                  90                  95 gaa gag cga ttg att ccc ggc gaa gag acg gta cca gaa aag gag ttc    936
Glu Glu Arg Leu Ile Pro Gly Glu Glu Thr Val Pro Glu Lys Glu Phe
                100                 105                 110 aac gtc gaa gta agt cgt tgt gtg ttg cgc atc ttg tct att aag aag    984
Asn Val Glu Val Ser Arg Cys Val Leu Arg Ile Leu Ser Ile Lys Lys
             115                 120                 125 aca gag cct gtt ggc gat cga atc ctg cgg ttt ctc ggg aac ttc ctt   1032
Thr Glu Pro Val Gly Asp Arg Ile Leu Arg Phe Leu Gly Asn Phe Leu
         130                 135                 140 act cat gcc tcg gaa aag gac gct gag atc ttc ggc tct gaa gaa gat   1080
Thr His Ala Ser Glu Lys Asp Ala Glu Ile Phe Gly Ser Glu Glu Asp
     145                 150                 155 gaa gac gat atg cag aat tcg cac gaa aga ccg act gcc cac ttg acc   1128
Glu Asp Asp Met Gln Asn Ser His Glu Arg Pro Thr Ala His Leu Thr
160                 165                 170                 175 acc agt ctt gtc tcc ctg tta gtg cct ttg ttg tct gca aaa gac aag   1176
Thr Ser Leu Val Ser Leu Leu Val Pro Leu Leu Ser Ala Lys Asp Lys
                180                 185                 190 gtt gtg cgc ttc cgt acc acg caa att atc gcg cac atc gtc aat tca   1224
Val Val Arg Phe Arg Thr Thr Gln Ile Ile Ala His Ile Val Asn Ser
             195                 200                 205 ctc gat acc gta gac gac gaa tta tac cac act ctc cgg caa ggc ctt   1272
Leu Asp Thr Val Asp Asp Glu Leu Tyr His Thr Leu Arg Gln Gly Leu
         210                 215                 220 cta aaa cgg att cgc gac aaa gaa cct tcg gtg cgg gta caa gca gtg   1320
Leu Lys Arg Ile Arg Asp Lys Glu Pro Ser Val Arg Val Gln Ala Val
     225                 230                 235 atg ggt ctc ggc cgc ttg gcc gga aat gaa gag gac gat gac gaa aat   1368
Met Gly Leu Gly Arg Leu Ala Gly Asn Glu Glu Asp Asp Asp Glu Asn
240                 245                 250                 255
```

-continued

```
gat gat acc agt gcc ctt gtg gag aag ctc gtg gac ata atg caa aat    1416
Asp Asp Thr Ser Ala Leu Val Glu Lys Leu Val Asp Ile Met Gln Asn
            260                 265                 270 gac acg gct gca gag gtt cgg agg aca tta ctc ctc aac ctc cca ttg    1464
Asp Thr Ala Ala Glu Val Arg Arg Thr Leu Leu Leu Asn Leu Pro Leu
            275                 280                 285 att ccg tct acc ctt cca tac ctc ctc gaa cgc gcc cgt gac ctc gat    1512
Ile Pro Ser Thr Leu Pro Tyr Leu Leu Glu Arg Ala Arg Asp Leu Asp
            290                 295                 300 gct ccc aca cga agg gca tta tat tct cgt cta ctt ccg aca ctg gga    1560
Ala Pro Thr Arg Arg Ala Leu Tyr Ser Arg Leu Leu Pro Thr Leu Gly
            305                 310                 315 gat ttc cga cat tta tct ctc tcc atg aga gaa aag ttg ctc aga tgg    1608
Asp Phe Arg His Leu Ser Leu Ser Met Arg Glu Lys Leu Leu Arg Trp
320                 325                 330                 335 ggt ctt cgt gat cgc gac aaa agt gtg agg aag gcc act gga aag ttg    1656
Gly Leu Arg Asp Arg Asp Lys Ser Val Arg Lys Ala Thr Gly Lys Leu
                340                 345                 350 ttc tat gac cgc tgg att gag ata tcg ctg gca cga aca atg acc ctg    1704
Phe Tyr Asp Arg Trp Ile Glu Ile Ser Leu Ala Arg Thr Met Thr Leu
            355                 360                 365 aga att cgg gca gcg ctc gga acg aga att ccc gct tta ctg gag ttg    1752
Arg Ile Arg Ala Ala Leu Gly Thr Arg Ile Pro Ala Leu Leu Glu Leu
            370                 375                 380 ttg gag cgt atc gat gtg gtg aac tca ggc atg gaa tcc ggc ata gcg    1800
Leu Glu Arg Ile Asp Val Val Asn Ser Gly Met Glu Ser Gly Ile Ala
385                 390                 395 cac gaa gct atg cgc agt ttc tgg gaa ggt cga cca gac tat cga gag    1848
His Glu Ala Met Arg Ser Phe Trp Glu Gly Arg Pro Asp Tyr Arg Glu
400                 405                 410                 415 gcg gta cta ttc gac gaa gcc ttc tgg gag tca atg aca gca gaa tcc    1896
Ala Val Leu Phe Asp Glu Ala Phe Trp Glu Ser Met Thr Ala Glu Ser
                420                 425                 430 gct ttc ctc ctt cgc tca ttc aat gac ttt tgc cgg gtt gaa aac gaa    1944
Ala Phe Leu Leu Arg Ser Phe Asn Asp Phe Cys Arg Val Glu Asn Glu
            435                 440                 445 ggt aaa tat gac agc ctc gcc gat gag aag atc cca gtc gtt aca gcc    1992
Gly Lys Tyr Asp Ser Leu Ala Asp Glu Lys Ile Pro Val Val Thr Ala
450                 455                 460 ctc gca atg tat ctt cat aag tac atg acc gag ctg ctg cag cgc aag    2040
Leu Ala Met Tyr Leu His Lys Tyr Met Thr Glu Leu Leu Gln Arg Lys
465                 470                 475 aag ctc aca aag gat gct act gac gta aac gac gac gat acc gtc gaa    2088
Lys Leu Thr Lys Asp Ala Thr Asp Val Asn Asp Asp Asp Thr Val Glu
480                 485                 490                 495 atc gaa ttt atc gtc gag caa ctg ctt cac atc gcg atg aca cta gac    2136
Ile Glu Phe Ile Val Glu Gln Leu Leu His Ile Ala Met Thr Leu Asp
                500                 505                 510 tac agc gac gaa gtt ggg cgg cga aag atg ttt tct cta ctc cgt gag    2184
Tyr Ser Asp Glu Val Gly Arg Arg Lys Met Phe Ser Leu Leu Arg Glu
            515                 520                 525 gct ctc gct gtc cca gag ctc cct cag gaa tcg acc aag ctc gcg gtt    2232
Ala Leu Ala Val Pro Glu Leu Pro Gln Glu Ser Thr Lys Leu Ala Val
            530                 535                 540 gag aca ctg aga tgt gtt tgt ggg ccc gac gcc gcg gca gag agc gaa    2280
Glu Thr Leu Arg Cys Val Cys Gly Pro Asp Ala Ala Ala Glu Ser Glu
545                 550                 555 ttc tgc agt gtt gtt ctg gaa gcc att gct gaa gtt cat gac aca atc    2328
Phe Cys Ser Val Val Leu Glu Ala Ile Ala Glu Val His Asp Thr Ile
```

```
560                   565                   570                   575 agc acc gag gat agt ttc gtt tct gca aag tct gag att agc gat gat    2376
Ser Thr Glu Asp Ser Phe Val Ser Ala Lys Ser Glu Ile Ser Asp Asp
                580                   585                   590 gcc agc agc cgc caa cga tcc gaa acg ccg atg agt gaa gat gac aag    2424
Ala Ser Ser Arg Gln Arg Ser Glu Thr Pro Met Ser Glu Asp Asp Lys
                595                   600                   605 cca ttc aac aag gag gag gca aag gct aag gtc ctc aag gaa atc gtt    2472
Pro Phe Asn Lys Glu Glu Ala Lys Ala Lys Val Leu Lys Glu Ile Val
                610                   615                   620 att aat atg aag tgt ctg cac att gcc ctt tgc atg ctc cag aat gtt    2520
Ile Asn Met Lys Cys Leu His Ile Ala Leu Cys Met Leu Gln Asn Val
                625                   630                   635 gaa ggc aac ctg caa gca aat atg aat ctg gtg acc atg ttg aat aac    2568
Glu Gly Asn Leu Gln Ala Asn Met Asn Leu Val Thr Met Leu Asn Asn
640                   645                   650                   655 ttg gta gta cct gct gtt cgg agc cac gaa gcg cca att cga gag cgc    2616
Leu Val Val Pro Ala Val Arg Ser His Glu Ala Pro Ile Arg Glu Arg
                660                   665                   670 ggt ctc gaa tgt ctt ggg ctg tgc tgc ttg ctg gac aag gtaagttcca    2665
Gly Leu Glu Cys Leu Gly Leu Cys Cys Leu Leu Asp Lys
                675                   680 tccttactaa atacatcttc ttctctaacc tctctgttag act ctc gca gaa gaa    2720
                                              Thr Leu Ala Glu Glu
                                                            685 aat atg acg ctg ttt att cac tgt tac agc aag ggc cac gaa aac cta    2768
Asn Met Thr Leu Phe Ile His Cys Tyr Ser Lys Gly His Glu Asn Leu
690                   695                   700                   705 cag gtc act gct att cat atc ctt tgc gat atg tta att agc cat cct    2816
Gln Val Thr Ala Ile His Ile Leu Cys Asp Met Leu Ile Ser His Pro
                710                   715                   720 tcg ctg gtg gct ccc gtt acc cag gcc gat aag gag aca gtt gcg cca    2864
Ser Leu Val Ala Pro Val Thr Gln Ala Asp Lys Glu Thr Val Ala Pro
                725                   730                   735 ccg gcg ttc cag aag cca ctg ctt aag gtc ttt tcc aga gct ctc aaa    2912
Pro Ala Phe Gln Lys Pro Leu Leu Lys Val Phe Ser Arg Ala Leu Lys
                740                   745                   750 cca aat tca ccc gcg tct gta caa acg gca gct gcg aca gct ctt tct    2960
Pro Asn Ser Pro Ala Ser Val Gln Thr Ala Ala Ala Thr Ala Leu Ser
                755                   760                   765 aag ctt ctg ctc act ggt gtt ttt act cca tct gcc gcc aat atc ccc    3008
Lys Leu Leu Leu Thr Gly Val Phe Thr Pro Ser Ala Ala Asn Ile Pro
770                   775                   780                   785 gat gcc att caa gag ttc aac caa cat gcc atc gaa aca ctg cta cag    3056
Asp Ala Ile Gln Glu Phe Asn Gln His Ala Ile Glu Thr Leu Leu Gln
                790                   795                   800 tcc ctc gtt gtc tcc ttc ttc cat ccc cga act cgc gag aat ccc gca    3104
Ser Leu Val Val Ser Phe Phe His Pro Arg Thr Arg Glu Asn Pro Ala
                805                   810                   815 ctc cga cag gca ctc gcg tac ttc ttc cct gtc tac tgc cac tcc cgg    3152
Leu Arg Gln Ala Leu Ala Tyr Phe Phe Pro Val Tyr Cys His Ser Arg
                820                   825                   830 ccg gat aac acc cag cat atg aga aag att act gta cct gtc atc cgg    3200
Pro Asp Asn Thr Gln His Met Arg Lys Ile Thr Val Pro Val Ile Arg
                835                   840                   845 acc atc cta aac tca gcg gaa gaa tac tac tca ctt gag gct gaa gag    3248
Thr Ile Leu Asn Ser Ala Glu Glu Tyr Tyr Ser Leu Glu Ala Glu Glu
850                   855                   860                   865 gac agt gat ggt gat att gat gag tct gtt ggg gag aag gaa ttg aag    3296
```

```
Asp Ser Asp Gly Asp Ile Asp Glu Ser Val Gly Glu Lys Glu Leu Lys
            870                 875                 880 gcc ctg atg agc gga gtt ctt ggt atg ctt gcg gag tgg acg gat gag         3344
Ala Leu Met Ser Gly Val Leu Gly Met Leu Ala Glu Trp Thr Asp Glu
        885                 890                 895 cga aga gtg atc gga ctt ggc ggc gaa cgg gtc ctt gct ggg ggc ctt         3392
Arg Arg Val Ile Gly Leu Gly Gly Glu Arg Val Leu Ala Gly Gly Leu
900                 905                 910 gct agc tcc aat gtt tgt ggc att atc cac ttg caa ctg att aag gac         3440
Ala Ser Ser Asn Val Cys Gly Ile Ile His Leu Gln Leu Ile Lys Asp
        915                 920                 925 ata ctg gaa cga gtg ctc ggg atc agt gaa ggc agc aat cgc tgc tct         3488
Ile Leu Glu Arg Val Leu Gly Ile Ser Glu Gly Ser Asn Arg Cys Ser
930                 935                 940                 945 aaa caa caa cga aaa ctc ctg ttt tca ctc atg agc aag ctc tat att         3536
Lys Gln Gln Arg Lys Leu Leu Phe Ser Leu Met Ser Lys Leu Tyr Ile
            950                 955                 960 gcg ccg cca acg gca ctt tcg cgc tca gcg tcc cag gcc ccc gaa gac         3584
Ala Pro Pro Thr Ala Leu Ser Arg Ser Ala Ser Gln Ala Pro Glu Asp
        965                 970                 975 gac tcg ttc cgt tcc agc gtg cga agc tcc cat ggc gaa ctc aat ccc         3632
Asp Ser Phe Arg Ser Ser Val Arg Ser Ser His Gly Glu Leu Asn Pro
    980                 985                 990 gaa aac ctt gcc ctc gcg cag gaa gtc aag gag cta ctt gac cag acc         3680
Glu Asn Leu Ala Leu Ala Gln Glu Val Lys Glu Leu Leu Asp Gln Thr
        995                 1000                1005 atc gaa gaa ggt gtg gcg gct gat gct gct agc cga aat gcc ctc gtc         3728
Ile Glu Glu Gly Val Ala Ala Asp Ala Ala Ser Arg Asn Ala Leu Val
1010                1015                1020                1025 aag gtg aag aac gtg gtg ctc aag cta ctg gcg gct ccc atg cga cct         3776
Lys Val Lys Asn Val Val Leu Lys Leu Leu Ala Ala Pro Met Arg Pro
            1030                1035                1040 tct agc gca cgc ggc cgc gag agc agt gtc gaa agt gac att ggc agt         3824
Ser Ser Ala Arg Gly Arg Glu Ser Ser Val Glu Ser Asp Ile Gly Ser
        1045                1050                1055 gtt cga tct tcc aga agt gtt cgg ccg tcc gta gag cct ggc ttt ggg         3872
Val Arg Ser Ser Arg Ser Val Arg Pro Ser Val Glu Pro Gly Phe Gly
    1060                1065                1070 cgc cgc ggt gta tcc gtg gag ccc agt atc atg gag gag gat gag aat         3920
Arg Arg Gly Val Ser Val Glu Pro Ser Ile Met Glu Glu Asp Glu Asn
1075                1080                1085 gag gat agc cgg gcg act ctg gac agt aga atg act gtt atc aaa gag         3968
Glu Asp Ser Arg Ala Thr Leu Asp Ser Arg Met Thr Val Ile Lys Glu
1090                1095                1100                1105 gag gat gcc gac gct atg gag gaa tgattttcgg tctcaagatc tttgctgtct        4022
Glu Asp Ala Asp Ala Met Glu Glu
                    1110 ggttcggcgt tggggaggtt tcccggcagg gctaatggtc atatttatgg ttaggttgcg       4082 atgtaattat tcgattcttg gttatgcttg aacatgctct atatgttaca aataattcac       4142 tccaaacgtt catgtatgag tatggatctg ttttatattg gccttaccag gatagctcag       4202 ttcttggcga agttatccca gactgacagc tgcctccagg ccagaattgg ctagtcttag       4262 tcttaggtag catctgagtt atcgcgtggt atcaacagtg atcagtgtgg aagggccatc       4322 cgatctgttt gatcttacca gaacgtgtta caacaattca acccaccata tatatggtat       4382 ctacgtcaat gtgaatgaat ctgcttgggc agccttatga ctctggtgac gcgactcggg       4442 gcttgattca atgcgggcaa gaccgcatgt ggagactcct agcatcggat gtgaggcttc       4502
```

```
cgttttaatt tcttcctcca aatcgtctgc ctgcctcgct gctttgaaat actccggagg   4562
taccaaagta aagataaatg gttgactctg agagactgct ttgacctcct ggaccaagtc   4622
gtgcctagcc agaaggggag tgttcaatgg gctttgtgag gctactaagg ccgcacgata   4682
caccggagat gcaaagaagt ccgatacggt cgtccatatc tcgagcacct ttattactgg   4742
cgcttttgca gttatatgga ggcgtttaat gattgcgtgt tcggaatccg atgaataata   4802
tctcattagt cgactaaacg gggatgagga tggatgactg ctggtatctt ggtctcaaac   4862
tgtaataagc gtctcggcaa caccgtacgg ttgacaatcc tgggcagatg gcagcacctg   4922
tagaatccaa gaagacgcag ctggactcat tgagacagtt gaattcctta actataatga   4982
cagactaata atacaaaagt gcggtggtca acttcttccc aatcccctca aaagtcagac   5042
ccgaccctgt tctttctaat aatctgacgc tccaccaaaa gtccagcttc tgggcgactt   5102 tcttttctt ccccatcctt ttcctttccc actctcctcc ctcctctctc gcttctcttc   5162
ctttcgctgt atgttttttg ttgcttgatt cacgactttc ttttccttc tggtcgtgga   5222 tccgtgtctt ctgcccccac ttgcagaggc acgatttttc tccctctccc tctcctccct   5282
tccgtactcc ccccctcccc cctgctctgc gcctttggca tccggagcct gcgtcgagac   5342
cgtgagcgat ggcctccgtg tcagctccca cgcccaagct ggaccgctac atcgtcgttc   5402
atgtggcaac tacctgcgat gagcatggcg tctacgtcac caaggactct gcagagtgat   5462
cgagttgggg tggatcttgt tggataccaa aacctgcgag agtcgcagtg attctctccc   5522
tgcaccacac ctattccacc ccctcttttg tgtcttgatt ctcgccggcc taccgggatt   5582
ctgccgacga catt                                                     5596
```

<210> SEQ ID NO 2
<211> LENGTH: 684
<212> TYPE: PRT
<213> ORGANISM: Aspergillus nidulans

<400> SEQUENCE: 2

```
Met Pro Ser Arg Val Ser Ala Arg Ser Thr Ser Thr Ala Ser Arg Lys
  1               5                  10                  15

Gly Ser Thr Gln Thr Ala Thr Ser Gly Arg Ala Gly Ser Ala Thr Pro
             20                  25                  30

Ser Phe Ala Ile Pro Glu Glu Thr Ala Leu Pro Glu Ala Val Pro Thr
         35                  40                  45

Leu Arg Arg Asp Val Cys Ala Ile Phe Ala Asp Ala Gln Arg Ser Thr
     50                  55                  60

Ala Gly His Arg Lys Leu Val Val Arg Leu Arg Lys Ile Gln Glu Val
 65                  70                  75                  80

Cys Cys Ala Ile Pro Gln Lys Asn Ser Lys Lys Asp Ser Ser Thr Glu
                 85                  90                  95

Glu Arg Leu Ile Pro Gly Glu Glu Thr Val Pro Glu Lys Glu Phe Asn
            100                 105                 110

Val Glu Val Ser Arg Cys Val Leu Arg Ile Leu Ser Ile Lys Lys Thr
        115                 120                 125

Glu Pro Val Gly Asp Arg Ile Leu Arg Phe Leu Gly Asn Phe Leu Thr
    130                 135                 140

His Ala Ser Glu Lys Asp Ala Glu Ile Phe Gly Ser Glu Asp Glu
145                 150                 155                 160

Asp Asp Met Gln Asn Ser His Gly Arg Pro Thr Ala His Leu Thr Thr
                165                 170                 175
```

-continued

```
Ser Leu Val Ser Leu Leu Val Pro Leu Leu Ser Ala Lys Asp Lys Val
            180                 185                 190

Val Arg Phe Arg Thr Thr Gln Ile Ile Ala His Ile Val Asn Ser Leu
            195                 200                 205

Asp Thr Val Asp Asp Glu Leu Tyr His Thr Leu Arg Gln Gly Leu Leu
            210                 215                 220

Lys Arg Ile Arg Asp Lys Glu Pro Ser Val Arg Val Gln Ala Val Met
225                 230                 235                 240

Gly Leu Gly Arg Leu Ala Gly Asn Glu Glu Asp Asp Asp Glu Asn Asp
                245                 250                 255

Asp Thr Ser Ala Leu Val Glu Lys Leu Val Asp Ile Met Gln Asn Asp
            260                 265                 270

Thr Ala Ala Glu Val Arg Arg Thr Leu Leu Leu Asn Leu Pro Leu Ile
            275                 280                 285

Pro Ser Thr Leu Pro Tyr Leu Leu Glu Arg Ala Arg Asp Leu Asp Ala
            290                 295                 300

Pro Thr Arg Arg Ala Leu Tyr Ser Arg Leu Leu Pro Thr Leu Gly Asp
305                 310                 315                 320

Phe Arg His Leu Ser Leu Ser Met Arg Glu Lys Leu Leu Arg Trp Gly
                325                 330                 335

Leu Arg Asp Arg Asp Lys Ser Val Arg Lys Ala Thr Gly Lys Leu Phe
                340                 345                 350

Tyr Asp Arg Trp Ile Glu Ile Ser Leu Ala Arg Thr Met Thr Leu Arg
            355                 360                 365

Ile Arg Ala Ala Leu Gly Thr Arg Ile Pro Ala Leu Leu Glu Leu Leu
            370                 375                 380

Glu Arg Ile Asp Val Val Asn Ser Gly Met Glu Ser Gly Ile Ala His
385                 390                 395                 400

Glu Ala Met Arg Ser Phe Trp Glu Gly Arg Pro Asp Tyr Arg Glu Ala
                405                 410                 415

Val Leu Phe Asp Glu Ala Phe Trp Glu Ser Met Thr Ala Glu Ser Ala
                420                 425                 430

Phe Leu Leu Arg Ser Phe Asn Asp Phe Cys Arg Val Glu Asn Glu Gly
            435                 440                 445

Lys Tyr Asp Ser Leu Ala Asp Glu Lys Ile Pro Val Val Thr Ala Leu
            450                 455                 460

Ala Met Tyr Leu His Lys Tyr Met Thr Glu Leu Leu Gln Arg Lys Lys
465                 470                 475                 480

Leu Thr Lys Asp Ala Thr Asp Val Asn Asp Asp Thr Val Glu Ile
                485                 490                 495

Glu Phe Ile Val Glu Gln Leu Leu His Ile Ala Met Thr Leu Asp Tyr
            500                 505                 510

Ser Asp Glu Val Gly Arg Arg Lys Met Phe Ser Leu Leu Arg Glu Ala
            515                 520                 525

Leu Ala Val Pro Glu Leu Pro Gln Glu Ser Thr Lys Leu Ala Val Glu
            530                 535                 540

Thr Leu Arg Cys Val Cys Gly Pro Asp Ala Ala Ala Glu Ser Glu Phe
545                 550                 555                 560

Cys Ser Val Val Leu Glu Ala Ile Ala Glu Val His Asp Thr Ile Ser
                565                 570                 575

Thr Glu Asp Ser Phe Val Ser Ala Lys Ser Glu Ile Ser Asp Asp Ala
            580                 585                 590

Ser Ser Arg Gln Arg Ser Glu Thr Pro Met Ser Glu Asp Asp Lys Pro
```

-continued

```
                595                 600                 605

Phe Asn Lys Glu Glu Ala Lys Ala Lys Val Leu Lys Glu Ile Val Ile
            610                 615                 620

Asn Met Lys Cys Leu His Ile Ala Leu Cys Met Leu Gln Asn Val Glu
        625                 630                 635                 640

Gly Asn Leu Gln Ala Asn Met Asn Leu Val Thr Met Leu Asn Asn Leu
                        645                 650                 655

Val Val Pro Ala Val Arg Ser His Glu Ala Pro Ile Arg Glu Arg Gly
                    660                 665                 670

Leu Glu Cys Leu Gly Leu Cys Cys Leu Leu Asp Lys
                    675                 680

<210> SEQ ID NO 3
<211> LENGTH: 5596
<212> TYPE: DNA
<213> ORGANISM: Aspergillus nidulans

<400> SEQUENCE: 3
aatgtcgtcg gcagaatccc ggtaggccgg cgagaatcaa gacacaaaag aggggtgga          60 ataggtgtgg tgcagggaga gaatcactgc gactctcgca ggttttggta tccaacaaga       120
tccaccccaa ctcgatcact ctgcagagtc cttggtgacg tagacgccat gctcatcgca       180
ggtagttgcc acatgaacga cgatgtagcg gtccagcttg ggcgtgggag ctgacacgga       240
ggccatcgct cacggtctcg acgcaggctc cggatgccaa aggcgcagag caggggggag       300 gggggagta cggaagggag gagagggaga gggagaaaaa tcgtgcctct gcaagtgggg        360
gcagaagaca cggatccacg accagaagga aaagaaagt cgtgaatcaa gcaacaaaaa        420
acatacagcg aaaggaagag aagcgagaga ggagggagga gagtgggaaa ggaaaaggat       480
ggggaagaaa aagaaagtcg cccagaagct ggacttttgg tggagcgtca gattattaga      540
aagaacaggg tcgggtctga cttttgaggg gattgggaag aagttgacca ccgcactttt      600
gtattattag tctgtcatta tagttaagga attcaactgt ctcaatgagt ccagctgcgt      660
cttcttggat tctacaggtg ctgccatctg cccaggattg tcaaccgtac ggtgttgccg      720
agacgcttat tacagtttga gaccaagata ccagcagtca tccatcctca tcccgttta       780 gtcgactaat gagatattat tcatcggatt ccgaacacgc aatcattaaa cgcctccata       840
taactgcaaa agcgccagta ataaaggtgc tcgagatatg gacgaccgta tcggacttct       900
ttgcatctcc ggtgtatcgt gcggccttag tagcctcaca aagcccattg aacactcccc       960
ttctggctag gcacgacttg gtccaggagg tcaaagcagt ctctcagagt caaccattta     1020
tctttacttt ggtacctccg gagtatttca agcagcgag gcaggcagac gatttggagg      1080
aagaaattaa aacggaagcc tcacatccga tgctaggagt ctccacatgc ggtcttgccc     1140
gcattgaatc aagcccgag tcgcgtcacc agagtcataa ggctgcccaa gcagattcat     1200
tcacattgac gtagatacca tatatatggt gggttgaatt gttgtaacac gttctggtaa     1260
gatcaaacag atcggatggc ccttccacac tgatcactgt tgataccacg cgataactca     1320
gatgctacct aagactaaga ctagccaatt ctggcctgga ggcagctgtc agtctgggat     1380
aacttcgcca agaactgagc tatcctggta aggccaatat aaaacagatc catactcata     1440
catgaacgtt tggagtgaat tatttgtaac atatagagca tgttcaagca taccaagaa     1500 tcgaataatt acatcgcaac ctaaccataa atatgaccat tagccctgcc gggaaacctc    1560
cccaacgccg aaccagacag caaagatctt gagaccgaaa atcattcctc catagcgtcg    1620
```

-continued

```
gcatcctcct ctttgataac agtcattcta ctgtccagag tcgcccggct atcctcattc    1680
tcatcctcct ccatgatact gggctccacg gatacaccgc ggcgcccaaa gccaggctct    1740
acggacggcc gaacacttct ggaagatcga acactgccaa tgtcactttc gacactgctc    1800
tcgcggccgc gtgcgctaga aggtcgcatg ggagccgcca gtagcttgag caccacgttc    1860
ttcaccttga cgagggcatt tcggctagca gcatcagccg ccacaccttc ttcgatggtc    1920
tggtcaagta gctccttgac ttcctgcgcg agggcaaggt tttcgggatt gagttcgcca    1980
tgggagcttc gcacgctgga acggaacgag tcgtcttcgg gggcctggga cgctgagcgc    2040
gaaagtgccg ttggcggcgc aatatagagc ttgctcatga gtgaaaacag gagttttcgt    2100
tgttgtttag agcagcgatt gctgccttca ctgatcccga gcactcgttc cagtatgtcc    2160
ttaatcagtt gcaagtggat aatgccacaa acattggagc tagcaaggcc cccagcaagg    2220
acccgttcgc cgccaagtcc gatcactctt cgctcatccg tccactccgc aagcatacca    2280
agaactccgc tcatcagggc cttcaattcc ttctccccaa cagactcatc aatatcacca    2340
tcactgtcct cttcagcctc aagtgagtag tattcttccg ctgagtttag gatggtccgg    2400
atgacaggta cagtaatctt tctcatatgc tgggtgttat ccggccggga gtggcagtag    2460
acagggaaga agtacgcgag tgcctgtcga agtgcgggat tctcgcgagt tcggggatgg    2520
aagaaggaga caacgaggga ctgtagcagt gtttcgatgg catgttggtt gaactcttga    2580
atggcatcgg ggatattggc ggcagatgga gtaaaaacac cagtgagcag aagcttagaa    2640
agagctgtcg cagctgccgt ttgtacagac gcgggtgaat ttggtttgag agctctggaa    2700
aagaccttaa gcagtggctt ctggaacgcc ggtggcgcaa ctgtctcctt atcggcctgg    2760
gtaacgggag ccaccagcga aggatggcta attaacatat cgcaaaggat atgaatagca    2820
gtgacctgta ggttttcgtg gcccttgctg taacagtgaa taaacagcgt catattttct    2880
tctgcgagag tctaacagag aggttagaga agaagatgta tttagtaagg atggaactta    2940
ccttgtccag caagcagcac agcccaagac attcgagacc gcgctctcga attggcgctt    3000
cgtggctccg aacagcaggt actaccaagt tattcaacat ggtcaccaga ttcatatttg    3060
cttgcaggtt gccttcaaca ttctggagca tgcaaagggc aatgtgcaga cacttcatat    3120
taataacgat ttccttgagg accttagcct ttgcctcctc cttgttgaat ggcttgtcat    3180
cttcactcat cggcgtttcg gatcgttggc ggctgctggc atcatcgcta atctcagact    3240
ttgcagaaac gaaactatcc tcggtgctga ttgtgtcatg aacttcagca atggcttcca    3300
gaacaacact gcagaattcg ctctctgccg cggcgtcggg cccacaaaca catctcagtg    3360
tctcaaccgc gagcttggtc gattcctgag ggagctctgg gacagcgaga gcctcacgga    3420
gtagagaaaa catctttcgc cgcccaactt cgtcgctgta gtctagtgtc atcgcgatgt    3480
gaagcagttg ctcgacgata aattcgattt cgacggtatc gtcgtcgttt acgtcagtag    3540
catcctttgt gagcttcttg cgctgcagaa gctcggtcat gtacttatga agatacattg    3600
cgagggctgt aacgactggg atcttctcat cggcgaggct gtcatattta ccttcgtttt    3660
caacccggca aaagtcattg aatgagcgaa ggaggaaagc ggattctgct gtcattgact    3720
cccagaaggc ttcgtcgaat agtaccgcct ctcgatagtc tggtcgacct tcccagaaac    3780
tgcgcatagc ttcgtgcgct atgccggatt ccatgcctga gttcaccaca tcgatacgct    3840
ccaacaactc cagtaaagcg ggaattctcg ttccgagcgc tgcccgaatt ctcagggtca    3900
ttgttcgtgc cagcgatatc tcaatccagc ggtcatagaa caacttttcca gtggccttcc    3960 tcacactttt gtcgcgatca cgaagacccc atctgagcaa cttttctctc atggagagag    4020
```

-continued

```
ataaatgtcg gaaatctccc agtgtcggaa gtagacgaga atataatgcc cttcgtgtgg      4080
gagcatcgag gtcacgggcg cgttcgagga ggtatggaag ggtagacgga atcaatggga      4140
ggttgaggag taatgtcctc cgaacctctg cagccgtgtc attttgcatt atgtccacga      4200
gcttctccac aagggcactg gtatcatcat tttcgtcatc gtcctcttca tttccggcca      4260
agcggccgag acccatcact gcttgtaccc gcaccgaagg ttctttgtcg cgaatccgtt      4320
ttagaaggcc ttgccggaga gtgtggtata attcgtcgtc tacggtatcg agtgaattga      4380
cgatgtgcgc gataatttgc gtggtacgga agcgcacaac cttgtctttt gcagacaaca      4440
aaggcactaa cagggagaca agactggtgg tcaagtgggc agtcggtctt tcgtgcgaat      4500
tctgcatatc gtcttcatct tcttcagagc cgaagatctc agcgtccttt tccgaggcat      4560
gagtaaggaa gttcccgaga accgcagga ttcgatcgcc aacaggctct gtcttcttaa       4620
tagacaagat gcgcaacaca caacgactta cttcgacgtt gaactccttt tctggtaccg      4680
tctcttcgcc gggaatcaat cgctcttcag ttgaactgtc ttttttggag ttcttctggg      4740
gtatagcaca gcacacctcc tggatttttcc ttagtcggac gacaagtttg cgatgaccgg     4800
cagtcgaacg ctgggcatcc gcgaaaatgg cgcatacatc gcggcgaagg gttggaacag     4860
cctcgggtaa tgcagtttcc tctgggatgg cgaatgatgg ggtcgctgag ccagcgcgac     4920
cgcttgtcgc agtctgtgta gagcctttgc gcgaggcggt ggatgttgaa cgggcggaaa     4980
ctcgactcgg catcttgatc gagggtaat gacgcagtaa gggtgtcggg tcagtaatct      5040
gcggccggtg ataatatcaa ctcatcctag tatatcttga tttgctgatc agcctgtttc      5100
cagtaaaggc ttttgtttgg cgtgaggtcg gcagcaaaga agttcgttgg ctgctgccac     5160
tactcgttat aaccgttgct gagagtcacg gggcggagca taaacaaaca ccccaaacca    5220
gtagatagat aagggttagg gcagcacgtg cccagcccag cagcctgcaa cgctttgacg     5280
atcaggttcc tgatacatga atacaatgcc tcagctatcc taatcacaca ctgctcgcaa    5340
tcaagggtct cgtatttcca cctccaggca acaaattgtt gactgggtat tttgcctgag   5400
ccgaaatgcc ttgcatacta gttagcacgc catctttcac gtgacctctt actaacgccg    5460
gaaatcggtc ccctcattcg agatacaatc cggggaactt cgtcttgtct ttttctgttt    5520
caggagcagc attgatattg acaggatgtt tcgccaaagc gtccggcgat ttgccacagc    5580
tgccctgcgc agcgct                                                     5596
```

```
<210> SEQ ID NO 4
<211> LENGTH: 1758
<212> TYPE: DNA
<213> ORGANISM: Aspergillus nidulans
<220> FEATURE:
<221> NAME/KEY: CDS
<222> LOCATION: (162)...(1319)

<400> SEQUENCE: 4
caaaagtctt gatcacaggg gcacaagcgc aattgagcca ccatgcttac ggacggcatc      60 gaagggtca aggagaaagt ctttgtgctc gtgaccggtg ccaacaggta cagtgaaacc      120
ctgcgctctg tctcctatct catgcggtcc gttagtggtt t atg ttt cta act gtt    176
                                              Met Phe Leu Thr Val
                                                1               5 acc cct tgt ggg ttt tca ccg ttt agc gga cta gga tac tca acg tgt       224
Thr Pro Cys Gly Phe Ser Pro Phe Ser Gly Leu Gly Tyr Ser Thr Cys
         10                  15                  20 tgc cgt ctt gca gat gaa ttc ctg gcg tct cat cgg aac gac cat cgt       272
```

```
Cys Arg Leu Ala Asp Glu Phe Leu Ala Ser His Arg Asn Asp His Arg
            25                  30                  35 tca ttg aca atc atc ttc act acc cgg agc aca aga aag gga agc gac        320
Ser Leu Thr Ile Ile Phe Thr Thr Arg Ser Thr Arg Lys Gly Ser Asp
        40                  45                  50 acc ctt cgc aac cta cag aat cac ctc cgc acc tcc acc ttc ggt gct        368
Thr Leu Arg Asn Leu Gln Asn His Leu Arg Thr Ser Thr Phe Gly Ala
55                  60                  65 tcg gcc acc gct cga gtg acc ttc gtt cct gaa aat gtc gac ctc tgc        416
Ser Ala Thr Ala Arg Val Thr Phe Val Pro Glu Asn Val Asp Leu Cys
70                  75                  80                  85 aac ctc ctc tcg gtc cgc gcg cta tcc cgt cgc ctg aac aag acc ttc        464
Asn Leu Leu Ser Val Arg Ala Leu Ser Arg Arg Leu Asn Lys Thr Phe
                90                  95                  100 cca aaa ctc gac gcg att gtg ctt aat gcc ggg ata ggg ggt tgg tct        512
Pro Lys Leu Asp Ala Ile Val Leu Asn Ala Gly Ile Gly Gly Trp Ser
            105                 110                 115 ggc ctc aat tgg cct ctg gcc gta tgg agc gtt tgc acc gac att atc        560
Gly Leu Asn Trp Pro Leu Ala Val Trp Ser Val Cys Thr Asp Ile Ile
        120                 125                 130 cat gcg acg acg tgg cca aag tac aaa att gcg cct gta ggt ctc ata        608
His Ala Thr Thr Trp Pro Lys Tyr Lys Ile Ala Pro Val Gly Leu Ile
135                 140                 145 acg gac aac cag aca att act gtg acc gac aag gag ccc cgc ctg gga        656
Thr Asp Asn Gln Thr Ile Thr Val Thr Asp Lys Glu Pro Arg Leu Gly
150                 155                 160                 165 acc gtc ttc tgc gcc aac gtc ttc ggc cac tac atg ctc gcg cat aat        704
Thr Val Phe Cys Ala Asn Val Phe Gly His Tyr Met Leu Ala His Asn
                170                 175                 180 gtc atg cct ctc ctg cac cga tcc gga tcc ccc aac gga ccc gga cgc        752
Val Met Pro Leu Leu His Arg Ser Gly Ser Pro Asn Gly Pro Gly Arg
            185                 190                 195 gtg ata tgg ctc tcc agc act gaa gcc acg atc aac ttc ttc gat gtt        800
Val Ile Trp Leu Ser Ser Thr Glu Ala Thr Ile Asn Phe Phe Asp Val
        200                 205                 210 gat gat ttt cag gcg ctc cgg tcc aaa gct ccc tac gag tca tca aaa        848
Asp Asp Phe Gln Ala Leu Arg Ser Lys Ala Pro Tyr Glu Ser Ser Lys
215                 220                 225 gcg cta aca gac ctc cta tcc ctc acc tca gac ctt ccc agt act gct        896
Ala Leu Thr Asp Leu Leu Ser Leu Thr Ser Asp Leu Pro Ser Thr Ala
230                 235                 240                 245 ccc tgg gtg aaa agc ttc tat tcc acc gac ttc gaa acc gat tcc aag        944
Pro Trp Val Lys Ser Phe Tyr Ser Thr Asp Phe Glu Thr Asp Ser Lys
                250                 255                 260 ccc agc acc gga cct gag acc gcc tcg acc ata ccc aac gta tac ctc        992
Pro Ser Thr Gly Pro Glu Thr Ala Ser Thr Ile Pro Asn Val Tyr Leu
            265                 270                 275 tct cac ccc gga atc tgc gct acg gcg att ata ccc ctt cct aca atc       1040
Ser His Pro Gly Ile Cys Ala Thr Ala Ile Ile Pro Leu Pro Thr Ile
        280                 285                 290 ctc atc tac gca atg gtc gcc gca ttt tgg cta gcc cgc atc ctc ggc       1088
Leu Ile Tyr Ala Met Val Ala Ala Phe Trp Leu Ala Arg Ile Leu Gly
295                 300                 305 tcc cct tgg cat acc tta tcc acc tac cta ggc gct tgc agc cct gtc       1136
Ser Pro Trp His Thr Leu Ser Thr Tyr Leu Gly Ala Cys Ser Pro Val
310                 315                 320                 325 tgg ctt gct ctc tcc aca caa tca gaa ctc gac gcc gcc gaa gca ccg       1184
Trp Leu Ala Leu Ser Thr Gln Ser Glu Leu Asp Ala Ala Glu Ala Pro
                330                 335                 340
```

-continued

```
tac cgg aaa cac ggc ggc agg gtg aaa tgg ggg tct tcg gcg tct    1232
Tyr Arg Lys His Gly Gly Arg Val Lys Trp Gly Ser Ser Ala Ser
        345                 350                 355 cga tta ggt gta gcc tcc gtc gta tct tcg gag gtt gac gga tgg ggc    1280
Arg Leu Gly Val Ala Ser Val Val Ser Ser Glu Val Asp Gly Trp Gly
360                 365                 370 tat ggg ggt gtt cct ggg gcc ggc tgt tgt ggc gga gga tagggtctga    1329
Tyr Gly Gly Val Pro Gly Ala Gly Cys Cys Gly Gly Gly
    375                 380             385 aggcgcaagc gtggtgcagt ggatcttacg gctgagggga aggagggatt ccaggaactg    1389
ggggctatat gttggaggca gatggaggag ctgaggatcc tgtgggataa cttacttgat    1449
gaagagagaa ggggactggt gtgacggcgt aggtggcttg tcctgggagt gagatctctt    1509
acatttcggc cttcgtccct aaaatccttt tctcccttcc tctttattat acgatgtcgg    1569
cggttttatg ttcaatacag cacatctacg gtacaaagac aacatatagc taatataata    1629
tcatagataa tagtaataat caagcacaaa agctcgattc tgcaagatct caatatcttt    1689
attccagttt tcactgctct tgtcttccat atttacattc cacgtccacg tgcatccttt    1749
aaaaacagt                                                          1758
```

<210> SEQ ID NO 5
<211> LENGTH: 386
<212> TYPE: PRT
<213> ORGANISM: Aspergillus nidulans

<400> SEQUENCE: 5

```
Met Phe Leu Thr Val Thr Pro Cys Gly Phe Ser Pro Phe Ser Gly Leu
1               5                   10                  15

Gly Tyr Ser Thr Cys Cys Arg Leu Ala Asp Glu Phe Leu Ala Ser His
            20                  25                  30

Arg Asn Asp His Arg Ser Leu Thr Ile Ile Phe Thr Thr Arg Ser Thr
        35                  40                  45

Arg Lys Gly Ser Asp Thr Leu Arg Asn Leu Gln Asn His Leu Arg Thr
    50                  55                  60

Ser Thr Phe Gly Ala Ser Ala Thr Ala Arg Val Thr Phe Val Pro Glu
65                  70                  75                  80

Asn Val Asp Leu Cys Asn Leu Leu Ser Val Arg Ala Leu Ser Arg Arg
                85                  90                  95

Leu Asn Lys Thr Phe Pro Lys Leu Asp Ala Ile Val Leu Asn Ala Gly
            100                 105                 110

Ile Gly Gly Trp Ser Gly Leu Asn Trp Pro Leu Ala Val Trp Ser Val
        115                 120                 125

Cys Thr Asp Ile Ile His Ala Thr Thr Trp Pro Lys Tyr Lys Ile Ala
130                 135                 140

Pro Val Gly Leu Ile Thr Asp Asn Gln Thr Ile Thr Val Thr Asp Lys
145                 150                 155                 160

Glu Pro Arg Leu Gly Thr Val Phe Cys Ala Asn Val Phe Gly His Tyr
                165                 170                 175

Met Leu Ala His Asn Val Met Pro Leu Leu His Arg Ser Gly Ser Pro
            180                 185                 190

Asn Gly Pro Gly Arg Val Ile Trp Leu Ser Ser Thr Glu Ala Thr Ile
        195                 200                 205

Asn Phe Phe Asp Val Asp Asp Phe Gln Ala Leu Arg Ser Lys Ala Pro
    210                 215                 220

Tyr Glu Ser Ser Lys Ala Leu Thr Asp Leu Leu Ser Leu Thr Ser Asp
```

```
225                 230                 235                 240
Leu Pro Ser Thr Ala Pro Trp Val Lys Ser Phe Tyr Ser Thr Asp Phe
                245                 250                 255
Glu Thr Asp Ser Lys Pro Ser Thr Gly Pro Glu Thr Ala Ser Thr Ile
                260                 265                 270
Pro Asn Val Tyr Leu Ser His Pro Gly Ile Cys Ala Thr Ala Ile Ile
                275                 280                 285
Pro Leu Pro Thr Ile Leu Ile Tyr Ala Met Val Ala Ala Phe Trp Leu
            290                 295                 300
Ala Arg Ile Leu Gly Ser Pro Trp His Thr Leu Ser Thr Tyr Leu Gly
305                 310                 315                 320
Ala Cys Ser Pro Val Trp Leu Ala Leu Ser Thr Gln Ser Glu Leu Asp
                325                 330                 335
Ala Ala Glu Ala Pro Tyr Arg Lys His Gly Gly Gly Arg Val Lys Trp
                340                 345                 350
Gly Ser Ser Ala Ser Arg Leu Gly Val Ala Ser Val Val Ser Ser Glu
                355                 360                 365
Val Asp Gly Trp Gly Tyr Gly Val Pro Gly Ala Gly Cys Cys Gly
            370                 375                 380
Gly Gly
385

<210> SEQ ID NO 6
<211> LENGTH: 1758
<212> TYPE: DNA
<213> ORGANISM: Aspergillus nidulans

<400> SEQUENCE: 6
actgttttta aaggatgcac gtggacgtgg aatgtaaata tggaagacaa gagcagtgaa      60
aactggaata aagatattga gatcttgcag aatcgagctt ttgtgcttga ttattactat    120
tatctatgat attatattag ctatatgttg tctttgtacc gtagatgtgc tgtattgaac    180
ataaaaccgc cgacatcgta taataaagag gaagggagaa aaggattta gggacgaagg     240
ccgaaatgta agagatctca ctcccaggac aagccaccta cgccgtcaca ccagtcccct    300
tctctcttca tcaagtaagt tatcccacag gatcctcagc tcctccatct gcctccaaca    360
tatagccccc agttcctgga atccctcctt ccctcagcc gtaagatcca ctgcaccacg    420
cttgcgcctt cagaccctat cctccgccac aacagccggc cccaggaaca cccccatagc    480
cccatccgtc aacctccgaa gatacgacgg aggctacacc taatcgagac gccgaagacc    540
cccatttcac cctgccgccg ccgtgtttcc ggtacggtgc ttcggcggcg tcgagttctg    600
attgtgtgga gagagcaagc cagacagggc tgcaagcgcc taggtaggtg gataaggtat    660
gccaagggga gccgaggatg cgggctagcc aaaatgcggc gaccattgcg tagatgagga    720
ttgtaggaag gggtataatc gccgtagcgc agattccggg gtgagagagg tatacgttgg    780
gtatggtcga ggcggtctca ggtccggtgc tgggcttgga atcggtttcg aagtcggtgg    840
aatagaagct tttcacccag ggagcagtac tgggaaggtc tgaggtgagg gataggaggt    900
ctgttagcgc ttttgatgac tcgtaggag ctttggaccg gagcgcctga aaatcatcaa     960
catcgaagaa gttgatcgtg gcttcagtgc tggagagcca tatcacgcgt ccgggtccgt   1020
tggggatcc ggatcggtgc aggagaggca tgacattatg cgcgagcatg tagtggccga    1080
agacgttggc gcagaagacg gttccaggc gggctcctt gtcggtcaca gtaattgtct     1140
ggttgtccgt tatgagacct acaggcgcaa ttttgtactt tggccacgtc gtcgcatgga   1200
```

-continued

```
taatgtcggt gcaaacgctc catacggcca gaggccaatt gaggccagac caaccccta     1260 tcccggcatt aagcacaatc gcgtcgagtt ttgggaaggt cttgttcagg cgacgggata    1320
gcgcgcggac cgagaggagg ttgcagaggt cgacattttc aggaacgaag gtcactcgag    1380
cggtggccga agcaccgaag gtggaggtgc ggaggtgatt ctgtaggttg cgaagggtgt    1440
cgcttccctt tcttgtgctc cgggtagtga agatgattgt caatgaacga tggtcgttcc    1500
gatgagacgc caggaattca tctgcaagac ggcaacacgt tgagtatcct agtccgctaa    1560
acggtgaaaa cccacaaggg gtaacagtta gaaacataaa ccactaacgg accgcatgag    1620
ataggagaca gagcgcaggg tttcactgta cctgttggca ccggtcacga gcacaaagac    1680
tttctccttg accccttcga tgccgtccgt aagcatggtg gctcaattgc gcttgtgccc    1740
ctgtgatcaa gacttttg                                                  1758
```

<210> SEQ ID NO 7
<211> LENGTH: 1792
<212> TYPE: DNA
<213> ORGANISM: Aspergillus nidulans
<220> FEATURE:
<221> NAME/KEY: CDS
<222> LOCATION: (230)...(309)
<221> NAME/KEY: CDS
<222> LOCATION: (375)...(815)
<221> NAME/KEY: CDS
<222> LOCATION: (876)...(1149)
<221> NAME/KEY: CDS
<222> LOCATION: (1200)...(1475)

<400> SEQUENCE: 7

```
gaattcctgt gatggagcag aacctcggag tatgctccga tgtcagtaca ttaaattttg      60
tagcgatcca cgtgatttct attttgcgtc cgcaataggt cttctgatac ggctgaagaa     120
atatagtacg tggtccagtg cctatagacg gaaagtattt tcgtacggtt ggctcccaag     180
gcaataggtc aacctcgcat acggagaata acggtacggt cctgaagga atg agg gga    238
                                                       Met Arg Gly
                                                         1 tgt att ctc ctt ctc cga ggg cca gaa ggg gaa cag gcc cgc act gat        286
Cys Ile Leu Leu Leu Arg Gly Pro Glu Gly Glu Gln Ala Arg Thr Asp
   5                  10                  15 ccg gcg aaa att tcc cct ctc ga gtcttcgctc tccccccac acggctgact        339
Pro Ala Lys Ile Ser Pro Leu Asp
 20                  25 aaccccttcca ttcttgcccg catccagcca gccag c ctt ttg tcg ccg ccc ttg      393
                                        Leu Leu Ser Pro Pro Leu
                                                            30 gtt cgg gct act gtc atc ttc cct tct tca tct tca tgc cgc tct cga        441
Val Arg Ala Thr Val Ile Phe Pro Ser Ser Ser Ser Cys Arg Ser Arg
 35                  40                  45 ctg aaa tat tca gtc tct tgc tct gat tta cag tta cta cgc gca gac        489
Leu Lys Tyr Ser Val Ser Cys Ser Asp Leu Gln Leu Leu Arg Ala Asp
 50                  55                  60                  65 acg ctg cac atc tcc gcg atc atg acc gaa tcc act caa gaa cag ggc        537
Thr Leu His Ile Ser Ala Ile Met Thr Glu Ser Thr Gln Glu Gln Gly
                 70                  75                  80 aac gat ggc cag cga atg ccc ccc gcc ccg gcg acc ccc gtt gag gat        585
Asn Asp Gly Gln Arg Met Pro Pro Ala Pro Ala Thr Pro Val Glu Asp
     85                  90                  95 tac gtc ttc cct gaa tat cgc ctg aag cgt gtg atg gat gac ccg gaa        633
Tyr Val Phe Pro Glu Tyr Arg Leu Lys Arg Val Met Asp Asp Pro Glu
         100                 105                 110
```

-continued

```
aag acg ccg cta ttg ctt ata gct tgc ggt tca ttc tca cct att acg    681
Lys Thr Pro Leu Leu Ile Ala Cys Gly Ser Phe Ser Pro Ile Thr
    115                 120                 125 ttc ctg cac ctg cgc atg ttc gaa atg gcc gcc gat tac gtc aaa ctg    729
Phe Leu His Leu Arg Met Phe Glu Met Ala Ala Asp Tyr Val Lys Leu
130                 135                 140                 145 agc aca gat ttc gaa ata att gga ggt tat ctt tcg ccc gtc tcg gac    777
Ser Thr Asp Phe Glu Ile Ile Gly Gly Tyr Leu Ser Pro Val Ser Asp
                150                 155                 160 gcc tac cgc aag gca ggt ctt gcg agt gcc aat cac ag gtagttactt      825
Ala Tyr Arg Lys Ala Gly Leu Ala Ser Ala Asn His Arg
                165                 170 taacacactt cttccatagt tactatccag gactgatctg gcggctttag a att gca   882
                                                         Ile Ala
                                                            175 atg tgc caa cga gcc gtg gac caa acg tca gac tgg atg atg gtg gat    930
Met Cys Gln Arg Ala Val Asp Gln Thr Ser Asp Trp Met Met Val Asp
            180                 185                 190 aca tgg gag ccg atg cac aag gag tac cag cca act gcc atc gta ctg    978
Thr Trp Glu Pro Met His Lys Glu Tyr Gln Pro Thr Ala Ile Val Leu
        195                 200                 205 gat cat ttt gac tac gag atc aac act gtc cgc aaa ggt atc gat acc    1026
Asp His Phe Asp Tyr Glu Ile Asn Thr Val Arg Lys Gly Ile Asp Thr
    210                 215                 220 gga aaa ggc act cga aag cga gtg caa gtc gtc tta ttg gcc ggg gca    1074
Gly Lys Gly Thr Arg Lys Arg Val Gln Val Val Leu Leu Ala Gly Ala
225                 230                 235                 240 gat ttg gtc cat acc atg tct acg ccc gga gta tgg agt gag aag gat    1122
Asp Leu Val His Thr Met Ser Thr Pro Gly Val Trp Ser Glu Lys Asp
                245                 250                 255 ctc gat cat att ctt gga cag tac ggg gtatgttatg ttgtatctat          1169
Leu Asp His Ile Leu Gly Gln Tyr Gly
                260                 265 cctaaacttc gcgcaagcta actggtctag act ttc atc gtc gag cga agc ggg   1223
                                Thr Phe Ile Val Glu Arg Ser Gly
                                                            270 aca gat att gac gag gcg ctc gcg gca ttg cag cca tgg aaa aag aat    1271
Thr Asp Ile Asp Glu Ala Leu Ala Ala Leu Gln Pro Trp Lys Lys Asn
    275                 280                 285 atc cat gtt att caa caa ctt att caa aat gac gtt agc agc act aag    1319
Ile His Val Ile Gln Gln Leu Ile Gln Asn Asp Val Ser Ser Thr Lys
290                 295                 300                 305 att cgc tta ttc ctc agg cga gat atg agc gta cgc tac ttg atc cct    1367
Ile Arg Leu Phe Leu Arg Arg Asp Met Ser Val Arg Tyr Leu Ile Pro
                310                 315                 320 gac ccg gtg att gag tac atc tat gag aat aac ctc tac atg gac gac    1415
Asp Pro Val Ile Glu Tyr Ile Tyr Glu Asn Asn Leu Tyr Met Asp Asp
            325                 330                 335 ggt acg aca caa ccg acg gcc gac aag ggc aag aca cga gag gag ccc    1463
Gly Thr Thr Gln Pro Thr Ala Asp Lys Gly Lys Thr Arg Glu Glu Pro
        340                 345                 350 gcg cct tca aat tagcattgct caaaaagcca gataaggcca cgcgacgacg        1515
Ala Pro Ser Asn
    355 tcatgacgac cattgctggt ttcacgaaga tatcaaaccg ccgggcgaat gcaatctctg  1575 cgctgatctg agcaagcact gattccggta agccgcaagt tggggagga tttaatgagc   1635 ccaaccgtat gggtttgttc cggtcaagtc actgcgatta acgacacgcc ttatgactgt  1695
```

-continued

```
catatcgaca ggtccctctc cagagccggc ctacacaaca gtgatgctgg cgttcttcta    1755
ttccaagccc tcaacatcta agtgcagcgg cgaattc                             1792
```

<210> SEQ ID NO 8
<211> LENGTH: 27
<212> TYPE: PRT
<213> ORGANISM: Aspergillus nidulans

<400> SEQUENCE: 8

```
Met Arg Gly Cys Ile Leu Leu Leu Arg Gly Pro Glu Gly Glu Gln Ala
 1               5                  10                  15

Arg Thr Asp Pro Ala Lys Ile Ser Pro Leu Asp
            20                  25
```

<210> SEQ ID NO 9
<211> LENGTH: 1792
<212> TYPE: DNA
<213> ORGANISM: Aspergillus nidulans

<400> SEQUENCE: 9

```
gaattcgccg ctgcacttag atgttgaggg cttggaatag aagaacgcca gcatcactgt      60
tgtgtaggcc ggctctggag agggacctgt cgatatgaca gtcataaggc gtgtcgttaa     120
tcgcagtgac ttgaccggaa caaacccata cggttgggct cattaaatcc tcccccaact     180
tgcggcttac cggaatcagt gcttgctcag atcagcgcag agattgcatt cgcccggcgg     240
tttgatatct tcgtgaaacc agcaatggtc gtcatgacgt cgtcgcgtgg ccttatctgg     300 cttttttgagc aatgctaatt tgaaggcgcg ggctcctctc gtgtcttgcc cttgtcggcc    360
gtcggttgtg tcgtaccgtc gtccatgtag aggttattct catagatgta ctcaatcacc     420
gggtcaggga tcaagtagcg tacgctcata tctcgcctga ggaataagcg aatcttagtg     480
ctgctaacgt cattttgaat aagttgttga ataacatgga tattcttttt ccatggctgc     540
aatgccgcga gcgcctcgtc aatatctgtc ccgcttcgct cgacgatgaa agtctagacc     600
agttagcttg cgcgaagttt aggatagata aacataaca taccccgtac tgtccaagaa     660
tatgatcgag atccttctca ctccatactc cgggcgtaga catggtatgg accaaatctg     720
ccccggccaa taagacgact tgcactcgct ttcgagtgcc ttttccggta tcgataccctt   780 tgcggacagt gttgatctcg tagtcaaaat gatccagtac gatggcagtt ggctggtact     840
ccttgtgcat cggctcccat gtatccacca tcatccagtc tgacgtttgg tccacggctc     900
gttggcacat tgcaattcta aagccgccag atcagtcctg gatagtaact atggaagaag     960
tgtgttaaag taactacctg tgattggcac tcgcaagacc tgccttgcgg taggcgtccg    1020
agacgggcga aagataacct ccaattattt cgaaatctgt gctcagtttg acgtaatcgg    1080
cggccatttc gaacatgcgc aggtgcagga acgtaatagg tgagaatgaa ccgcaagcta    1140
taagcaatag cggcgtcttt tccgggtcat ccatcacacg cttcaggcga tattcaggga    1200
agacgtaatc ctcaacgggg gtcgccgggg cgggggcat tcgctggcca tcgttgccct     1260
gttcttgagt ggattcggtc atgatcgcgg agatgtgcag cgtgtctgcg cgtagtaact    1320
gtaaatcaga gcaagagact gaatatttca gtcgagagcg gcatgaagat gaagaaggga    1380
agatgacagt agcccgaacc aagggcggcg acaaaaggct ggctggctgg atgcgggcaa    1440
gaatggaagg gttagtcagc cgtgtggggg ggagagcgaa gactcgagag gggaaatttt    1500
cgccggatca gtgcgggcct gttcccttc tggccctcgg agaaggagaa tacatcccct    1560
cattccttca ggaccgtacc gttattctcc gtatgcgagg ttgacctatt gccttgggag    1620
```

-continued

```
ccaaccgtac gaaaatactt tccgtctata ggcactggac cacgtactat atttcttcag      1680
ccgtatcaga agacctattg cggacgcaaa atagaaatca cgtggatcgc tacaaaattt      1740
aatgtactga catcggagca tactccgagg ttctgctcca tcacaggaat tc              1792

<210> SEQ ID NO 10
<211> LENGTH: 1899
<212> TYPE: DNA
<213> ORGANISM: Aspergillus nidulans
<220> FEATURE:
<221> NAME/KEY: CDS
<222> LOCATION: (453)...(627)
<221> NAME/KEY: CDS
<222> LOCATION: (686)...(890)
<221> NAME/KEY: CDS
<222> LOCATION: (949)...(1157)
<221> NAME/KEY: CDS
<222> LOCATION: (1212)...(1288)

<400> SEQUENCE: 10
ttgccttctt agacttgata tctgaaggaa tataacggaa gagatcatct ggtttgatgg        60
tactgtatta gcgggagcac gtgattattt ccctccgata ggccagtggc gtatgtcata      120
aggaagactg acgcctggag gggaaaaacac ctccctcgcc cgagttccat cttatcactt      180
tcacgctcga tctctccaag tttctggctt cattgactga gtcgctcgcc ttgcctagtg      240
ggtagattta gatctagtcg caaatcactt gcctacattc tcgaacctgt ttgttcagcc      300
ttgcggttcc cctcactact tatctcttct taccttctac cgtttcgaaa acacttcctc      360
ctgcggcgag actagtatct atcgcctgtc gcccactttc accaccgtgt ttcactagga      420
gaatagtgaa agactcaagt cgtctaccaa aa atg tgg tca tgg ttc cgg tgg         473
                                  Met Trp Ser Trp Phe Arg Trp
                                   1               5 tgc ggc cgc gca gaa gcg caa gga agc gcc gaa aac gca atc ctc cag         521
Cys Gly Arg Ala Glu Ala Gln Gly Ser Ala Glu Asn Ala Ile Leu Gln
         10                  15                  20 ctt cga agc cac ctt gac atg cta cag aag cga gaa aag cac cta gaa         569
Leu Arg Ser His Leu Asp Met Leu Gln Lys Arg Glu Lys His Leu Glu
     25                  30                  35 aac caa atg aac gaa caa gag gcc atc gct aaa aag aac gtg acc acg         617
Asn Gln Met Asn Glu Gln Glu Ala Ile Ala Lys Lys Asn Val Thr Thr
 40                  45                  50                  55 aat aag aac g gtgtgtatat tatgggaccct ttatacaagt tcccatgctg              667
Asn Lys Asn atttgaccac caccgcag cc gcc aaa gcc gcg ctc cga cgg aaa aag gtg          717
                   Ala Ala Lys Ala Ala Leu Arg Arg Lys Lys Val
                                60                  65 cac gag aag aac tta gaa cag acg cag gct cag att gta cag ctt gag         765
His Glu Lys Asn Leu Glu Gln Thr Gln Ala Gln Ile Val Gln Leu Glu
 70                  75                  80                  85 cag cag ata tac tct att gaa gcc gcc aat att aac cac gag acc ctg         813
Gln Gln Ile Tyr Ser Ile Glu Ala Ala Asn Ile Asn His Glu Thr Leu
             90                  95                 100 gcc gcc atg aag gcc gcc ggt gca gct atg gag aag att cac aac ggc         861
Ala Ala Met Lys Ala Ala Gly Ala Ala Met Glu Lys Ile His Asn Gly
        105                 110                 115 atg acc gtc gaa cag gtc gac gag aca at gtacgtccct tactgtaccg            910
Met Thr Val Glu Gln Val Asp Glu Thr Met
    120                 125 ctggtgacat accggaattg gcatgctaac agactcag g gac aaa ctg cgg gaa         964
                                         Asp Lys Leu Arg Glu
```

```
                                      130
caa caa gcc atc aac gac gaa atc gcg att gcc atc aca aac ccg ggg       1012
Gln Gln Ala Ile Asn Asp Glu Ile Ala Ile Thr Asn Pro Gly
        135                 140                 145 ttc ggc gag cag gtg gac gaa gaa gat ctg gag gcg gaa ctc gag ggc       1060
Phe Gly Glu Gln Val Asp Glu Glu Asp Leu Glu Ala Glu Leu Glu Gly
    150                 155                 160 atg gag cag gag gct atg gac gag cgc atg ctc cac aca ggc aca gta       1108
Met Glu Gln Glu Ala Met Asp Glu Arg Met Leu His Thr Gly Thr Val
165                 170                 175                 180 cca gtt gca gat cag ctc aat cgg cta cct gcg cca gcg aat gca gaa       1156
Pro Val Ala Asp Gln Leu Asn Arg Leu Pro Ala Pro Ala Asn Ala Glu
                185                 190                 195 c gtaaggctct ccctttccca cctcaaaagc gaactccgac tgacagcctt              1207 ccag cc gcc aaa gcg aaa cag aaa gca gaa gaa gaa gac gag gaa gcc       1255
     Pro Ala Lys Ala Lys Gln Lys Ala Glu Glu Glu Asp Glu Glu Ala
                     200                 205                 210 gag ttg gag aag tta cgc gcg gaa atg gcc atg tgagagtggt cctggtgctt     1308
Glu Leu Glu Lys Leu Arg Ala Glu Met Ala Met
                215                 220 tggtctcttt ggtctaactt taatcttttt tcttcccct acacatatga tgaacaggga      1368
atcgttatca tgacgcacta cgattagcca agcactgtgt tcttttttccg tcggctcgtt   1428
gcgattcctt cttctccgcg gcgtaattac ttatctagtt gtaccaacta ccccgcgagg    1488
cttctgttga ggcgagagcg aaagcccaga cgtgtcgccc ttgccctgat tactggccac    1548
tcccgtccga gcacgctacc tccgttctgt ccacgctgtg tatcccactc tgtaataatc    1608
taccaagtga atacttttct ggatgatttg aagggcctat gtttcctacg ccatcatgtc    1668
attagatatg ttttgtggat catgtttccc cagcgcaatt gatgcccatt tgcagttcac    1728
actcgtgtca tatgaacctc agaatatgaa agccgcttct caacccagca aaacgtcact    1788
gaggattaaa attgagtaat tgagtaaaac taaattagta gctagataac tcccgtttcc    1848
caccagacct aacaccgtcc aaacagataa tcaacaagga aagaaagaa a              1899

<210> SEQ ID NO 11
<211> LENGTH: 59
<212> TYPE: PRT
<213> ORGANISM: Aspergillus nidulans

<400> SEQUENCE: 11

Met Trp Ser Trp Phe Arg Trp Cys Gly Arg Ala Glu Ala Gln Gly Ser
 1               5                  10                  15

Ala Glu Asn Ala Ile Leu Gln Leu Arg Ser His Leu Asp Met Leu Gln
            20                  25                  30

Lys Arg Glu Lys His Leu Glu Asn Gln Met Asn Glu Gln Glu Ala Ile
        35                  40                  45

Ala Lys Lys Asn Val Thr Thr Asn Lys Asn Ala
    50                  55

<210> SEQ ID NO 12
<211> LENGTH: 1899
<212> TYPE: DNA
<213> ORGANISM: Aspergillus nidulans

<400> SEQUENCE: 12
tttctttctt ttccttgttg attatctgtt tggacggtgt taggtctggt gggaaacggg     60
agttatctag ctactaattt agttttactc aattactcaa ttttaatcct cagtgacgtt    120
```

```
ttgctgggtt gagaagcggc tttcatattc tgaggttcat atgacacgag tgtgaactgc      180
aaatgggcat caattgcgct ggggaaacat gatccacaaa acatatctaa tgacatgatg      240
gcgtaggaaa cataggccct tcaaatcatc cagaaaagta ttcacttggt agattattac      300
agagtgggat acacagcgtg gacagaacga aggtagcgtg ctcggacggg agtggccagt      360
aatcagggca agggcgacac gtctgggctt cgctctcgc ctcaacagaa gcctcgcggg       420
gtagttggta caactagata agtaattacg ccgcggagaa gaaggaatcg caacgagccg      480
acggaaaaag aacacagtgc ttggctaatc gtagtgcgtc atgataacga ttccctgttc      540
atcatatgtg tagggggaag aaaaaagatt aaagttagac caaagagacc aaagcaccag      600
gaccactctc acatggccat ttccgcgcgt aacttctcca actcggcttc ctcgtcttct      660
tcttctgctt tctgtttcgc tttggcggct ggaaggctgt cagtcggagt tcgcttttga      720
ggtgggaaag ggagagcctt acgttctgca ttcgctggcg caggtagccg attgagctga      780
tctgcaactg gtactgtgcc tgtgtggagc atgcgctcgt ccatagcctc ctgctccatg      840
ccctcgagtt ccgcctccag atcttcttcg tccacctgct cgccgaaccc cgggtttgtg      900
atggcaatcg cgatttcgtc gttgatggct tgttgttccc gcagtttgtc cctgagtctg      960
ttagcatgcc aattccggta tgtcaccagc ggtacagtaa gggacgtaca ttgtctcgtc     1020
gacctgttcg acggtcatgc cgttgtgaat cttctccata gctgcaccgg cggccttcat     1080
ggcggccagg gtctcgtggt taatattggc ggcttcaata gagtatatct gctgctcaag     1140
ctgtacaatc tgagcctgcg tctgttctaa gttcttctcg tgcaccttt tccgtcggag      1200 cgcggctttg gcggctgcgg tggtggtcaa atcagcatgg gaacttgtat aaaggtccca     1260
taatatacac accgttctta ttcgtggtca cgttctttt agcgatggcc tcttgttcgt      1320
tcatttggtt ttctaggtgc tttttctcgct tctgtagcat gtcaaggtgg cttcgaagct     1380
ggaggattgc gttttcggcg cttccttgcg cttctgcgcg gccgcaccac cggaaccatg     1440
accacatttt tggtagacga cttgagtctt tcactattct cctagtgaaa cacggtggtg     1500
aaagtgggcg acaggcgata gatactagtc tcgccgcagg aggaagtgtt ttcgaaacgg     1560
tagaaggtaa gaagagataa gtagtgaggg gaaccgcaag gctgaacaaa caggttcgag     1620
aatgtaggca agtgatttgc gactagatct aaatctaccc actaggcaag gcgagcgact     1680
cagtcaatga agccagaaac ttggagagat cgagcgtgaa agtgataaga tggaactcgg     1740
gcgagggagg tgttttcccc tccaggcgtc agtcttcctt atgacatacg ccactggcct     1800
atcggaggga aataatcacg tgctcccgct aatacagtac catcaaacca gatgatctct     1860
tccgttatat tccttcagat atcaagtcta agaaggcaa                           1899
```

<210> SEQ ID NO 13
<211> LENGTH: 3800
<212> TYPE: DNA
<213> ORGANISM: Saccharomyces cerevisiae
<220> FEATURE:
<221> NAME/KEY: CDS
<222> LOCATION: (306)...(3458)

<400> SEQUENCE: 13

```
tttttcttgt cagtctgaaa attttttcatt tggttttttg aaaaaaatcc tgcctaatat      60
ggtatcaaga ggaataacaa gaaaaaaaaa tcatggggga tacaaaggaa acaaggaga      120 taatgcaggt tatactgaat tgctcatagt attagcctaa agcactttac ctctgattta     180
ttgcatctat cgtattcttg agttattgcg acttttaaaa tccgtgcacc gcatatgaaa     240
```

```
gggtagagcc ttcgtgtttg tttaccttt  tagctctttg aagatcaaac aaaaacactt          300 cagta atg cct aca gcc ttg gat aag aca aag aag tta aca gcc gcg ccc         350
      Met Pro Thr Ala Leu Asp Lys Thr Lys Lys Leu Thr Ala Ala Pro
      1               5                   10                  15 atc atg caa gat cct gat ggt att gac att aat acg aaa atc ttt aac           398
Ile Met Gln Asp Pro Asp Gly Ile Asp Ile Asn Thr Lys Ile Phe Asn
                20                  25                  30 tca gtt gct gaa gta ttt caa aag gca cag ggt tct tat gca gga cac           446
Ser Val Ala Glu Val Phe Gln Lys Ala Gln Gly Ser Tyr Ala Gly His
            35                  40                  45 agg aag cat ata gca gtt ttg aag aaa att cag tca aag gct gtt gag           494
Arg Lys His Ile Ala Val Leu Lys Lys Ile Gln Ser Lys Ala Val Glu
        50                  55                  60 caa ggc tat gaa gat gct ttt aac ttt tgg ttc gat aaa tta gtt act           542
Gln Gly Tyr Glu Asp Ala Phe Asn Phe Trp Phe Asp Lys Leu Val Thr
    65                  70                  75 aag atc ctt cct ctg aaa aag aat gag att atc gga gac agg ata gta           590
Lys Ile Leu Pro Leu Lys Lys Asn Glu Ile Ile Gly Asp Arg Ile Val
80                  85                  90                  95 aag tta gta gct gca ttt ata gct tct tta gaa agg gag ttg ata ttg           638
Lys Leu Val Ala Ala Phe Ile Ala Ser Leu Glu Arg Glu Leu Ile Leu
                100                 105                 110 gcc aaa aaa caa aac tat aag ctc acg aat gat gaa gaa ggg ata ttc           686
Ala Lys Lys Gln Asn Tyr Lys Leu Thr Asn Asp Glu Glu Gly Ile Phe
            115                 120                 125 tca agg ttc gtc gat cag ttc ata aga cat gtt ttg cgt ggt gtg gaa           734
Ser Arg Phe Val Asp Gln Phe Ile Arg His Val Leu Arg Gly Val Glu
        130                 135                 140 agc cct gac aag aac gtc aga ttt aga gtt tta cag tta tta gcc gtt           782
Ser Pro Asp Lys Asn Val Arg Phe Arg Val Leu Gln Leu Leu Ala Val
    145                 150                 155 ata atg gat aat ata ggg gaa atc gat gaa tca ctt ttc aat tta tta           830
Ile Met Asp Asn Ile Gly Glu Ile Asp Glu Ser Leu Phe Asn Leu Leu
160                 165                 170                 175 ata ttg tct tta aat aag agg att tat gat aga gaa cca acg gtt agg           878
Ile Leu Ser Leu Asn Lys Arg Ile Tyr Asp Arg Glu Pro Thr Val Arg
                180                 185                 190 ata cag gct gtg ttt tgt tta act aaa ttt cag gat gaa gag caa act           926
Ile Gln Ala Val Phe Cys Leu Thr Lys Phe Gln Asp Glu Glu Gln Thr
            195                 200                 205 gaa cat tta act gag ctt tct gat aat gaa gaa aat ttt gaa gct acg           974
Glu His Leu Thr Glu Leu Ser Asp Asn Glu Glu Asn Phe Glu Ala Thr
        210                 215                 220 aga act cta gtt gct tct atc cag aac gat ccg tca gct gaa gta cgg          1022
Arg Thr Leu Val Ala Ser Ile Gln Asn Asp Pro Ser Ala Glu Val Arg
    225                 230                 235 agg gct gca atg ctg aat ttg atc aat gat aat aat act aga ccg tat          1070
Arg Ala Ala Met Leu Asn Leu Ile Asn Asp Asn Asn Thr Arg Pro Tyr
240                 245                 250                 255 atc ttg gag agg gct aga gat gta aac atc gtt aat aga agg ctc gtg          1118
Ile Leu Glu Arg Ala Arg Asp Val Asn Ile Val Asn Arg Arg Leu Val
                260                 265                 270 tat tcg aga att ttg aaa tca atg gga aga aag tgt ttc gat gat att          1166
Tyr Ser Arg Ile Leu Lys Ser Met Gly Arg Lys Cys Phe Asp Asp Ile
            275                 280                 285 gag ccg cat att ttt gat caa ttg att gag tgg ggt tta gaa gat agg          1214
Glu Pro His Ile Phe Asp Gln Leu Ile Glu Trp Gly Leu Glu Asp Arg
        290                 295                 300
```

```
gaa tta tca gtg aga aat gcg tgt aag aga ctc att gct cat gat tgg   1262
Glu Leu Ser Val Arg Asn Ala Cys Lys Arg Leu Ile Ala His Asp Trp
    305                 310                 315 tta aat gct ctg gat ggc gat ttg ata gaa tta cta gaa aaa ttg gat   1310
Leu Asn Ala Leu Asp Gly Asp Leu Ile Glu Leu Leu Glu Lys Leu Asp
320                 325                 330                 335 gtc tca aga tcc tca gtg tgt gtt aag gct ata gaa gca ctt ttt caa   1358
Val Ser Arg Ser Ser Val Cys Val Lys Ala Ile Glu Ala Leu Phe Gln
                340                 345                 350 tca agg cca gat ata tta tct aaa atc aaa ttt cct gaa agt att tgg   1406
Ser Arg Pro Asp Ile Leu Ser Lys Ile Lys Phe Pro Glu Ser Ile Trp
            355                 360                 365 aaa gac ttt acc gta gaa att gcc ttc ctc ttt cgg gct att tat ttg   1454
Lys Asp Phe Thr Val Glu Ile Ala Phe Leu Phe Arg Ala Ile Tyr Leu
        370                 375                 380 tac tgt ttg gat aat aat ata aca gaa atg ctg gaa gaa aac ttt cca   1502
Tyr Cys Leu Asp Asn Asn Ile Thr Glu Met Leu Glu Glu Asn Phe Pro
385                 390                 395 gaa gcc tca aaa tta tcc gag cat tta aac cat tat att ctt ctc aga   1550
Glu Ala Ser Lys Leu Ser Glu His Leu Asn His Tyr Ile Leu Leu Arg
400                 405                 410                 415 tat cat cac aac gac att tct aat gac tct cag tcg cat ttt gat tat   1598
Tyr His His Asn Asp Ile Ser Asn Asp Ser Gln Ser His Phe Asp Tyr
                420                 425                 430 aac act tta gag ttt att att gag caa cta tcg att gcc gcc gaa agg   1646
Asn Thr Leu Glu Phe Ile Ile Glu Gln Leu Ser Ile Ala Ala Glu Arg
            435                 440                 445 tat gat tat agc gat gag gtt gga agg aga tcg atg ctt aca gtg gta   1694
Tyr Asp Tyr Ser Asp Glu Val Gly Arg Arg Ser Met Leu Thr Val Val
        450                 455                 460 cga aat atg ctg gcc tta act aca ctc tcc gaa cct ctt att aaa att   1742
Arg Asn Met Leu Ala Leu Thr Thr Leu Ser Glu Pro Leu Ile Lys Ile
465                 470                 475 ggt att cgt gta atg aaa agt ctg tcc ata aat gaa aaa gat ttt gta   1790
Gly Ile Arg Val Met Lys Ser Leu Ser Ile Asn Glu Lys Asp Phe Val
480                 485                 490                 495 aca atg gca ata gaa atc att aat gat att aga gac gac gat att gaa   1838
Thr Met Ala Ile Glu Ile Ile Asn Asp Ile Arg Asp Asp Asp Ile Glu
                500                 505                 510 aaa caa gaa caa gaa gag aaa ata aaa agc aag aag att aat cgc aga   1886
Lys Gln Glu Gln Glu Glu Lys Ile Lys Ser Lys Lys Ile Asn Arg Arg
            515                 520                 525 aat gag act tcc gtc gat gaa gag gac gaa aac ggc aca cat aat gac   1934
Asn Glu Thr Ser Val Asp Glu Glu Asp Glu Asn Gly Thr His Asn Asp
        530                 535                 540 gaa gtt aac gag gat gaa gaa gac gac aat att tca tcc ttc cat tct   1982
Glu Val Asn Glu Asp Glu Glu Asp Asp Asn Ile Ser Ser Phe His Ser
545                 550                 555 gct gta gaa aac tta gtg cag gga aac ggc aac gta tct gag agt gac   2030
Ala Val Glu Asn Leu Val Gln Gly Asn Gly Asn Val Ser Glu Ser Asp
560                 565                 570                 575 ata ata aat aat ctc cca ccc gaa aag gaa gcg tcc tca gca aca att   2078
Ile Ile Asn Asn Leu Pro Pro Glu Lys Glu Ala Ser Ser Ala Thr Ile
                580                 585                 590 gtt ctc tgt ctt aca agg tca tca tat atg cta gaa cta gtt aac aca   2126
Val Leu Cys Leu Thr Arg Ser Ser Tyr Met Leu Glu Leu Val Asn Thr
            595                 600                 605 ccg tta aca gaa aac att tta att gcg tcg ttg atg gac act ttg atc   2174
Pro Leu Thr Glu Asn Ile Leu Ile Ala Ser Leu Met Asp Thr Leu Ile
        610                 615                 620
```

```
aca cca gcg gtt aga aat acc gcg cca aat att agg gag ctt ggt gtc      2222
Thr Pro Ala Val Arg Asn Thr Ala Pro Asn Ile Arg Glu Leu Gly Val
    625                 630                 635 aag aac ctt ggt tta tgt tgt ctc ttg gat gtg aag ttg gct att gat      2270
Lys Asn Leu Gly Leu Cys Cys Leu Leu Asp Val Lys Leu Ala Ile Asp
640                 645                 650                 655 aac atg tac atc tta ggt atg tgc gtt tcg aaa ggt aat gca tca tta      2318
Asn Met Tyr Ile Leu Gly Met Cys Val Ser Lys Gly Asn Ala Ser Leu
                660                 665                 670 aag tat att gcg tta caa gtc att gta gat att ttt tcc gta cat ggg      2366
Lys Tyr Ile Ala Leu Gln Val Ile Val Asp Ile Phe Ser Val His Gly
            675                 680                 685 aac act gtg gta gac gga gaa ggc aaa gtt gac tca atc tcg ttg cac      2414
Asn Thr Val Val Asp Gly Glu Gly Lys Val Asp Ser Ile Ser Leu His
        690                 695                 700 aaa ata ttt tac aag gtt tta aag aat aac ggt tta ccg gaa tgt cag      2462
Lys Ile Phe Tyr Lys Val Leu Lys Asn Asn Gly Leu Pro Glu Cys Gln
    705                 710                 715 gtg ata gca gcg gag ggt tta tgc aaa cta ttt ttg gca gac gtg ttc      2510
Val Ile Ala Ala Glu Gly Leu Cys Lys Leu Phe Leu Ala Asp Val Phe
720                 725                 730                 735 act gat gat gat ttg ttt gaa acg ttg gtt ttg tca tat ttt tcg ccg      2558
Thr Asp Asp Asp Leu Phe Glu Thr Leu Val Leu Ser Tyr Phe Ser Pro
                740                 745                 750 ata aat tcc tca aac gaa gcg ctg gta cag gca ttt gcc ttc tgc att      2606
Ile Asn Ser Ser Asn Glu Ala Leu Val Gln Ala Phe Ala Phe Cys Ile
            755                 760                 765 cca gtc tat tgt ttt tca cat cct gct cat caa caa cgt atg tct agg      2654
Pro Val Tyr Cys Phe Ser His Pro Ala His Gln Gln Arg Met Ser Arg
        770                 775                 780 acg gct gcg gac ata ctc tta aga cta tgt gtt ctt tgg gac gat tta      2702
Thr Ala Ala Asp Ile Leu Leu Arg Leu Cys Val Leu Trp Asp Asp Leu
    785                 790                 795 cag agc tct gta ata cct gag gta gac cgt gaa gct atg cta aag cct      2750
Gln Ser Ser Val Ile Pro Glu Val Asp Arg Glu Ala Met Leu Lys Pro
800                 805                 810                 815 aac ata ata ttt caa cag ttg cta ttt tgg act gat cca cgt aac tta      2798
Asn Ile Ile Phe Gln Gln Leu Leu Phe Trp Thr Asp Pro Arg Asn Leu
                820                 825                 830 gtt aac cag aca ggt tca aca aaa aaa gat aca gtg cag ctt aca ttc      2846
Val Asn Gln Thr Gly Ser Thr Lys Lys Asp Thr Val Gln Leu Thr Phe
            835                 840                 845 ttg atc gat gtg ctc aaa ata tac gct caa att gag aag aaa gaa ata      2894
Leu Ile Asp Val Leu Lys Ile Tyr Ala Gln Ile Glu Lys Lys Glu Ile
        850                 855                 860 aag aag atg atc atc act aat ata aac gct ata ttt ctt tct tct gaa      2942
Lys Lys Met Ile Ile Thr Asn Ile Asn Ala Ile Phe Leu Ser Ser Glu
    865                 870                 875 caa gat tat tct act ttg aaa gaa ctt ctt gag tat tct gac gat att      2990
Gln Asp Tyr Ser Thr Leu Lys Glu Leu Leu Glu Tyr Ser Asp Asp Ile
880                 885                 890                 895 gca gaa aat gat aat tta gac aat gtt agc aaa aat gct ctg gac aag      3038
Ala Glu Asn Asp Asn Leu Asp Asn Val Ser Lys Asn Ala Leu Asp Lys
                900                 905                 910 cta agg aat aat ttg aat tcg ctg att gaa gag atc aat gaa agg tca      3086
Leu Arg Asn Asn Leu Asn Ser Leu Ile Glu Glu Ile Asn Glu Arg Ser
            915                 920                 925 gaa act cag aca aaa gat gag aac aac act gcg aat gac caa tac tcg      3134
Glu Thr Gln Thr Lys Asp Glu Asn Asn Thr Ala Asn Asp Gln Tyr Ser
```

```
                930              935              940
tct att ttg ggg aat tca ttc aat aaa tct tca aat gac acc ata gaa        3182
Ser Ile Leu Gly Asn Ser Phe Asn Lys Ser Ser Asn Asp Thr Ile Glu
    945              950              955 cac gct gct gat ata act gat gga aat aac aca gaa ttg act aaa aca        3230
His Ala Ala Asp Ile Thr Asp Gly Asn Asn Thr Glu Leu Thr Lys Thr
960              965              970              975 act gtt aat att tcg gca gtt gac aat aca aca gag caa agt aac tca        3278
Thr Val Asn Ile Ser Ala Val Asp Asn Thr Thr Glu Gln Ser Asn Ser
                980              985              990 agg aaa aga acg aga tca gaa gcg gag caa att gac aca tcc aaa aac        3326
Arg Lys Arg Thr Arg Ser Glu Ala Glu Gln Ile Asp Thr Ser Lys Asn
            995              1000             1005 ctg gaa aac atg agt att caa gac acg tca act gta gca aaa aat gta        3374
Leu Glu Asn Met Ser Ile Gln Asp Thr Ser Thr Val Ala Lys Asn Val
        1010             1015             1020 agt ttt gtt tta cct gac gag aaa tca gat gca atg tcc ata gat gaa        3422
Ser Phe Val Leu Pro Asp Glu Lys Ser Asp Ala Met Ser Ile Asp Glu
    1025             1030             1035 gaa gat aag gat tca gag tct ttc agc gag gtc tgt taaaattgat            3468
Glu Asp Lys Asp Ser Glu Ser Phe Ser Glu Val Cys
1040             1045             1050 atgcgagctc ttcatctatt taagttgatt ttttggttgt aaacatattt gtattttatt     3528
cttaggtttg ttaattcttc tacgcttacc agatatagat gctatatgtt attgcattac     3588
gcacattacc cggtgggaca aattatgaaa atattccaag gctataaatt ctttggtgaa     3648
aggaactgaa attatgtcca gtaatgcacc agaaatggac atataaaact attaatgcat     3708
tttattacaa ttatcctaag aaaatatcct atatataatt aaagtaaaag aataagatc     3768 aaaagaacaa aataaagtcg agtagaattt tc                                   3800

<210> SEQ ID NO 14
<211> LENGTH: 1051
<212> TYPE: PRT
<213> ORGANISM: Saccharomyces cerevisiae

<400> SEQUENCE: 14

Met Pro Thr Ala Leu Asp Lys Thr Lys Lys Leu Thr Ala Ala Pro Ile
 1               5                   10                  15

Met Gln Asp Pro Asp Gly Ile Asp Ile Asn Thr Lys Ile Phe Asn Ser
                20                  25                  30

Val Ala Glu Val Phe Gln Lys Ala Gln Gly Ser Tyr Ala Gly His Arg
            35                  40                  45

Lys His Ile Ala Val Leu Lys Lys Ile Gln Ser Lys Ala Val Glu Gln
        50                  55                  60

Gly Tyr Glu Asp Ala Phe Asn Phe Trp Phe Asp Lys Leu Val Thr Lys
65                  70                  75                  80

Ile Leu Pro Leu Lys Lys Asn Glu Ile Ile Gly Asp Arg Ile Val Lys
                85                  90                  95

Leu Val Ala Ala Phe Ile Ala Ser Leu Glu Arg Glu Leu Ile Leu Ala
            100                 105                 110

Lys Lys Gln Asn Tyr Lys Leu Thr Asn Asp Glu Glu Gly Ile Phe Ser
        115                 120                 125

Arg Phe Val Asp Gln Phe Ile Arg His Val Leu Arg Gly Val Glu Ser
    130                 135                 140

Pro Asp Lys Asn Val Arg Phe Arg Val Leu Gln Leu Ala Val Ile
145                 150                 155                 160
```

-continued

```
Met Asp Asn Ile Gly Glu Ile Asp Glu Ser Leu Phe Asn Leu Leu Ile
                165                 170                 175

Leu Ser Leu Asn Lys Arg Ile Tyr Asp Arg Glu Pro Thr Val Arg Ile
            180                 185                 190

Gln Ala Val Phe Cys Leu Thr Lys Phe Gln Asp Glu Glu Gln Thr Glu
            195                 200                 205

His Leu Thr Glu Leu Ser Asp Asn Glu Glu Asn Phe Glu Ala Thr Arg
            210                 215                 220

Thr Leu Val Ala Ser Ile Gln Asn Asp Pro Ser Ala Glu Val Arg Arg
225                 230                 235                 240

Ala Ala Met Leu Asn Leu Ile Asn Asp Asn Thr Arg Pro Tyr Ile
            245                 250                 255

Leu Glu Arg Ala Arg Asp Val Asn Ile Val Asn Arg Arg Leu Val Tyr
            260                 265                 270

Ser Arg Ile Leu Lys Ser Met Gly Arg Lys Cys Phe Asp Asp Ile Glu
            275                 280                 285

Pro His Ile Phe Asp Gln Leu Ile Glu Trp Gly Leu Glu Asp Arg Glu
            290                 295                 300

Leu Ser Val Arg Asn Ala Cys Lys Arg Leu Ile Ala His Asp Trp Leu
305                 310                 315                 320

Asn Ala Leu Asp Gly Asp Leu Ile Glu Leu Leu Glu Lys Leu Asp Val
                325                 330                 335

Ser Arg Ser Ser Val Cys Val Lys Ala Ile Glu Ala Leu Phe Gln Ser
            340                 345                 350

Arg Pro Asp Ile Leu Ser Lys Ile Lys Phe Pro Glu Ser Ile Trp Lys
            355                 360                 365

Asp Phe Thr Val Glu Ile Ala Phe Leu Phe Arg Ala Ile Tyr Leu Tyr
            370                 375                 380

Cys Leu Asp Asn Asn Ile Thr Glu Met Leu Glu Glu Asn Phe Pro Glu
385                 390                 395                 400

Ala Ser Lys Leu Ser Glu His Leu Asn His Tyr Ile Leu Leu Arg Tyr
                405                 410                 415

His His Asn Asp Ile Ser Asn Asp Ser Gln Ser His Phe Asp Tyr Asn
            420                 425                 430

Thr Leu Glu Phe Ile Ile Glu Gln Leu Ser Ile Ala Ala Glu Arg Tyr
            435                 440                 445

Asp Tyr Ser Asp Glu Val Gly Arg Arg Ser Met Leu Thr Val Val Arg
            450                 455                 460

Asn Met Leu Ala Leu Thr Thr Leu Ser Glu Pro Leu Ile Lys Ile Gly
465                 470                 475                 480

Ile Arg Val Met Lys Ser Leu Ser Ile Asn Glu Lys Asp Phe Val Thr
                485                 490                 495

Met Ala Ile Glu Ile Ile Asn Asp Ile Arg Asp Asp Ile Glu Lys
            500                 505                 510

Gln Glu Gln Glu Glu Lys Ile Lys Ser Lys Lys Ile Asn Arg Arg Asn
            515                 520                 525

Glu Thr Ser Val Asp Glu Glu Asp Glu Asn Gly Thr His Asn Asp Glu
            530                 535                 540

Val Asn Glu Asp Glu Glu Asp Asp Asn Ile Ser Ser Phe His Ser Ala
545                 550                 555                 560

Val Glu Asn Leu Val Gln Gly Asn Gly Asn Val Ser Glu Ser Asp Ile
                565                 570                 575
```

```
Ile Asn Asn Leu Pro Pro Glu Lys Glu Ala Ser Ser Ala Thr Ile Val
            580                 585                 590

Leu Cys Leu Thr Arg Ser Ser Tyr Met Leu Glu Leu Val Asn Thr Pro
            595                 600                 605

Leu Thr Glu Asn Ile Leu Ile Ala Ser Leu Met Asp Thr Leu Ile Thr
            610                 615                 620

Pro Ala Val Arg Asn Thr Ala Pro Asn Ile Arg Glu Leu Gly Val Lys
625                 630                 635                 640

Asn Leu Gly Leu Cys Cys Leu Leu Asp Val Lys Leu Ala Ile Asp Asn
                    645                 650                 655

Met Tyr Ile Leu Gly Met Cys Val Ser Lys Gly Asn Ala Ser Leu Lys
            660                 665                 670

Tyr Ile Ala Leu Gln Val Ile Asp Ile Phe Ser Val His Gly Asn
            675                 680                 685

Thr Val Val Asp Gly Glu Gly Lys Val Asp Ser Ile Ser Leu His Lys
            690                 695                 700

Ile Phe Tyr Lys Val Leu Lys Asn Asn Gly Leu Pro Glu Cys Gln Val
705                 710                 715                 720

Ile Ala Ala Glu Gly Leu Cys Lys Leu Phe Leu Ala Asp Val Phe Thr
                    725                 730                 735

Asp Asp Asp Leu Phe Glu Thr Leu Val Leu Ser Tyr Phe Ser Pro Ile
                740                 745                 750

Asn Ser Ser Asn Glu Ala Leu Val Gln Ala Phe Ala Phe Cys Ile Pro
            755                 760                 765

Val Tyr Cys Phe Ser His Pro Ala His Gln Arg Met Ser Arg Thr
            770                 775                 780

Ala Ala Asp Ile Leu Leu Arg Leu Cys Val Leu Trp Asp Asp Leu Gln
785                 790                 795                 800

Ser Ser Val Ile Pro Glu Val Asp Arg Glu Ala Met Leu Lys Pro Asn
                    805                 810                 815

Ile Ile Phe Gln Gln Leu Leu Phe Trp Thr Asp Pro Arg Asn Leu Val
                820                 825                 830

Asn Gln Thr Gly Ser Thr Lys Lys Asp Thr Val Gln Leu Thr Phe Leu
            835                 840                 845

Ile Asp Val Leu Lys Ile Tyr Ala Gln Ile Glu Lys Lys Glu Ile Lys
            850                 855                 860

Lys Met Ile Ile Thr Asn Ile Asn Ala Ile Phe Leu Ser Ser Glu Gln
865                 870                 875                 880

Asp Tyr Ser Thr Leu Lys Glu Leu Leu Glu Tyr Ser Asp Asp Ile Ala
                    885                 890                 895

Glu Asn Asp Asn Leu Asp Asn Val Ser Lys Asn Ala Leu Asp Lys Leu
                900                 905                 910

Arg Asn Asn Leu Asn Ser Leu Ile Glu Glu Ile Asn Glu Arg Ser Glu
            915                 920                 925

Thr Gln Thr Lys Asp Glu Asn Asn Thr Ala Asn Asp Gln Tyr Ser Ser
            930                 935                 940

Ile Leu Gly Asn Ser Phe Asn Lys Ser Ser Asn Asp Thr Ile Glu His
945                 950                 955                 960

Ala Ala Asp Ile Thr Asp Gly Asn Asn Thr Glu Leu Thr Lys Thr Thr
                    965                 970                 975

Val Asn Ile Ser Ala Val Asp Asn Thr Thr Glu Gln Ser Asn Ser Arg
                980                 985                 990

Lys Arg Thr Arg Ser Glu Ala Glu Gln Ile Asp Thr Ser Lys Asn Leu
```

-continued

```
           995                1000                1005
Glu Asn Met Ser Ile Gln Asp Thr Ser Thr Val Ala Lys Asn Val Ser
        1010                1015                1020

Phe Val Leu Pro Asp Glu Lys Ser Asp Ala Met Ser Ile Asp Glu Glu
1025                1030                1035                1040

Asp Lys Asp Ser Glu Ser Phe Ser Glu Val Cys
                1045                1050
```

<210> SEQ ID NO 15
<211> LENGTH: 3800
<212> TYPE: DNA
<213> ORGANISM: Saccharomyces cerevisiae

<400> SEQUENCE: 15

| | | | | | |
|---|---|---|---|---|---|
| gaaaattcta | ctcgactttta | ttttgttctt | ttgatcttat | ttcttttact | ttaattatat | 60 |
| ataggatatt | ttcttaggat | aattgtaata | aaatgcatta | atagtttat | atgtccattt | 120 |
| ctggtgcatt | actggacata | atttcagttc | ctttcaccaa | agaatttata | gccttggaat | 180 |
| atttccataa | tttgtcccac | cgggtaatgt | gcgtaatgca | ataacatata | gcatctatat | 240 |
| ctggtaagcg | tagaagaatt | aacaaaccta | agaataaaat | acaaatatgt | ttacaaccaa | 300 |
| aaaatcaact | taaatagatg | aagagctcgc | atatcaattt | taacagacct | cgctgaaaga | 360 |
| ctctgaatcc | ttatcttctt | catctatgga | cattgcatct | gatttctcgt | caggtaaaac | 420 |
| aaaacttaca | ttttttgcta | cagttgacgt | gtcttgaata | ctcatgtttt | ccaggttttt | 480 |
| ggatgtgtca | atttgctccg | cttctgatct | cgttcttttc | cttgagttac | tttgctctgt | 540 |
| tgtattgtca | actgccgaaa | tattaacagt | tgttttagtc | aattctgtgt | tatttccatc | 600 |
| agttatatca | gcagcgtgtt | ctatggtgtc | atttgaagat | ttattgaatg | aattccccaa | 660 |
| aatagacgag | tattggtcat | cgcagtgtt | gttctcatct | tttgtctgag | tttctgacct | 720 |
| ttcattgatc | tcttcaatca | gcgaattcaa | attattcctt | agcttgtcca | gagcattttt | 780 |
| gctaacattg | tctaaattat | cattttctgc | aatatcgtca | gaatactcaa | gaagttcttt | 840 |
| caaagtagaa | taatcttgtt | cagaagaaag | aaatatagcg | tttatattag | tgatgatcat | 900 |
| cttctttatt | tctttcttct | caatttgagc | gtatattttg | agcacatcga | tcaagaatgt | 960 |
| aagctgcact | gtatcttttt | ttgttgaacc | tgtctggtta | actaagttac | gtggatcagt | 1020 |
| ccaaaatagc | aactgttgaa | atattatgtt | aggctttagc | atagcttcac | ggtctaccct | 1080 |
| aggtattaca | gagctctgta | aatcgtccca | agaacacat | agtcttaaga | gtatgtccgc | 1140 |
| agccgtccta | gacatacgtt | gttgatgagc | aggatgtgaa | aaacaataga | ctggaatgca | 1200 |
| gaaggcaaat | gcctgtacca | gcgcttcgtt | tgaggaattt | atcggcgaaa | aatatgacaa | 1260 |
| aaccaacgtt | tcaaacaaat | catcatcagt | gaacacgtct | gccaaaaata | gtttgcataa | 1320 |
| accctccgct | gctatcacct | gacattccgg | taaaccgtta | ttctttaaaa | ccttgtaaaa | 1380 |
| tattttgtgc | aacgagattg | agtcaacttt | gccttctccg | tctaccacag | tgttcccatg | 1440 |
| tacggaaaaa | atatctacaa | tgacttgtaa | cgcaatatac | tttaatgatg | cattacctt | 1500 |
| cgaaacgcac | atacctaaga | tgtacatgtt | atcaatagcc | aacttcacat | ccaagagaca | 1560 |
| acataaacca | aggttcttga | caccaagctc | cctaatattt | ggcgcggtat | ttctaaccgc | 1620 |
| tggtgtgatc | aaagtgtcca | tcaacgacgc | aattaaaatg | ttttctgtta | acggtgtgtt | 1680 |
| aactagttct | agcatatatg | atgaccttgt | aagacagaga | acaattgttg | ctgaggacgc | 1740 |
| ttcctttttcg | ggtgggagat | tatttattat | gtcactctca | gatacgttgc | cgtttccctg | 1800 |

-continued

```
cactaagttt tctacagcag aatggaagga tgaaatattg tcgtcttctt catcctcgtt    1860
aacttcgtca ttatgtgtgc cgttttcgtc ctcttcatcg acggaagtct catttctgcg    1920
attaatcttc ttgcttttta ttttctcttc ttgttcttgt ttttcaatat cgtcgtctct    1980
aatatcatta atgatttcta ttgccattgt tacaaaatct ttttcattta tggacagact    2040
tttcattaca cgaataccaa ttttaataag aggttcggag agtgtagtta aggccagcat    2100
atttcgtacc actgtaagca tcgatctcct tccaacctca tcgctataat catacctttc    2160
ggcggcaatc gatagttgct caataataaa ctctaaagtg ttataatcaa aatgcgactg    2220
agagtcatta gaaatgtcgt tgtgatgata tctgagaaga atataatggt ttaaatgctc    2280
ggataatttt gaggcttctg gaaagttttc ttccagcatt tctgttatat tattatccaa    2340
acagtacaaa taaatagccc gaaagaggaa ggcaatttct acggtaaagt ctttccaaat    2400
actttcagga aatttgattt tagataatat atctggcctt gattgaaaaa gtgcttctat    2460
agccttaaca cacactgagg atcttgagac atccaatttt tctagtaatt ctatcaaatc    2520
gccatccaga gcatttaacc aatcatgagc aatgagtctc ttacacgcat ttctcactga    2580
taattcccta tcttctaaac cccactcaat caattgatca aaaatatgcg gctcaatatc    2640
atcgaaacac tttcttccca ttgatttcaa aattctcgaa tacacgagcc ttctattaac    2700
gatgtttaca tctctagccc tctccaagat atacggtcta gtattattat cattgatcaa    2760
attcagcatt gcagccctcc gtacttcagc tgacggatcg ttctggatag aagcaactag    2820
agttctcgta gcttcaaaat tttcttcatt atcagaaagc tcagttaaat gttcagtttg    2880
ctcttcatcc tgaaatttag ttaaacaaaa cacagcctgt atcctaaccg ttggttctct    2940
atcataaatc ctcttattta aagacaatat taataaattg aaaagtgatt catcgatttc    3000
ccctatatta tccattataa cggctaataa ctgtaaaact ctaaatctga cgttcttgtc    3060
agggctttcc acaccacgca aaacatgtct tatgaactga tcgacgaacc ttgagaatat    3120
cccttcttca tcattcgtga gcttatagtt ttgttttttg gccaatatca actccctttc    3180
taaagaagct ataaatgcag ctactaactt tactatcctg tctccgataa tctcattctt    3240
tttcagagga aggatcttag taactaattt atcgaaccaa aagttaaaag catcttcata    3300
gccttgctca acagcctttg actgaatttt cttcaaaact gctatatgct tcctgtgtcc    3360
tgcataagaa ccctgtgcct tttgaaatac ttcagcaact gagttaaaga ttttcgtatt    3420
aatgtcaata ccatcaggat cttgcatgat gggcgcggct gttaacttct ttgtcttatc    3480
caaggctgta ggcattactg aagtgttttt gtttgatctt caaagagcta aaaaggtaaa    3540
caaacacgaa ggctctaccc tttcatatgc ggtgcacgga ttttaaaagt cgcaataact    3600
caagaatacg atagatgcaa taaatcagag gtaaagtgct ttaggctaat actatgagca    3660
attcagtata acctgcatta tctccttgtt tccttttgta tcccccatga ttttttttc    3720 ttgttattcc tcttgatacc atattaggca ggattttttt caaaaaacca aatgaaaaat    3780
tttcagactg acaagaaaaa                                                3800
```

<210> SEQ ID NO 16
<211> LENGTH: 2156
<212> TYPE: DNA
<213> ORGANISM: Saccharomyces cerevisiae
<220> FEATURE:
<221> NAME/KEY: CDS
<222> LOCATION: (543)...(1727)

<400> SEQUENCE: 16

-continued

```
tcttttggtg tcaatggtgt attattccga gttactccag gctaggttca ggagtaccaa      60
gaatgtactt tatttattta tacaccggag caagtcatat aattacgcaa acgattcgaa     120
attgttaaaa gcaggatcaa cgtatctcat ttcttttga aagacgggta atagaaagtc      180
tctgagtcgc accccacatg gatatcgtac tattcgtata tggaatgtaa aatactcgca     240
atacgatttt atttagcttc acaatctctc aaacttatcg tcttgatcaa tctttacgtt     300
ttaccaaata atcgcctgtt tctggccatt ttttgcttat accatctacc atactcgctg     360
tccatatgtg acggtgtcgt ctccaagaaa ataacaatg taaattgacc cagcgtgacg      420
acagtagact gtaagttata gtacaatcat actctacctt agtcactgtt cctccactgt     480
taagtagaga gagagagaga gtttaaagtg gagaaggcaa gaaaaagtgc acttattacg     540
```

| ta atg gat ccc acc aaa gca ccc gat ttt aaa ccg cca cag cca aat | 587 |
| Met Asp Pro Thr Lys Ala Pro Asp Phe Lys Pro Pro Gln Pro Asn | |
| 1   5   10   15 | |

| gaa gaa cta caa cca ccg cca gat cca aca cat acg ata cca aaa tct | 635 |
| Glu Glu Leu Gln Pro Pro Pro Asp Pro Thr His Thr Ile Pro Lys Ser | |
| 20   25   30 | |

| gga ccc ata gtt cca tat gtt tta gct gat tat aat tct tcg atc gat | 683 |
| Gly Pro Ile Val Pro Tyr Val Leu Ala Asp Tyr Asn Ser Ser Ile Asp | |
| 35   40   45 | |

| gct cct ttc aat ctc gac att tac aaa acc ctg tcg tca agg aaa aaa | 731 |
| Ala Pro Phe Asn Leu Asp Ile Tyr Lys Thr Leu Ser Ser Arg Lys Lys | |
| 50   55   60 | |

| aac gcc aac tca agc aac cga atg gac cat att cca tta aat act agt | 779 |
| Asn Ala Asn Ser Ser Asn Arg Met Asp His Ile Pro Leu Asn Thr Ser | |
| 65   70   75 | |

| gac ttc cag cca cta tct cgg gat gta tca tcg gag gag gaa agt gaa | 827 |
| Asp Phe Gln Pro Leu Ser Arg Asp Val Ser Ser Glu Glu Glu Ser Glu | |
| 80   85   90   95 | |

| ggg caa tcg aat gga att gac gct act cta cag gat gtt acg atg act | 875 |
| Gly Gln Ser Asn Gly Ile Asp Ala Thr Leu Gln Asp Val Thr Met Thr | |
| 100   105   110 | |

| ggg aat ttg ggg gta ctg aag agc caa att gct gat ttg gaa gaa gtt | 923 |
| Gly Asn Leu Gly Val Leu Lys Ser Gln Ile Ala Asp Leu Glu Glu Val | |
| 115   120   125 | |

| cct cac aca att gta aga caa gcc aga act att gaa gat tac gaa ttt | 971 |
| Pro His Thr Ile Val Arg Gln Ala Arg Thr Ile Glu Asp Tyr Glu Phe | |
| 130   135   140 | |

| cct gta cac aga ttg acg aaa aag tta caa gat cct gaa aaa ctg cct | 1019 |
| Pro Val His Arg Leu Thr Lys Lys Leu Gln Asp Pro Glu Lys Leu Pro | |
| 145   150   155 | |

| ctg atc atc gtt gct tgt gga tca ttt tct ccc ata aca tac cta cat | 1067 |
| Leu Ile Ile Val Ala Cys Gly Ser Phe Ser Pro Ile Thr Tyr Leu His | |
| 160   165   170   175 | |

| ttg aga atg ttt gaa atg gct tta gat gat atc aat gag caa acg cgt | 1115 |
| Leu Arg Met Phe Glu Met Ala Leu Asp Asp Ile Asn Glu Gln Thr Arg | |
| 180   185   190 | |

| ttt gaa gtg gtt ggt ggt tat ttt tct cca gta agt gat aac tat caa | 1163 |
| Phe Glu Val Val Gly Gly Tyr Phe Ser Pro Val Ser Asp Asn Tyr Gln | |
| 195   200   205 | |

| aag cga ggg tta gcc cca gct tat cat cgt gtc cgc atg tgc gaa tta | 1211 |
| Lys Arg Gly Leu Ala Pro Ala Tyr His Arg Val Arg Met Cys Glu Leu | |
| 210   215   220 | |

| gca tgc gag cgg aca tca tct tgg tta atg gtt gat gcc tgg gaa tct | 1259 |
| Ala Cys Glu Arg Thr Ser Ser Trp Leu Met Val Asp Ala Trp Glu Ser | |
| 225   230   235 | |

| tta caa tca agt tat aca agg aca gca aaa gtc ttg gac cat ttc aat | 1307 |

```
Leu Gln Ser Ser Tyr Thr Arg Thr Ala Lys Val Leu Asp His Phe Asn
240                 245                 250                 255 cat gaa ata aat atc aag aga ggt gga atc atg act gta gat ggt gaa     1355
His Glu Ile Asn Ile Lys Arg Gly Gly Ile Met Thr Val Asp Gly Glu
                260                 265                 270 aaa atg ggc gta aaa atc atg tta ttg gca ggc ggt gat ctt atc gaa     1403
Lys Met Gly Val Lys Ile Met Leu Leu Ala Gly Gly Asp Leu Ile Glu
            275                 280                 285 tcc atg ggc gag cct cat gtg tgg gct gat tca gac ctg cac cat att     1451
Ser Met Gly Glu Pro His Val Trp Ala Asp Ser Asp Leu His His Ile
        290                 295                 300 ttg ggt aat tat gga tgt ttg atc gtg gaa agg act ggt tct gat gtt     1499
Leu Gly Asn Tyr Gly Cys Leu Ile Val Glu Arg Thr Gly Ser Asp Val
    305                 310                 315 agg tcc ttc ttg ctt tcc cat gat atc atg tat gaa cac aga aga aat     1547
Arg Ser Phe Leu Leu Ser His Asp Ile Met Tyr Glu His Arg Arg Asn
320                 325                 330                 335 atc ctt att atc aaa caa ctt att tac aat gat att tcc tct acg aaa     1595
Ile Leu Ile Ile Lys Gln Leu Ile Tyr Asn Asp Ile Ser Ser Thr Lys
                340                 345                 350 gtg cgg ctt ttc atc aga cgt gga atg tca gtt caa tat ctt ctt cca     1643
Val Arg Leu Phe Ile Arg Arg Gly Met Ser Val Gln Tyr Leu Leu Pro
            355                 360                 365 aac tct gtc atc cgt tac atc caa gag tat aat cta tac att aat caa     1691
Asn Ser Val Ile Arg Tyr Ile Gln Glu Tyr Asn Leu Tyr Ile Asn Gln
        370                 375                 380 agt gaa ccg gtc aag cag gtc ttg gat agc aaa gag tgagtttatt          1737
Ser Glu Pro Val Lys Gln Val Leu Asp Ser Lys Glu
    385                 390                 395 acaactctga tactgcagca gttcaaattt accactttcc tcttcaaggt gcatagaaaa   1797
aaagttcctg gatgcacgat ttaaaatgtt tacagcagag caacaatcat gtgaacaatg   1857
tcaaacattt attttaacac ttaataatta taatataacc acaccagcgg taagtttcat   1917
aaggaaaacc tttcagacaa acattccagt gaatcgtata cgtaaatcag caaaattagc   1977
ttataaaata cagaatccga agatacttga tctactcgcg ttactattaa tgcgggtaat   2037
gatctatatt gaattttgca cgtctatagt aacttaaaag tcttgtaata tttgaagtaa   2097
caatgccgta taatactgca taatagccct atcaatcgga atataccaaa acatcctttt   2156

<210> SEQ ID NO 17
<211> LENGTH: 395
<212> TYPE: PRT
<213> ORGANISM: Saccharomyces cerevisiae

<400> SEQUENCE: 17

Met Asp Pro Thr Lys Ala Pro Asp Phe Lys Pro Pro Gln Pro Asn Glu
1               5                   10                  15

Glu Leu Gln Pro Pro Asp Pro Thr His Thr Ile Pro Lys Ser Gly
            20                  25                  30

Pro Ile Val Pro Tyr Val Leu Ala Asp Tyr Asn Ser Ser Ile Asp Ala
        35                  40                  45

Pro Phe Asn Leu Asp Ile Tyr Lys Thr Leu Ser Ser Arg Lys Lys Asn
    50                  55                  60

Ala Asn Ser Ser Asn Arg Met Asp His Ile Pro Leu Asn Thr Ser Asp
65                  70                  75                  80

Phe Gln Pro Leu Ser Arg Asp Val Ser Glu Glu Ser Glu Gly
            85                  90                  95
```

```
Gln Ser Asn Gly Ile Asp Ala Thr Leu Gln Asp Val Thr Met Thr Gly
                100                 105                 110
Asn Leu Gly Val Leu Lys Ser Gln Ile Ala Asp Leu Glu Glu Val Pro
            115                 120                 125
His Thr Ile Val Arg Gln Ala Arg Thr Ile Glu Asp Tyr Glu Phe Pro
        130                 135                 140
Val His Arg Leu Thr Lys Lys Leu Gln Asp Pro Glu Lys Leu Pro Leu
145                 150                 155                 160
Ile Ile Val Ala Cys Gly Ser Phe Ser Pro Ile Thr Tyr Leu His Leu
                165                 170                 175
Arg Met Phe Glu Met Ala Leu Asp Asp Ile Asn Glu Gln Thr Arg Phe
            180                 185                 190
Glu Val Val Gly Gly Tyr Phe Ser Pro Val Ser Asp Asn Tyr Gln Lys
        195                 200                 205
Arg Gly Leu Ala Pro Ala Tyr His Arg Val Arg Met Cys Glu Leu Ala
210                 215                 220
Cys Glu Arg Thr Ser Ser Trp Leu Met Val Asp Ala Trp Glu Ser Leu
225                 230                 235                 240
Gln Ser Ser Tyr Thr Arg Thr Ala Lys Val Leu Asp His Phe Asn His
                245                 250                 255
Glu Ile Asn Ile Lys Arg Gly Gly Ile Met Thr Val Asp Gly Glu Lys
            260                 265                 270
Met Gly Val Lys Ile Met Leu Leu Ala Gly Gly Asp Leu Ile Glu Ser
        275                 280                 285
Met Gly Glu Pro His Val Trp Ala Asp Ser Asp Leu His His Ile Leu
        290                 295                 300
Gly Asn Tyr Gly Cys Leu Ile Val Glu Arg Thr Gly Ser Asp Val Arg
305                 310                 315                 320
Ser Phe Leu Leu Ser His Asp Ile Met Tyr Glu His Arg Arg Asn Ile
                325                 330                 335
Leu Ile Ile Lys Gln Leu Ile Tyr Asn Asp Ile Ser Ser Thr Lys Val
            340                 345                 350
Arg Leu Phe Ile Arg Arg Gly Met Ser Val Gln Tyr Leu Leu Pro Asn
        355                 360                 365
Ser Val Ile Arg Tyr Ile Gln Glu Tyr Asn Leu Tyr Ile Asn Gln Ser
        370                 375                 380
Glu Pro Val Lys Gln Val Leu Asp Ser Lys Glu
385                 390                 395

<210> SEQ ID NO 18
<211> LENGTH: 2156
<212> TYPE: DNA
<213> ORGANISM: Saccharomyces cerevisiae

<400> SEQUENCE: 18
aaaggatgtt ttggtatatt ccgattgata gggctattat gcagtattat acggcattgt      60
tacttcaaat attacaagac ttttaagtta ctatagacgt gcaaaattca atatagatca     120
ttacccgcat taatagtaac gcgagtagat caagtatctt cggattctgt attttataag     180
ctaattttgc tgatttacgt atacgattca ctggaatgtt tgtctgaaag gttttcctta     240
tgaaacttac cgctggtgtg gttatattat aattattaag tgttaaaata aatgtttgac     300
attgttcaca tgattgttgc tctgctgtaa acattttaaa tcgtgcatcc aggaactttt     360
tttctatgca ccttgaagag gaaagtggta aatttgaact gctgcagtat cagagttgta     420
```

-continued

| | |
|---|---|
| ataaactcac tctttgctat ccaagacctg cttgaccggt tcactttgat taatgtatag | 480 |
| attatactct tggatgtaac ggatgacaga gtttggaaga agatattgaa ctgacattcc | 540 |
| acgtctgatg aaaagccgca ctttcgtaga ggaaatatca ttgtaaataa gttgtttgat | 600 |
| aataaggata tttcttctgt gttcatacat gatatcatgg gaaagcaaga aggacctaac | 660 |
| atcagaacca gtcctttcca cgatcaaaca tccataatta cccaaaatat ggtgcaggtc | 720 |
| tgaatcagcc cacacatgag gctcgcccat ggattcgata agatcaccgc ctgccaataa | 780 |
| catgattttt acgcccattt tttcaccatc tacagtcatg attccacctc tcttgatatt | 840 |
| tatttcatga ttgaaatggt ccaagacttt tgctgtcctt gtaaacttg attgtaaaga | 900 |
| ttcccaggca tcaaccatta ccaagatga tgtccgctcg catgctaatt cgcacatgcg | 960 |
| gacacgatga taagctgggg ctaaccctcg cttttgatag ttatcactta ctggagaaaa | 1020 |
| ataaccacca accacttcaa aacgcgtttg ctcattgata tcatctaaag ccatttcaaa | 1080 |
| cattctcaaa tgtaggtatg ttatgggaga aaatgatcca caagcaacga tgatcagagg | 1140 |
| cagttttttca ggatcttgta actttttcgt caatctgtgt acaggaaatt cgtaatcttc | 1200 |
| aatagttctg gcttgtctta caattgtgtg aggaacttct tccaaatcag caatttggct | 1260 |
| cttcagtacc cccaaattcc cagtcatcgt aacatcctgt agagtagcgt caattccatt | 1320 |
| cgattgccct tcactttcct cctccgatga tacatcccga gatagtggct ggaagtcact | 1380 |
| agtatttaat ggaatatggt ccattcggtt gcttgagttg gcgttttttt tccttgacga | 1440 |
| cagggttttg taaatgtcga gattgaaagg agcatcgatc gaagaattat aatcagctaa | 1500 |
| aacatatgga actatgggtc cagattttgt tatcgtatgt gttggatctg gcggtggttg | 1560 |
| tagttcttca tttggctgtg gcggtttaaa atcgggtgct ttggtgggat ccattacgta | 1620 |
| ataagtgcac tttttcttgc cttctccact ttaaactctc tctctctctc tacttaacag | 1680 |
| tggaggaaca gtgactaagg tagagtatga ttgtactata acttacagtc tactgtcgtc | 1740 |
| acgctgggtc aatttacatt gttattttc ttggagacga caccgtcaca tatggacagc | 1800 |
| gagtatggta gatggtataa gcaaaaaatg gccagaaaca ggcgattatt tggtaaaacg | 1860 |
| taaagattga tcaagacgat aagtttgaga gattgtgaag ctaaataaaa tcgtattgcg | 1920 |
| agtattttac attccatata cgaatagtac gatatccatg tggggtgcga ctcagagact | 1980 |
| ttctattacc cgtctttcaa aaagaaatga gatacgttga tcctgctttt aacaatttcg | 2040 |
| aatcgtttgc gtaattatat gacttgctcc ggtgtataaa taaataaagt acattcttgg | 2100 |
| tactcctgaa cctagcctgg agtaactcgg aataatacac cattgacacc aaaaga | 2156 |

<210> SEQ ID NO 19
<211> LENGTH: 3343
<212> TYPE: DNA
<213> ORGANISM: Saccharomyces cerevisiae
<220> FEATURE:
<221> NAME/KEY: CDS
<222> LOCATION: (1526)...(2728)

<400> SEQUENCE: 19

| | |
|---|---|
| gtttgaattg tgtttgtgtt agaaatttgt gtgctttaat gttatgttat aatgaaatct | 60 |
| tattagattt atttaacgtt tttgctgtgc ttataataaa cattacataa taaaggagt | 120 |
| agaagaaagt ggtagagagg agtacaaatc tacctgccag aactctctcc ttatatatat | 180 |
| ttccagtggt gtctggatta cctacctcaa gccataccat atccatacca tatccataaa | 240 |
| cgcctacaaa atttctaccc caatccagca gcttctatca ctatctcgta taccaccata | 300 |

-continued

```
ggcaccacca ctgtttgtgt aaatttactc ctgagggggg ggtggctcaa cacggtgtag      360
gccttcttcc cgcacaatcc gatgaaaccc cacaatcgcc tccgtctctt ccactgtgca      420
cggcgctagc tcaacatctt ccccgccaca tttactgtgg caaagaaggt gcataatcta      480
aaaaaacata cgtatgagaa tggaaagggc aagataatat cggaccgtag tgagtcactt      540
gcttttggta ttgcaaccaa ctgccgcccc tcttcccgct cttgcaccaa aacgctaaat      600
gcccattgtg atggctcatc caccctcacg acgaagtaag acccgggca caagaaaata       660 cgagatcata acagttcgag tccgtttatt gtgtgcggtt ttggtacgct ttttcgtgag      720
gtgtactacc attcatgaga gtcgttttag gagctgtcat gaaagatatg tatcttgttg      780
atgaactgta aaaatttgca gaattgcgc tattccgttt atttcattgt cgattcggtg      840
ttaatattag gggtacaaaa tatactagaa gttctccctc gaggatatag gaatgcgcaa      900
atgggcattt gatgtgacac aaaatttgga caatataacg attcattttt agatcgttgt     960
tcaaccgtcc cagtggccga gtggttaagg cgatgcctgc tatttcctca gaaaagcaat     1020
taggcattgg gttttacctg cgcaggttcg aatcctgtct gtgacgcttt ttttaatttc     1080
tttactccat gacaaaagcg gataaaaatt cccgcattcg gcgtaaaaaa atccggtttt     1140 tttttttagca ctcgctgttt ttgcctctac cgggtgaaaa atgacgatga agacggctgg    1200
aattgcgctg catccgctta cgtaggatag aacacctaca aagatttacg aactttattg     1260
ctcgaagatt cgctatccat atcttttag tttcccccca tttcacaatg ggataccgtt      1320
gttttttctg taggtacgct ttctcatagt taatagagtc agtaattcat ttcatttttt     1380
gcagaaagga atttcttcac ctaatttaga atttcatcaa catttattgt atctgcatgg     1440
tataacaaat tagaaaaatt tggaagggaa aaaaaactg ttgcgtcaat tacttatacc      1500
agggatagaa aaaaaaaag gaaac atg gat ccc aca aga gct ccg gat ttc        1552
                             Met Asp Pro Thr Arg Ala Pro Asp Phe
                              1               5 aaa ccg cca tct gca gac gag gaa ttg att cct cca ccc gac ccg gaa       1600
Lys Pro Pro Ser Ala Asp Glu Glu Leu Ile Pro Pro Pro Asp Pro Glu
 10              15                  20                  25 tct aaa att ccc aaa tct att cca att att cca tac gtc tta gcc gat       1648
Ser Lys Ile Pro Lys Ser Ile Pro Ile Ile Pro Tyr Val Leu Ala Asp
                 30                  35                  40 gcg aat tcc tct ata gat gca cct ttt aat att aag agg aag aaa aag       1696
Ala Asn Ser Ser Ile Asp Ala Pro Phe Asn Ile Lys Arg Lys Lys Lys
             45                  50                  55 cat cct aag cat cat cat cac cat cat cac agt cgt aaa gaa ggc aat       1744
His Pro Lys His His His His His His His Ser Arg Lys Glu Gly Asn
         60                  65                  70 gat aaa aaa cat cag cat att cca ttg aac caa gac gac ttt caa cca       1792
Asp Lys Lys His Gln His Ile Pro Leu Asn Gln Asp Asp Phe Gln Pro
 75                  80                  85 ctt tcc gca gaa gtg tct tcc gaa gat gat gac gcg gat ttt aga tcc       1840
Leu Ser Ala Glu Val Ser Ser Glu Asp Asp Asp Ala Asp Phe Arg Ser
 90                  95                 100                 105 aag gag aga tac ggt tca gat tca acc aca gaa tca gaa act aga ggt       1888
Lys Glu Arg Tyr Gly Ser Asp Ser Thr Thr Glu Ser Glu Thr Arg Gly
             110                 115                 120 gtt cag aaa tat cag att gct gat tta gaa gaa gtt cca cat gga atc       1936
Val Gln Lys Tyr Gln Ile Ala Asp Leu Glu Glu Val Pro His Gly Ile
         125                 130                 135 gtt cgt caa gca aga acc ttg gaa gac tac gaa ttc ccc tca cac aga       1984
Val Arg Gln Ala Arg Thr Leu Glu Asp Tyr Glu Phe Pro Ser His Arg
 140                 145                 150
```

-continued

```
tta tcg aaa aaa tta ctg gat cca aat aaa ctg ccg tta gta ata gta    2032
Leu Ser Lys Lys Leu Leu Asp Pro Asn Lys Leu Pro Leu Val Ile Val
    155                 160                 165 gca tgt ggg tct ttt tca cca atc acc tac ttg cat cta aga atg ttt    2080
Ala Cys Gly Ser Phe Ser Pro Ile Thr Tyr Leu His Leu Arg Met Phe
170                 175                 180                 185 gaa atg gct tta gat gca atc tct gaa caa aca agg ttt gaa gtc ata    2128
Glu Met Ala Leu Asp Ala Ile Ser Glu Gln Thr Arg Phe Glu Val Ile
                190                 195                 200 ggt gga tat tac tcc cct gtt agt gat aac tat caa aag caa ggc ttg    2176
Gly Gly Tyr Tyr Ser Pro Val Ser Asp Asn Tyr Gln Lys Gln Gly Leu
            205                 210                 215 gcc cca tcc tac cat aga gta cgt atg tgt gaa ttg gcc tgc gaa aga    2224
Ala Pro Ser Tyr His Arg Val Arg Met Cys Glu Leu Ala Cys Glu Arg
        220                 225                 230 acc tca tct tgg ttg atg gtg gat gca tgg gag tca ttg caa cct tca    2272
Thr Ser Ser Trp Leu Met Val Asp Ala Trp Glu Ser Leu Gln Pro Ser
    235                 240                 245 tac aca aga act gcc aag gtc ttg gat cat ttc aat cac gaa atc aat    2320
Tyr Thr Arg Thr Ala Lys Val Leu Asp His Phe Asn His Glu Ile Asn
250                 255                 260                 265 att aag aga ggt ggt gta gct act gtt act gga gaa aaa att ggt gtg    2368
Ile Lys Arg Gly Gly Val Ala Thr Val Thr Gly Glu Lys Ile Gly Val
                270                 275                 280 aaa ata atg ttg ctg gct ggt ggt gac cta ata gag tca atg ggt gaa    2416
Lys Ile Met Leu Leu Ala Gly Gly Asp Leu Ile Glu Ser Met Gly Glu
            285                 290                 295 cca aac gtt tgg gcg gac gcc gat tta cat cac att ctc ggt aat tac    2464
Pro Asn Val Trp Ala Asp Ala Asp Leu His His Ile Leu Gly Asn Tyr
        300                 305                 310 ggt tgt ttg att gtc gaa cgt act ggt tct gat gta agg tct ttt ttg    2512
Gly Cys Leu Ile Val Glu Arg Thr Gly Ser Asp Val Arg Ser Phe Leu
    315                 320                 325 tta tcc cat gat att atg tat gaa cat aga agg aat att ctt atc atc    2560
Leu Ser His Asp Ile Met Tyr Glu His Arg Arg Asn Ile Leu Ile Ile
330                 335                 340                 345 aag caa ctc atc tat aat gat att tct tcc acg aaa gtt cgt cta ttt    2608
Lys Gln Leu Ile Tyr Asn Asp Ile Ser Ser Thr Lys Val Arg Leu Phe
                350                 355                 360 atc aga cgc gcc atg tct gta caa tat ttg tta cct aat tcg gtc atc    2656
Ile Arg Arg Ala Met Ser Val Gln Tyr Leu Leu Pro Asn Ser Val Ile
            365                 370                 375 agg tat atc caa gaa cat aga cta tat gtg gac caa acc gaa cct gtt    2704
Arg Tyr Ile Gln Glu His Arg Leu Tyr Val Asp Gln Thr Glu Pro Val
        380                 385                 390 aag caa gtt ctt gga aac aaa gaa tgatttgccg tccggaattg cttcgttctt  2758
Lys Gln Val Leu Gly Asn Lys Glu
    395                 400 tctttcatct ttctctttac aatttccaat tttcccctac aggaattaat tggagggtac  2818
aagcgagtag aaatgtgaca tatgacttac ctatctgtgt tttagtatag ttttttttc   2878 tgtagtataa ttcacttttta cactaatttt ttcgcctttt tctcttaaag agctaatttc  2938
tataaccttc agcggttata ccaaatataa aaatggaag gaaacaaac agtaagaaat    2998 aagcgcaaca gcacgttagt tcaccattgg attccaacat ttcaaaattt aatctaatgg  3058
caagagatat cacatttttg accgtatttt tagaaagttg tggcgctgta aataatgatg  3118
aggcaggaaa attgttatct gcttggactt caaccgtacg cattgaggga ccggaatcaa  3178
```

-continued

```
ccgactctaa ttcattatat attccactgc taccacctgg aatgttgaaa gtatgtttct    3238
cctagcaaaa ttaaaaccca tccgtgaatg aagcgttact aactataata actggtagct    3298
ttgtcactcg taccaggaaa agtgaagatt aaactgaatt ttaaa                     3343
```

<210> SEQ ID NO 20
<211> LENGTH: 401
<212> TYPE: PRT
<213> ORGANISM: Saccharomyces cerevisiae

<400> SEQUENCE: 20

```
Met Asp Pro Thr Arg Ala Pro Asp Phe Lys Pro Pro Ser Ala Asp Glu
 1               5                  10                  15

Glu Leu Ile Pro Pro Pro Asp Pro Glu Ser Lys Ile Pro Lys Ser Ile
                20                  25                  30

Pro Ile Ile Pro Tyr Val Leu Ala Asp Ala Asn Ser Ser Ile Asp Ala
            35                  40                  45

Pro Phe Asn Ile Lys Arg Lys Lys His Pro Lys His His His His
        50                  55                  60

His His His Ser Arg Lys Glu Gly Asn Asp Lys Lys His Gln His Ile
65                  70                  75                  80

Pro Leu Asn Gln Asp Asp Phe Gln Pro Leu Ser Ala Glu Val Ser Ser
                85                  90                  95

Glu Asp Asp Ala Asp Phe Arg Ser Lys Glu Arg Tyr Gly Ser Asp
            100                 105                 110

Ser Thr Thr Glu Ser Glu Thr Arg Gly Val Gln Lys Tyr Gln Ile Ala
        115                 120                 125

Asp Leu Glu Glu Val Pro His Gly Ile Val Arg Gln Ala Arg Thr Leu
130                 135                 140

Glu Asp Tyr Glu Phe Pro Ser His Arg Leu Ser Lys Lys Leu Leu Asp
145                 150                 155                 160

Pro Asn Lys Leu Pro Leu Val Ile Val Ala Cys Gly Ser Phe Ser Pro
                165                 170                 175

Ile Thr Tyr Leu His Leu Arg Met Phe Glu Met Ala Leu Asp Ala Ile
            180                 185                 190

Ser Glu Gln Thr Arg Phe Glu Val Ile Gly Gly Tyr Tyr Ser Pro Val
        195                 200                 205

Ser Asp Asn Tyr Gln Lys Gln Gly Leu Ala Pro Ser Tyr His Arg Val
210                 215                 220

Arg Met Cys Glu Leu Ala Cys Glu Arg Thr Ser Ser Trp Leu Met Val
225                 230                 235                 240

Asp Ala Trp Glu Ser Leu Gln Pro Ser Tyr Thr Arg Thr Ala Lys Val
                245                 250                 255

Leu Asp His Phe Asn His Glu Ile Asn Ile Lys Arg Gly Gly Val Ala
            260                 265                 270

Thr Val Thr Gly Glu Lys Ile Gly Val Lys Ile Met Leu Leu Ala Gly
        275                 280                 285

Gly Asp Leu Ile Glu Ser Met Gly Glu Pro Asn Val Trp Ala Asp Ala
290                 295                 300

Asp Leu His His Ile Leu Gly Asn Tyr Gly Cys Leu Ile Val Glu Arg
305                 310                 315                 320

Thr Gly Ser Asp Val Arg Ser Phe Leu Leu Ser His Asp Ile Met Tyr
                325                 330                 335

Glu His Arg Arg Asn Ile Leu Ile Ile Lys Gln Leu Ile Tyr Asn Asp
            340                 345                 350
```

```
Ile Ser Ser Thr Lys Val Arg Leu Phe Ile Arg Arg Ala Met Ser Val
        355                 360                 365

Gln Tyr Leu Leu Pro Asn Ser Val Ile Arg Tyr Ile Gln Glu His Arg
    370                 375                 380

Leu Tyr Val Asp Gln Thr Glu Pro Val Lys Gln Val Leu Gly Asn Lys
385                 390                 395                 400

Glu

<210> SEQ ID NO 21
<211> LENGTH: 3343
<212> TYPE: DNA
<213> ORGANISM: Saccharomyces cerevisiae

<400> SEQUENCE: 21
```

| | | | | | |
|---|---|---|---|---|---|
| tttaaaattc | agtttaatct | tcacttttcc | tggtacgagt | gacaaagcta | ccagttatta |   60 |
| tagttagtaa | cgcttcattc | acggatgggt | tttaattttg | ctaggagaaa | catactttca |  120 |
| acattccagg | tggtagcagt | ggaatatata | atgaattaga | gtcggttgat | tccggtccct |  180 |
| caatgcgtac | ggttgaagtc | caagcagata | acaatttttcc | tgcctcatca | ttatttacag |  240 |
| cgccacaact | ttctaaaaat | acggtcaaaa | atgtgatatc | tcttgccatt | agattaaatt |  300 |
| ttgaaatgtt | ggaatccaat | ggtgaactaa | cgtgctgttg | cgcttatttc | ttactgtttg |  360 |
| ttttccttcc | atttttttata | tttggtataa | ccgctgaagg | ttatagaaat | tagctcttta |  420 |
| agagaaaaag | gcgaaaaaat | tagtgtaaaa | gtgaattata | ctacagaaaa | aaaaactata |  480 |
| ctaaaacaca | gataggtaag | tcatatgtca | catttctact | cgcttgtacc | ctccaattaa |  540 |
| ttcctgtagg | ggaaaattgg | aaattgtaaa | gagaaagatg | aaagaaagaa | cgaagcaatt |  600 |
| ccggacggca | aatcattctt | tgtttccaag | aacttgctta | acaggttcgg | tttggtccac |  660 |
| atatagtcta | tgttcttgga | tatacctgat | gaccgaatta | ggtaacaaat | attgtacaga |  720 |
| catggcgcgt | ctgataaata | gacgaacttt | cgtggaagaa | atatcattat | agatgagttg |  780 |
| cttgatgata | agaatattcc | ttctatgttc | atacataata | tcatgggata | acaaaaaaga |  840 |
| ccttacatca | gaaccagtac | gttcgacaat | caaacaaccg | taattaccga | aatgtgatg |  900 |
| taaatcggcg | tccgcccaaa | cgtttggttc | acccattgac | tctattaggt | caccaccagc |  960 |
| cagcaacatt | attttcacac | caatttttc | tccagtaaca | gtagctacac | cacctctctt | 1020 |
| aatattgatt | tcgtgattga | aatgatccaa | gaccttggca | gttcttgtgt | atgaaggttg | 1080 |
| caatgactcc | catgcatcca | ccatcaacca | agatgaggtt | ctttcgcagg | ccaattcaca | 1140 |
| catacgtact | ctatggtagg | atggggccaa | gccttgcttt | tgatagttat | cactaacagg | 1200 |
| ggagtaatat | ccacctatga | cttcaaacct | tgtttgttca | gagattgcat | ctaaagccat | 1260 |
| ttcaaacatt | cttagatgca | agtaggtgat | tggtgaaaaa | gacccacatg | ctactattac | 1320 |
| taacggcagt | ttatttggat | ccagtaattt | tttcgataat | ctgtgtgagg | ggaattcgta | 1380 |
| gtcttccaag | gttcttgctt | gacgaacgat | tccatgtgga | acttcttcta | aatcagcaat | 1440 |
| ctgatatttc | tgaacacctc | tagtttctga | ttctgtggtt | gaatctgaac | cgtatctctc | 1500 |
| cttggatcta | aaatccgcgt | catcatcttc | ggaagacact | tctgcggaaa | gtggttgaaa | 1560 |
| gtcgtcttgg | ttcaatggaa | tatgctgatg | ttttttatca | ttgccttctt | tacgactgtg | 1620 |
| atgatggtga | tgatgatgct | taggatgctt | tttcttcctc | ttaatattaa | aaggtgcatc | 1680 |
| tatagaggaa | ttcgcatcgg | ctaagacgta | tggaataatt | ggaatagatt | tgggaatttt | 1740 |
| agattccggg | tcgggtggag | gaatcaattc | ctcgtctgca | gatggcggtt | tgaaatccgg | 1800 |

```
agctcttgtg ggatccatgt ttccttttt tttttctatc cctggtataa gtaattgacg    1860
caacagtttt ttttccctt ccaaattttt ctaatttgtt ataccatgca gatacaataa    1920
atgttgatga aattctaaat taggtgaaga aattcctttc tgcaaaaaat gaaatgaatt    1980
actgactcta ttaactatga gaaagcgtac ctacagaaaa aacaacggta tcccattgtg    2040
aaatgggggg aaactaaaaa gatatggata gcgaatcttc gagcaataaa gttcgtaaat    2100
ctttgtaggt gttctatcct acgtaagcgg atgcagcgca attccagccg tcttcatcgt    2160
catttttcac ccggtagagg caaaacagc gagtgctaaa aaaaaaccg gatttttta    2220
cgccgaatgc gggaatttt atccgctttt gtcatggagt aaagaaatta aaaaagcgt    2280
cacagacagg attcgaacct gcgcaggtaa aacccaatgc ctaattgctt ttctgaggaa    2340
atagcaggca tcgccttaac cactcggcca ctgggacggt tgaacaacga tctaaaaatg    2400
aatcgttata ttgtccaaat tttgtgtcac atcaaatgcc catttgcgca ttcctatatc    2460
ctcgagggag aacttctagt atattttgta ccctaatat taacaccgaa tcgacaatga    2520
aataaacgga atagcgcaat ttctgcaaat ttttacagtt catcaacaag atacatatct    2580
ttcatgacag ctcctaaaac gactctcatg aatggtagta cacctcacga aaagcgtac    2640
caaaaccgca cacaataaac ggactcgaac tgttatgatc tcgtattttc ttgtgccccg    2700
ggtcttactt cgtcgtgagg gtggatgagc catcacaatg ggcatttagc gttttggtgc    2760
aagagcggga agaggggcgg cagttggttg caataccaaa agcaagtgac tcactacggt    2820
ccgatattat cttgcccttt ccattctcat acgtatgttt tttagatta tgcaccttct    2880
ttgccacagt aaatgtggcg gggaagatgt tgagctagcg ccgtgcacag tggaagagac    2940
ggaggcgatt gtggggtttc atcggattgt gcgggaagaa ggcctacacc gtgttgagcc    3000
accccccct caggagtaaa tttacacaaa cagtggtggt gcctatggtg gtatacgaga    3060
tagtgataga agctgctgga ttggggtaga aattttgtag gcgtttatgg atatggtatg    3120
gatatggtat ggcttgaggt aggtaatcca gacaccactg gaaatatata taaggagaga    3180
gttctggcag gtagatttgt actcctctct accactttct tctactcctt ttattatgta    3240
atgtttatta taagcacagc aaaaacgtta aataaatcta ataagatttc attataacat    3300
aacattaaag cacacaaatt tctaacacaa acacaattca aac                     3343
```

<210> SEQ ID NO 22
<211> LENGTH: 1900
<212> TYPE: DNA
<213> ORGANISM: Saccharomyces cerevisiae
<220> FEATURE:
<221> NAME/KEY: CDS
<222> LOCATION: (813)...(1853)

<400> SEQUENCE: 22

```
ttctactact ccacgtacaa aaaagagcac gctgctttat ttatactttt gtgccacaag      60
aatgatcaac atcaacataa atatcaacta gtatctgcaa cacatctgct ccacggaact     120
aaacccgttg agcagtgccc cgtggaaacg taaactatcg caaattggga ttaacaagcc     180
aaaaacagcc aagcaagatt cacgaaaccg cgcctcgttt ggaccccgaa ggcccattta     240
acggccggcc gttacaagca agatcggcag agcaaaccac tccccagcac cacagcacat     300
cactgcacga gcaacaataa ctagaacatg gcagatagcg aggataccctc tgtgatcctg    360
cagggcatcg acacaatcaa cagcgtggag ggcctggaag aagatggtta cctcagcgac    420
gaggacacgt cactcagcaa cgagctcgca gatgcacagc gtcaatggga agagtcgctg    480
```

```
caacagttga acaagctgct caactgggtc ctgctgcccc tgctgggcaa gtatataggt      540
aggagaatgg ccaagactct atggagtagg ttcattgaac actttgtata agtgtttgtt      600
gtttatgtat ccgcatatag cagttataac agataaatgg cactttcgc acaccgttg        660 ttttatctcc gatagtacgt gggcctttat ttatggtcgt ttaacgaaag aacggcatct      720
tgaattgagc aggtatttaa aagataggac gagaaacaag cacatgatct gtgtcgaaaa      780
aaagtagcaa agagaaaaag taggaggata gg atg aac agg aaa gta gct atc        833
                                    Met Asn Arg Lys Val Ala Ile
                                     1               5 gta acg ggt act aat agt aat ctt ggt ctg aac att gtg ttc cgt ctg        881
Val Thr Gly Thr Asn Ser Asn Leu Gly Leu Asn Ile Val Phe Arg Leu
         10                  15                  20 att gaa act gag gac acc aat gtc aga ttg acc att gtg gtg act tct        929
Ile Glu Thr Glu Asp Thr Asn Val Arg Leu Thr Ile Val Val Thr Ser
 25                  30                  35 aga acg ctt cct cga gtg cag gag gtg att aac cag att aaa gat ttt        977
Arg Thr Leu Pro Arg Val Gln Glu Val Ile Asn Gln Ile Lys Asp Phe
 40                  45                  50                  55 tac aac aaa tca ggc cgt gta gag gat ttg gaa ata gac ttt gat tat       1025
Tyr Asn Lys Ser Gly Arg Val Glu Asp Leu Glu Ile Asp Phe Asp Tyr
                 60                  65                  70 ctg ttg gtg gac ttc acc aac atg gtg agt gtc ttg aac gca tat tac       1073
Leu Leu Val Asp Phe Thr Asn Met Val Ser Val Leu Asn Ala Tyr Tyr
         75                  80                  85 gac atc aac aaa aag tac agg gcg ata aac tac ctt ttc gtg aat gct       1121
Asp Ile Asn Lys Lys Tyr Arg Ala Ile Asn Tyr Leu Phe Val Asn Ala
         90                  95                 100 gcg caa ggt atc ttt gac ggt ata gat tgg atc gga gcg gtc aag gag       1169
Ala Gln Gly Ile Phe Asp Gly Ile Asp Trp Ile Gly Ala Val Lys Glu
        105                 110                 115 gtt ttc acc aat cca ttg gag gca gtg aca aat ccg aca tac aag ata       1217
Val Phe Thr Asn Pro Leu Glu Ala Val Thr Asn Pro Thr Tyr Lys Ile
120                 125                 130                 135 caa ctg gtg ggc gtc aag tct aaa gat gac atg ggg ctt att ttc cag       1265
Gln Leu Val Gly Val Lys Ser Lys Asp Asp Met Gly Leu Ile Phe Gln
                140                 145                 150 gcc aat gtg ttt ggt ccg tac tac ttt atc agt aaa att ctg cct caa       1313
Ala Asn Val Phe Gly Pro Tyr Tyr Phe Ile Ser Lys Ile Leu Pro Gln
        155                 160                 165 ttg acc agg gga aag gct tat att gtt tgg att tcg agt att atg tcc       1361
Leu Thr Arg Gly Lys Ala Tyr Ile Val Trp Ile Ser Ser Ile Met Ser
        170                 175                 180 gat cct aag tat ctt tcg ttg aac gat att gaa cta cta aag aca aat       1409
Asp Pro Lys Tyr Leu Ser Leu Asn Asp Ile Glu Leu Leu Lys Thr Asn
185                 190                 195 gcc tct tat gag ggc tcc aag cgt tta gtt gat tta ctg cat ttg gcc       1457
Ala Ser Tyr Glu Gly Ser Lys Arg Leu Val Asp Leu Leu His Leu Ala
200                 205                 210                 215 acc tac aaa gac ttg aaa aag ctg ggc ata aat cag tat gta gtt caa       1505
Thr Tyr Lys Asp Leu Lys Lys Leu Gly Ile Asn Gln Tyr Val Val Gln
                220                 225                 230 ccg ggc ata ttt aca agc cat tcc ttc tcc gaa tat ttg aat ttt ttc       1553
Pro Gly Ile Phe Thr Ser His Ser Phe Ser Glu Tyr Leu Asn Phe Phe
        235                 240                 245 acc tat ttc ggc atg cta tgc ttg ttc tat ttg gcc agg ctg ttg ggg       1601
Thr Tyr Phe Gly Met Leu Cys Leu Phe Tyr Leu Ala Arg Leu Leu Gly
        250                 255                 260
```

```
tct cca tgg cac aat att gat ggt tat aaa gct gcc aat gcc cca gta    1649
Ser Pro Trp His Asn Ile Asp Gly Tyr Lys Ala Ala Asn Ala Pro Val
    265                 270                 275 tac gta act aga ttg gcc aat cca aac ttt gag aaa caa gac gta aaa    1697
Tyr Val Thr Arg Leu Ala Asn Pro Asn Phe Glu Lys Gln Asp Val Lys
280                 285                 290                 295 tac ggt tct gct acc tct agg gat ggt atg cca tat atc aag acg cag   1745
Tyr Gly Ser Ala Thr Ser Arg Asp Gly Met Pro Tyr Ile Lys Thr Gln
                300                 305                 310 gaa ata gac cct act gga atg tct gat gtc ttc gct tat ata cag aag   1793
Glu Ile Asp Pro Thr Gly Met Ser Asp Val Phe Ala Tyr Ile Gln Lys
            315                 320                 325 aag aaa ctg gaa tgg gac gag aaa ctg aaa gat caa att gtt gaa act   1841
Lys Lys Leu Glu Trp Asp Glu Lys Leu Lys Asp Gln Ile Val Glu Thr
        330                 335                 340 aga acc ccc att taatatatct ctgcgtacat atgtatatat atatatgtgt       1893
Arg Thr Pro Ile
    345 gtatata                                                            1900
```

<210> SEQ ID NO 23
<211> LENGTH: 347
<212> TYPE: PRT
<213> ORGANISM: Saccharomyces cerevisiae

<400> SEQUENCE: 23

```
Met Asn Arg Lys Val Ala Ile Val Thr Gly Thr Asn Ser Asn Leu Gly
 1               5                  10                  15

Leu Asn Ile Val Phe Arg Leu Ile Glu Thr Glu Asp Thr Asn Val Arg
                20                  25                  30

Leu Thr Ile Val Val Thr Ser Arg Thr Leu Pro Arg Val Gln Glu Val
            35                  40                  45

Ile Asn Gln Ile Lys Asp Phe Tyr Asn Lys Ser Gly Arg Val Glu Asp
        50                  55                  60

Leu Glu Ile Asp Phe Asp Tyr Leu Leu Val Asp Phe Thr Asn Met Val
65                  70                  75                  80

Ser Val Leu Asn Ala Tyr Tyr Asp Ile Asn Lys Lys Tyr Arg Ala Ile
                85                  90                  95

Asn Tyr Leu Phe Val Asn Ala Ala Gln Gly Ile Phe Asp Gly Ile Asp
                100                 105                 110

Trp Ile Gly Ala Val Lys Glu Val Phe Thr Asn Pro Leu Glu Ala Val
            115                 120                 125

Thr Asn Pro Thr Tyr Lys Ile Gln Leu Val Gly Val Lys Ser Lys Asp
        130                 135                 140

Asp Met Gly Leu Ile Phe Gln Ala Asn Val Phe Gly Pro Tyr Tyr Phe
145                 150                 155                 160

Ile Ser Lys Ile Leu Pro Gln Leu Thr Arg Gly Lys Ala Tyr Ile Val
                165                 170                 175

Trp Ile Ser Ser Ile Met Ser Asp Pro Lys Tyr Leu Ser Leu Asn Asp
                180                 185                 190

Ile Glu Leu Leu Lys Thr Asn Ala Ser Tyr Glu Gly Ser Lys Arg Leu
            195                 200                 205

Val Asp Leu Leu His Leu Ala Thr Tyr Lys Asp Leu Lys Lys Leu Gly
        210                 215                 220

Ile Asn Gln Tyr Val Val Gln Pro Gly Ile Phe Thr Ser His Ser Phe
225                 230                 235                 240
```

| | | | | | | | | | | | |
|---|---|---|---|---|---|---|---|---|---|---|---|
|Ser|Glu|Tyr|Leu|Asn|Phe|Phe|Thr|Tyr|Phe|Gly|Met|Leu|Cys|Leu|Phe|
| | | |245| | | | |250| | | |255| | | |

Tyr Leu Ala Arg Leu Gly Ser Pro Trp His Asn Ile Asp Gly Tyr
           260                  265                270

Lys Ala Ala Asn Ala Pro Val Tyr Val Thr Arg Leu Ala Asn Pro Asn
      275                  280              285

Phe Glu Lys Gln Asp Val Lys Tyr Gly Ser Ala Thr Ser Arg Asp Gly
      290                  295              300

Met Pro Tyr Ile Lys Thr Gln Glu Ile Asp Pro Thr Gly Met Ser Asp
305              310              315              320

Val Phe Ala Tyr Ile Gln Lys Lys Leu Glu Trp Asp Glu Lys Leu
           325                  330              335

Lys Asp Gln Ile Val Glu Thr Arg Thr Pro Ile
           340                  345

<210> SEQ ID NO 24
<211> LENGTH: 1900
<212> TYPE: DNA
<213> ORGANISM: Saccharomyces cerevisiae

<400> SEQUENCE: 24

```
tatatacaca catatatata tatacatatg tacgcagaga tatattaaat gggggttcta      60
gtttcaacaa tttgatcttt cagtttctcg tcccattcca gtttcttctt ctgtatataa     120
gcgaagacat cagacattcc agtagggtct atttcctgcg tcttgatata tggcatacca     180
tccctagagg tagcagaacc gtattttacg tcttgtttct caaagtttgg attggccaat     240
ctagttacgt atactggggc attggcagct ttataaccat caatattgtg ccatggagac     300
cccaacagcc tggccaaata gaacaagcat agcatgccga aataggtgaa aaaattcaaa     360
tattcggaga aggaatggct tgtaaatatg cccggttgaa ctacatactg atttatgccc     420
agcttttttca gtctttgta ggtggccaaa tgcagtaaat caactaaacg cttggagccc     480
tcataagagg catttgtctt tagtagttca atatcgttca acgaaagata cttaggatcg     540
gacataatac tcgaaatcca acaatataaa gcctttcccc tggtcaattg aggcagaatt     600
ttactgataa agtagtacgg accaaacaca ttggcctgga aaataagccc catgtcatct     660
ttagacttga cgcccaccag ttgtatcttg tatgtcggat ttgtcactgc ctccaatgga     720
ttggtgaaaa cctccttgac cgctccgatc caatctatac cgtcaaagat accttgcgca     780
gcattcacga aaaggtagtt tatcgccctg tacttttgt tgatgtcgta atatgcgttc     840
aagcacactca ccatgttggt gaagtccacc aacagataat caaagtctat ttccaaatcc     900
tctacacggc ctgatttgtt gtaaaaatct ttaatctggt taatcacctc ctgcactcga     960
ggaagcgttc tagaagtcac cacaatggtc aatctgacat tggtgtcctc agtttcaatc    1020
agacggaaca caatgttcag accaagatta ctattagtac ccgttacgat agctactttc    1080
ctgttcatcc tatcctccta cttttctct ttgctacttt ttttcgacac agatcatgtg    1140
cttgtttctc gtcctatctt ttaaatacct gctcaattca agatgccgtt ctttcgttaa    1200
acgaccataa ataaggccc acgtactatc ggagataaaa caacgggtgt gcgaaaagtg    1260
ccatttatct gttataactg ctatatgcgg atacataaac aacaaacact tatacaaagt    1320
gttcaatgaa cctactccat agagtcttgg ccattctcct acctatatac ttgcccagca    1380
ggggcagcag gacccagttg agcagcttgt tcaactgttg cagcgactct tcccattgac    1440
gctgtgcatc tgcgagctcg ttgctgagtg acgtgtcctc gtcgctgagg taaccatctt    1500
```

```
cttccaggcc ctccacgctg ttgattgtgt cgatgccctg caggatcaca gaggtatcct    1560
cgctatctgc catgttctag ttattgttgc tcgtgcagtg atgtgctgtg gtgctgggga    1620 gtggttttgct ctgccgatct tgcttgtaac ggccggccgt taaatgggcc ttcgggtcc    1680 aaacgaggcg cggtttcgtg aatcttgctt ggctgttttt ggcttgttaa tcccaatttg    1740
cgatagttta cgtttccacg ggcactgct caacggggtt agttccgtgg agcagatgtg    1800
ttgcagatac tagttgatat ttatgttgat gttgatcatt cttgtggcac aaaagtataa    1860
ataaagcagc gtgctctttt ttgtacgtgg agtagtagaa                          1900
```

<210> SEQ ID NO 25
<211> LENGTH: 59
<212> TYPE: DNA
<213> ORGANISM: Artificial Sequence
<220> FEATURE:
<223> OTHER INFORMATION: primer for PCR

<400> SEQUENCE: 25

```
aggaaagtag ctatcgtaac gggtactaat agtaatcttg gtctcttggc ctcctctag      59
```

<210> SEQ ID NO 26
<211> LENGTH: 59
<212> TYPE: DNA
<213> ORGANISM: Artificial Sequence
<220> FEATURE:
<223> OTHER INFORMATION: primer for PCR

<400> SEQUENCE: 26

```
tacgcagaga tatattaaat gggggttcta gtttcaacaa tttcgttcag aatgacacg      59
```

<210> SEQ ID NO 27
<211> LENGTH: 62
<212> TYPE: DNA
<213> ORGANISM: Artificial Sequence
<220> FEATURE:
<223> OTHER INFORMATION: primer for PCR

<400> SEQUENCE: 27

```
ttaacagccg cgcccatcat gcaagatcct gatggtattg acattctctt ggcctcctct     60
ag                                                                    62
```

<210> SEQ ID NO 28
<211> LENGTH: 59
<212> TYPE: DNA
<213> ORGANISM: Artificial Sequence
<220> FEATURE:
<223> OTHER INFORMATION: primer for PCR

<400> SEQUENCE: 28

```
gcatatcaat tttaacagac ctcgctgaaa gactctgaat cctcgttcag aatgacacg      59
```

<210> SEQ ID NO 29
<211> LENGTH: 429
<212> TYPE: PRT
<213> ORGANISM: Aspergillus nidulans

<400> SEQUENCE: 29

```
Thr Leu Ala Glu Glu Asn Met Thr Leu Phe Ile His Cys Tyr Ser Lys
  1               5                  10                  15

Gly His Glu Asn Leu Gln Val Thr Ala Ile His Ile Leu Cys Asp Met
             20                  25                  30

Leu Ile Ser His Pro Ser Leu Val Ala Pro Val Thr Gln Ala Asp Lys
```

-continued

```
                35                  40                  45
Glu Thr Val Ala Pro Pro Ala Phe Gln Lys Pro Leu Leu Lys Val Phe
             50                  55                  60

Ser Arg Ala Leu Lys Pro Asn Ser Pro Ala Ser Val Gln Thr Ala Ala
 65                  70                  75                  80

Ala Thr Ala Leu Ser Lys Leu Leu Thr Gly Val Phe Thr Pro Ser
                 85                  90                  95

Ala Ala Asn Ile Pro Asp Ala Ile Gln Glu Phe Asn Gln His Ala Ile
                100                 105                 110

Glu Thr Leu Leu Gln Ser Leu Val Ser Phe Phe His Pro Arg Thr
                115                 120                 125

Arg Glu Asn Pro Ala Leu Arg Gln Ala Leu Ala Tyr Phe Phe Pro Val
            130                 135                 140

Tyr Cys His Ser Arg Pro Asp Asn Thr Gln His Met Arg Lys Ile Thr
145                 150                 155                 160

Val Pro Val Ile Arg Thr Ile Leu Asn Ser Ala Glu Glu Tyr Tyr Ser
                165                 170                 175

Leu Glu Ala Glu Glu Asp Ser Asp Gly Asp Ile Asp Glu Ser Val Gly
            180                 185                 190

Glu Lys Glu Leu Lys Ala Leu Met Ser Gly Val Leu Gly Met Leu Ala
        195                 200                 205

Glu Trp Thr Asp Glu Arg Arg Val Ile Gly Leu Gly Gly Glu Arg Val
    210                 215                 220

Leu Ala Gly Gly Leu Ala Ser Ser Asn Val Cys Gly Ile Ile His Leu
225                 230                 235                 240

Gln Leu Ile Lys Asp Ile Leu Glu Arg Val Leu Gly Ile Ser Glu Gly
                245                 250                 255

Ser Asn Arg Cys Ser Lys Gln Gln Arg Lys Leu Leu Phe Ser Leu Met
            260                 265                 270

Ser Lys Leu Tyr Ile Ala Pro Pro Thr Ala Leu Ser Arg Ser Ala Ser
        275                 280                 285

Gln Ala Pro Glu Asp Asp Ser Phe Arg Ser Ser Val Arg Ser Ser His
    290                 295                 300

Gly Glu Leu Asn Pro Glu Asn Leu Ala Leu Ala Gln Glu Val Lys Glu
305                 310                 315                 320

Leu Leu Asp Gln Thr Ile Glu Glu Gly Val Ala Ala Asp Ala Ala Ser
                325                 330                 335

Arg Asn Ala Leu Val Lys Val Lys Asn Val Val Leu Lys Leu Leu Ala
            340                 345                 350

Ala Pro Met Arg Pro Ser Ser Ala Arg Gly Arg Glu Ser Ser Val Glu
        355                 360                 365

Ser Asp Ile Gly Ser Val Arg Ser Ser Arg Ser Val Arg Pro Ser Val
    370                 375                 380

Glu Pro Gly Phe Gly Arg Arg Gly Val Ser Val Glu Pro Ser Ile Met
385                 390                 395                 400

Glu Glu Asp Glu Asn Glu Asp Ser Arg Ala Thr Leu Asp Ser Arg Met
                405                 410                 415

Thr Val Ile Lys Glu Glu Asp Ala Asp Ala Met Glu Glu
            420                 425
```

<210> SEQ ID NO 30
<211> LENGTH: 147
<212> TYPE: PRT
<213> ORGANISM: Aspergillus nidulans -continued

```
<400> SEQUENCE: 30

Leu Leu Ser Pro Pro Leu Val Arg Ala Thr Val Ile Phe Pro Ser Ser
 1               5                  10                  15

Ser Ser Cys Arg Ser Arg Leu Lys Tyr Ser Val Ser Cys Ser Asp Leu
            20                  25                  30

Gln Leu Leu Arg Ala Asp Thr Leu His Ile Ser Ala Ile Met Thr Glu
        35                  40                  45

Ser Thr Gln Glu Gln Gly Asn Asp Gly Gln Arg Met Pro Pro Ala Pro
    50                  55                  60

Ala Thr Pro Val Glu Asp Tyr Val Phe Pro Glu Tyr Arg Leu Lys Arg
65                  70                  75                  80

Val Met Asp Asp Pro Glu Lys Thr Pro Leu Leu Ile Ala Cys Gly
                85                  90                  95

Ser Phe Ser Pro Ile Thr Phe Leu His Leu Arg Met Phe Glu Met Ala
                100                 105                 110

Ala Asp Tyr Val Lys Leu Ser Thr Asp Phe Glu Ile Ile Gly Gly Tyr
                115                 120                 125

Leu Ser Pro Val Ser Asp Ala Tyr Arg Lys Ala Gly Leu Ala Ser Ala
                130                 135                 140

Asn His Arg
145

<210> SEQ ID NO 31
<211> LENGTH: 91
<212> TYPE: PRT
<213> ORGANISM: Aspergillus nidulans

<400> SEQUENCE: 31

Ile Ala Met Cys Gln Arg Ala Val Asp Gln Thr Ser Asp Trp Met Met
 1               5                  10                  15

Val Asp Thr Trp Glu Pro Met His Lys Glu Tyr Gln Pro Thr Ala Ile
            20                  25                  30

Val Leu Asp His Phe Asp Tyr Glu Ile Asn Thr Val Arg Lys Gly Ile
        35                  40                  45

Asp Thr Gly Lys Gly Thr Arg Lys Arg Val Gln Val Val Leu Leu Ala
    50                  55                  60

Gly Ala Asp Leu Val His Thr Met Ser Thr Pro Gly Val Trp Ser Glu
65                  70                  75                  80

Lys Asp Leu Asp His Ile Leu Gly Gln Tyr Gly
                85                  90

<210> SEQ ID NO 32
<211> LENGTH: 92
<212> TYPE: PRT
<213> ORGANISM: Aspergillus nidulans

<400> SEQUENCE: 32

Thr Phe Ile Val Glu Arg Ser Gly Thr Asp Ile Asp Glu Ala Leu Ala
 1               5                  10                  15

Ala Leu Gln Pro Trp Lys Lys Asn Ile His Val Ile Gln Gln Leu Ile
            20                  25                  30

Gln Asn Asp Val Ser Ser Thr Lys Ile Arg Leu Phe Leu Arg Arg Asp
        35                  40                  45

Met Ser Val Arg Tyr Leu Ile Pro Asp Pro Val Ile Glu Tyr Ile Tyr
    50                  55                  60
```

```
-continued

Glu Asn Asn Leu Tyr Met Asp Asp Gly Thr Thr Gln Pro Thr Ala Asp
 65                  70                  75                  80

Lys Gly Lys Thr Arg Glu Glu Pro Ala Pro Ser Asn
                 85                  90

<210> SEQ ID NO 33
<211> LENGTH: 68
<212> TYPE: PRT
<213> ORGANISM: Aspergillus nidulans

<400> SEQUENCE: 33

Ala Lys Ala Ala Leu Arg Arg Lys Lys Val His Glu Lys Asn Leu Glu
  1               5                  10                  15

Gln Thr Gln Ala Gln Ile Val Gln Leu Glu Gln Gln Ile Tyr Ser Ile
                 20                  25                  30

Glu Ala Ala Asn Ile Asn His Glu Thr Leu Ala Ala Met Lys Ala Ala
             35                  40                  45

Gly Ala Ala Met Glu Lys Ile His Asn Gly Met Thr Val Glu Gln Val
         50                  55                  60

Asp Glu Thr Met
 65

<210> SEQ ID NO 34
<211> LENGTH: 70
<212> TYPE: PRT
<213> ORGANISM: Aspergillus nidulans

<400> SEQUENCE: 34

Asp Lys Leu Arg Glu Gln Gln Ala Ile Asn Asp Glu Ile Ala Ile Ala
  1               5                  10                  15

Ile Thr Asn Pro Gly Phe Gly Glu Gln Val Asp Glu Asp Leu Glu
                 20                  25                  30

Ala Glu Leu Glu Gly Met Glu Gln Glu Ala Met Asp Glu Arg Met Leu
             35                  40                  45

His Thr Gly Thr Val Pro Val Ala Asp Gln Leu Asn Arg Leu Pro Ala
         50                  55                  60

Pro Ala Asn Ala Glu Pro
 65                  70

<210> SEQ ID NO 35
<211> LENGTH: 25
<212> TYPE: PRT
<213> ORGANISM: Aspergillus nidulans

<400> SEQUENCE: 35

Ala Lys Ala Lys Gln Lys Ala Glu Glu Glu Asp Glu Glu Ala Glu Leu
  1               5                  10                  15

Glu Lys Leu Arg Ala Glu Met Ala Met
                 20                  25
```